(12) United States Patent
Bera et al.

(10) Patent No.: US 8,865,664 B2
(45) Date of Patent: Oct. 21, 2014

(54) HYDROPHOBICALLY ENHANCED AMINOGLYCOSIDES

(75) Inventors: Smritilekha Bera, Winnipeg (CA); George G. Zhanel, Winnipeg (CA); Frank Schweizer, Winnipeg (CA)

(73) Assignee: University of Manitoba, Winnipeg (CA)

( * ) Notice: Subject to any disclaimer, the term of this patent is extended or adjusted under 35 U.S.C. 154(b) by 469 days.

(21) Appl. No.: 13/003,175

(22) PCT Filed: Jul. 9, 2009

(86) PCT No.: PCT/IB2009/006651
§ 371 (c)(1),
(2), (4) Date: Apr. 4, 2011

(87) PCT Pub. No.: WO2010/004433
PCT Pub. Date: Jan. 14, 2010

(65) Prior Publication Data
US 2011/0178037 A1    Jul. 21, 2011

Related U.S. Application Data

(60) Provisional application No. 61/079,338, filed on Jul. 9, 2008, provisional application No. 61/093,199, filed on Aug. 29, 2008.

(51) Int. Cl.
```
A61K 31/7008    (2006.01)
A61K 31/702     (2006.01)
A61K 31/7028    (2006.01)
C07H 15/234     (2006.01)
C07H 15/232     (2006.01)
C07H 5/06       (2006.01)
```

(52) U.S. Cl.
CPC ................................ C07H 15/232 (2013.01)
USPC ............... 514/39; 514/25; 514/41; 514/42; 514/54; 536/13.2; 536/13.7

(58) Field of Classification Search
USPC ............ 514/42, 39, 41, 54, 25; 536/22.1, 4.1, 536/13.2, 13.7
See application file for complete search history.

(56) References Cited

U.S. PATENT DOCUMENTS

| | | | |
|---|---|---|---|
| 2003/0054556 A1 | 3/2003 | Lehn et al. | 435/45 |
| 2004/0229265 A1* | 11/2004 | Lapidot et al. | 435/6 |

FOREIGN PATENT DOCUMENTS

| | | |
|---|---|---|
| CA | 2687689 | 3/2009 |
| WO | WO 03/066648 | 8/2003 |
| WO | WO 2008/040792 | 4/2008 |

OTHER PUBLICATIONS

STN abstract of Lapidot et al.; US 20040229265 A1; Nov. 18, 2004 (abstract sent).*

Begg and Barclay, "Aminoglycosides—50 years on," *Br. J. Clin. Pharmac.*, 39:597-603, 1995.

Belmont et al., "Aminoclycoside-derived cationic lipids as efficient vectors for gene transfection in vitro and in vivo," *The Journal of Gene Medicine*, 4: 517-526, 2002.

Bera et al., "Design, synthesis, and antibacterial activities of neomycin-lipid conjugates: polycationic lipids with potent grampositive activity," *J. Med. Chem.*, 51:6160-6161, 2008.

Biehl et al., "Anthelmintics for swine," *Vet. Clin. North. Am. Food. Anim. Pract.*, 2:481-488, 1986.

Botto and Coxon, "Nitrogen-15 nuclear magnetic resonance spectroscopy of neomycin B and related aminoglycosides," *J Am. Chem.. Soc.*, 105:1021-1028, 1983.

Chen et al., "Structure-based discovery of ligands targeted to the RNA double helix," *Biochemistry*, 36:11402-11407, 1997.

Constantinou-Kokotou et al., "Study of aminoglycoside-nucleic acid interactions by an HPLC method," *Bioorg. Med. Chem. Let.*, 11:1015-1018, 2001.

Dorman et al., "Nitrogen-15 nuclear magnetic resonance spectroscopy. The nebramycin aminoglycosides," *J. Am. Chem Soc.*, 98:6885-6888, 1976.

Hayes and Wolf, "Molecular mechanisms of drug resistance," *Biochem. J.*, 272:281-295, 1990.

Hooper, In: *Aminoglycociede Antibiotics*, Springer-Verlag, NY, Heidelberg, 1982.

International Search Report and Written Opinion issued in PCT/IB2009/006651, dated Feb. 17, 2010.

Jacoby and Archer., "New mechanisms of bacterial resistance to antimicrobial agents," *N. Engl. J. Med.*, 324:601-612, 1991.

(Continued)

*Primary Examiner* — Shaojia Anna Jiang
*Assistant Examiner* — Michael C Henry
(74) *Attorney, Agent, or Firm* — Fulbright & Jaworski LLP

(57) ABSTRACT

Hydrophobically enhanced aminoglycosides have been prepared and shown to be effective antibacterial agents. These agents may be used in the treatment or prevention of various bacterial infections. Methods of preparing these agents also permit facile synthetic access. Formula (I).

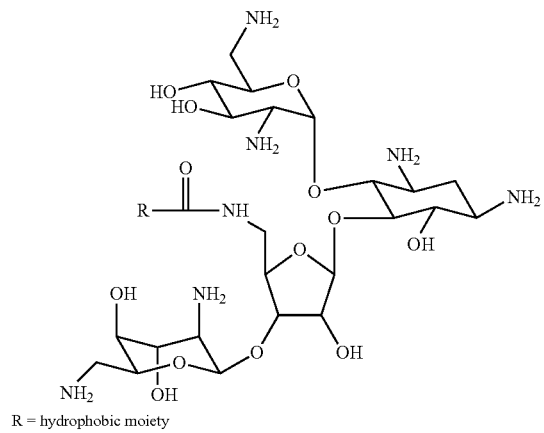

R = hydrophobic moiety

7 Claims, 18 Drawing Sheets

(56) References Cited

OTHER PUBLICATIONS

Jono et al., "Effect of alkyl chain length of benzalkonium chloride on the bactericidal activity and binding to organic materials," *Chem. Pharm. Bull.*, 34(10: 4215-4224, 1986.

Kabara et al., "Fatty acids and derivatives as antimicrobial agents," *Antimicrobial Agents and Chemotherapy*, 2(1): 23-28, 1972.

Kirk et al., "Neomycin—Acridine Conjugate: A Potent Inhibitor of Rev-RRE Binding," *J. Am. Chem. Soc.*, 122:980-981, 2000.

Kithara et al., "Antimicrobial activity of saturated fatty acids and fatty amines against mehicillin-resistant *Staphylococcus aureus*," *Biol. Pharm. Bull.*, 27(9): 1321-1326, 2004.

Kudyba et al., "Synthesis of paromomycin derivatives modified at C(5') to selectively target bacterial rRNA," *Carbohydrate Research*, 342: 499-519, 2007.

Li et al., "Investigation of the regioselectivity for the Staudinger reaction and its application for the synthesis of aminoglycosides with NI modification," *J. Org. Chem.*, 72:4055-4066, 2007.

Mei et al., "Inhibition of an HIV-1 Tat-derived peptide binding to TAR RNA by aminoglycoside antibiotics," *Bioorg. Med. Chem. Lett.*, 5: 2755-2760, 1995.

Mingeot-Leclercq and Tulkens, "Aminoglycosides: Nephrotoxicity," *Antimicrob. Agents Chemother.*, 43:1003-1012, 1999.

Mingeot-Leclercq et al., "Aminoglycosides: activity and resistance," *Antimicrob. Agents Chemother.*, 43: 727-737, 1999.

Moazed and Noller, "Interaction of antibiotics with functional sites in 16S ribosomal RNA," *Nature*, 327:389-394, 2007.

Nakagawa et al., "Hygromycin A, an antitreponemal substance. II. Therapeutic effect for swine dysentery," *J. Antibiot.*, 40:1627-1635, 1987.

Neu, "The crisis in antibiotic resistance," *Science*, 257:1064-1073, 1992.

Ohyama et al., "Anion coordination by aminoglycosides: structural and charge effects," *Chem Commun.*, 467-468, 1998.

Sainlos et al., "Aminoglycoside-derived cationic lipids for gene transfection: synthesis of kanamycin a derivatives," *Eur. J. Org. Chem.*, 2764-2774, 2003.

Sainlos et al., "Kanamycin—A-derived cationic lipids as vectors for gene transfection," *ChemBioChem*, 6:1023-1033, 2005.

Schwarz et al., "In vitro activities of spectinomycin and comparator agents against *Pasteurella multocida* and *Mannheimia haemolytica* from respiratory tract infections of cattle," *J. Antimicrob. Chemother.*, 53:379-382, 2004.

Shelburne et al., "In vitro killing of community-associated methicillin-resistant *Staphylococcus aureus* with drug combinations," *Antimicrobial Agents and Chemotherapy*, 48(10): 4016-4019, 2004.

Taber et al., "In vitro activities of spectinomycin and comparator agents against *Pasteurella multocida* and *Mannheimia haemolytica* from respiratory tract infections of cattle," *Microbiol. Rev.*, 439-457, 1987.

Vieira et al., "Cationic lipids and surfactants as antifungal agents: mode of action," *J. Antimicriob. Chemother.*, 53:379-382, 2004.

von Ahsen and Noller, "Footprinting the sites of interaction of antibiotics with catalytic group I intron RNA," *Science*, 260:1500-1503, 1993.

Wang et al., "Electrostatic Interactions in RNA Aminoglycosides Binding," *J. Am. Chem. Soc.*, 119:8734-8735, 1997.

Werstuck et al., "A non-canonical base pair within the human immunodeficiency virus rev-responsive element is involved in both rev and small molecule recognition," *Chem. Biol.*, 3:129-137, 1996.

Zhang et al., "Surprising alteration of antibacterial activity of 5—modified neonmycin agains resistant bacteria," *J. Med. Chem.*, 51:7563-7573, 2008.

\* cited by examiner

| Cmpd | MIC (µg/mL) | | | | | | | |
|---|---|---|---|---|---|---|---|---|
| | S. aureus[a] | MRSA[b] | S. epidermidis[c] | MRSE[d] | S. pneumoniae[e] | E. coli[f] | E.coli[g] | P. aeruginosa[h] |
| Gentamicin | 1 | 2 | 0.25 | 32 | 4 | 1 | 128 | 4 |
| Neomycin B | 2 | 256 | 1 | 0.5 | 64 | 8 | 4 | 512 |
| Kanamycin A | 4 | >512 | 2 | 128 | 8 | 8 | 16 | >512 |
| 13 | 16 | >512 | 2 | 32 | 64 | 16 | 16 | >512 |
| 14 | 32 | >512 | 4 | 8 | 128 | 64 | 64 | 256 |
| 15 | 4 | 8 | 2 | 2 | 64 | 32 | 64 | 128 |
| 16 | 8 | 8 | 4 | 4 | 64 | 128 | 128 | 64 |
| 17 | 16 | 32 | 4 | 4 | 128 | 128 | 64 | >512 |
| 18 | 16 | 256 | 2 | 64 | >512 | 32 | 64 | 256 |
| 19 | 16 | 128 | 8 | 16 | >256 | 32 | 64 | >256 |
| 30 | 8 | 16 | 2 | 2 | 64 | 32 | 32 | 64 |
| 31 | 4 | 4 | 1 | 4 | 32 | 32 | 32 | 32 |

FIG. 4

| Cmpd | MIC (µg/mL) | | | | | | | |
|---|---|---|---|---|---|---|---|---|
| | S. aureus[a] | MRSA[b] | S. epidermidis[c] | MRSE[d] | S. pneumoniae[e] | E. coli[f] | E. coli[g] | P. aeruginosa[h] |
| Gentamicin | 1 | 2 | 0.25 | 32 | 4 | 1 | 128 | 4 |
| Neomycin B | 2 | 256 | 1 | 0.5 | 64 | 8 | 4 | 512 |
| 24 | 8 | 32 | 4 | 4 | 64 | 16 | 16 | 128 |
| 22 | 16 | 128 | 4 | 4 | 128 | 32 | 32 | >256 |

FIG. 6

Table 3

| Control organism | Genta-micin | Neo-mycin B | Kana-mycin A | 4A | 9A | 7A | 11A | 14A | 20A | 17A | 22A |
|---|---|---|---|---|---|---|---|---|---|---|---|
| S.aureus ATCC 29213 | 1 | 1 | 4 | 1 | 4 | 128 | 32 | >256 | 8 | 16 | 64 |
| MRSA ATCC 33592 | 1 | 128 | >512 | 1 | 1 | 256 | 32 | >256 | 16 | 16 | 64 |
| S.epidermidis ATCC 14990 | 0.25 | 0.25 | 2 | 0.5 | 1 | 64 | 4 | >128 | 2 | 8 | 16 |
| MRSE (CZ >32) CAN-ICU 61589 | 32 | 0.25 | 128 | 0.5 | 2 | 64 | 8 | >128 | 2 | 8 | 32 |
| S.pneumoniae ATCC 49619 | 1 | 8 | 8 | 16 | 8 | >256 | 64 | >256 | 8 | 32 | 16 |
| E.coli ATCC 25922 | 1 | 2 | 8* | 32 | 32 | 128 | >256 | >128 | 0.5/1 | 8 | 1 |
| E.coli (Gent-R) CAN-ICU 61714 | 256 | 4 | 16 | 16 | 64 | 256 | >256 | >256 | 32 | >256 | 128 |
| E.coli ATCC (Amikacin 32) CAN-ICU 63074 | 8 | 32 | 32 | 16 | 64 | >256 | >256 | >128 | 256 | 32 | >256 |
| P.aeruginosa ATCC 27853 | 2 | 512 | >512 | 256 | 128 | >256 | >256 | >128 | 256 | 32 | >256 |
| P.aeruginosa (Gent-R) CAN-ICU 62308 | 128 | 512 | >512 | 128 | 128 | >256 | >256 | >128 | 256 | 32 | 256 |
| S. maltophilia CAN-ICU 62584 | >512 | >512 | - | 4 | 16 | >256 | >256 | >256 | >256 | 128 | >256 |
| A. baumannii CAN-ICU 63169 | 128 | 0.25 | 256 | 32 | 32 | >256 | >256 | >256 | 256 | 128 | 256 |
| K.pneumoniae ATCC 13883 | | | | 256 | 256 | >256 | >256 | >256 | | 64 | 128 |

FIG. 17

HYDROPHOBICALLY ENHANCED AMINOGLYCOSIDES

This application is a national phase application under 35 U.S.C. §371 of International Application No. PCT/IB2009/006651 filed Jul. 9, 2009, which claims priority to U.S. Provisional Patent Application Ser. No. 61/079,338 filed Jul. 9, 2008 and U.S. Provisional Patent Application Ser. No. 61/093,199 filed Aug. 29, 2008, the entire contents of which are hereby incorporated by reference without disclaimer.

BACKGROUND OF THE INVENTION

1. Field of the Invention

The present invention relates generally to the fields of organic chemistry and antibacterial agents. More particularly, it concerns preparation of hydrophobically enhanced aminoglycosides, such as aminoglycoside-lipid conjugates, and methods of treating antibacterial infections with these aminoglycosides.

2. Description of the Related Art

Aminoglycoside antibiotics constitute a large family of clinically important drugs used in the treatment of bacterial infections (Umezawa and Hooper, 1982). They effect their antibacterial activity by interfering with ribosomal function (via binding to rRNA), which ultimately results in the disruption of protein biosynthesis (Moazed and Noller, 1987; Purohit and Stern, 1994). Aminoglycoside antibiotics present a wide spectrum of action and are effective against most Gram-negative bacteria and certain Gram-positive bacteria. Many of them, e.g., amikacin, gentamicin, kanamycin, neomycin, netilmycin, streptomycin, and tobramycin, have been used clinically for decades as potent antimicrobial agents (Begg and Carclay, 1995). Other analogs, e.g., hygromycin A and spectinomycin, are used frequently as animal medicines in veterinary and agricultural applications (Biehl, 1986; Nakagawa et al., 1987; Schwarz et al., 2004).

Although aminoglycoside antibiotics exhibit potent bactericidal activity, their widespread use has been compromised by dose-related nephrotoxicity and ototoxicity (Mingeot-Leclerq and Tulkens, 1999; Mingeot-Leclerq et al., 1999). Furthermore, as with other antibiotic regimens, their use as the primary treatment of life threatening infections has also been curtailed due to the rapid emergence of resistant strains of bacteria (Neu, 1992; Hayes and Wolf, 1990; Jacoby et al., 1991). Indeed, the explosive growth of multi-drug resistant (MDR) bacteria in hospitals and the community has led to an emerging crisis where an increasing number of antibiotics cease to be of clinical usefulness (Neu, 1992). Despite this growing concern, only one new class of antibiotics, the oxazolidinones, has entered the clinic during the past two decades (Walsh, 2000). As a result, there is a pressing need for novel classes of antibacterial agents with reduced resistance.

SUMMARY OF THE INVENTION

The present invention addresses the needs discussed above by providing novel hydrophobically enhanced aminoglycosides that exhibit antibacterial activity. Indeed, some of the aminoglycosides discussed herein show marked improvements over traditional aminoglycoside antibiotics, such as neomycin and kanamycin. In addition to providing methods of making hydrophobically enhanced aminoglycosides, methods of treating bacterial infections using these aminoglycosides are also provided by the present invention.

Accordingly, the present invention contemplates hydrophobically enhanced aminoglycosides. As used herein, a "hydrophobically enhanced aminoglycoside" is an aminoglycoside that is rendered more hydrophobic by virtue of conjugation of a moiety to the aminoglycoside than the hydrophobicity of the aminoglycoside without the conjugated moiety. The term "more hydrophobic" refers to any measurable increase in difference in the hydrophobicity of the hydrophobically enhanced aminoglycoside versus the aminoglycoside alone. Methods of measuring hydrophobicity are well-known in the art. One such method is through measuring the octanol-water partition coefficient of the compounds. See, e.g., Sangster, 1997, which is incorporated herein by reference in its entirety. Non-limiting examples of hydrophobically enhanced aminoglycosides include aminoglycoside-lipid conjugates, as described herein, as well as aminoglycoside-aryl/heteroaryl conjugates, aminoglycoside-cholesteroyl conjugates and aminoglycoside-lysine conjugates, each of which are described herein.

As discussed below, the term "hydrophobe," as used herein (e.g., an aminoglycoside-hydrophobe conjugate), refers to the -lipid, -aryl/heteroaryl, -lysine and -cholesteroyl moieties as described herein, or any combination thereof. In certain embodiments, a hydrophobe refers to a -lipid or a substituted or unsubstituted phenyl group.

In certain embodiments, an aminoglycoside-hydrophobe conjugate is contemplated, wherein at least one hydrophobe is conjugated at a primary hydroxy position of the aminoglycoside through a linker. The aminoglycoside may be further defined as an aminoglycoside antibiotic. The linker may be, for example, an amide linker, an aminoacyl linker, an ester linker, an oxyacyl linker, a thioester linker, an oxythioacyl linker, a carbamate linker, a urea linker, a thiourea linker, an ether linker, a carbonate linker, or an amino linker. In particular embodiments, the conjugation is through an amide linker. In certain embodiments, at least a second hydrophobe is conjugated at a primary amino position of the aminoglycoside.

In any embodiments herein that employs an aminoglycoside, the aminoglycoside may be an aminoglycoside antibiotic. Such agents are well known in the art. In certain embodiments, the aminoglycoside antibiotic is selected from the group consisting of a neomycin, a kanamycin, paromomycin, amikacin, a gentamicin, netilmycin, a streptomycin, tobramycin, a hygromycin and a spectinomycin. In some embodiments, the aminoglycoside antibiotic is selected from the group consisting of a neomycin, kanamycin, amikacin, streptomycin, tobramycin and hygromycin. In more particular embodiments, the aminoglycoside antibiotic is neomycin or kanamycin. Any one or more of these aminoglycoside antibiotics may be excluded, in certain embodiments. For example, in certain embodiments, the aminoglycoside antibiotic is not kanamycin or is not neomycin. Another aminoglycoside antibiotic that may be employed is neamine.

Lipids are a type of hydrophobe that may be conjugated to an aminoglycoside. Lipids are described herein. In certain embodiments, a lipid comprises only carbon-carbon single bonds. In certain embodiments, a lipid comprises at least one double bond. Certain aminoglycoside-lipid conjugates may be further defined as a moiety of formula (I)

$$C_aH_{2a+1} \tag{I}$$

wherein a is 5-45. In certain embodiments, a is at least about or at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or higher, or any range derivable therein. In this or any embodiment described herein, a may be an odd number or an even number, in certain embodiments. In particular embodiments, the lipid is further defined as —$C_5H_{11}$, —$C_{11}H_{23}$, —$C_{15}H_{31}$, or —$C_{19}H_{39}$. In certain embodiments, an aminoglycoside-lipid conjugate is further defined as a moiety of formula (I)

$$C_aH_{2a-x} \tag{II}$$

wherein a is as described above and x is an odd number such that $2a-x \geq 0$. In particular embodiments, the lipid is further defined as —$C_{17}H_{31}$.

In certain embodiments, two or more hydrophobes are conjugated to an aminoglycoside-hydrophobe conjugate through two or more linkers. These two or more hydrophobes may be conjugated at two or more secondary hydroxy positions of the aminoglycoside, for example, or they may be conjugated at two or more secondary amino positions of the aminoglycoside, or a mixture of such conjugations may be in play. The hydrophobes may be the same or different and/or the linkers may be the same or different.

Any aminoglycoside employed herein, in isolation or conjugated to a hydrophobe, may exist with one or more free amino groups (—$NH_2$). In such embodiments, the aminoglycoside or aminoglycoside-hydrophobe conjugate may exist as a trifluoroacetic acid salt (TFA salt). Any aminoglycoside discussed herein may comprise a guanidino group (—NH— C(=NR)NHR, wherein R is H or an amino protecting group) attached to a primary or secondary amino position of the aminoglycoside, and the aminoglycoside may be isolated or may be conjugated to a hydrophobe. In certain embodiments, then, an aminoglycoside of the aminoglycoside-hydrophobe comprises at least one primary or secondary amino group, and the aminoglycoside-hydrophobe is present as a trifluoroacetic acid salt. Moreover, in certain embodiments, an aminoglycoside-hydrophobe comprises at least one guanidino group at a primary or secondary amino position of the aminoglycoside.

Non-limiting examples of aminoglycoside-hydrophobe conjugates that are aminoglycoside-lipid conjugates of the present invention include:

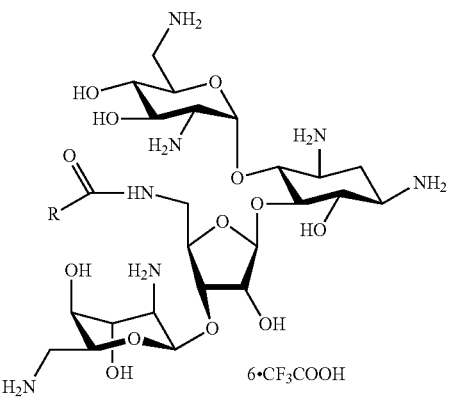

wherein R=$C_5H_{11}$, $C_{11}H_{23}$, $C_{15}H_{31}$, $C_{19}H_{39}$ or $C_{17}H_{31}$; or

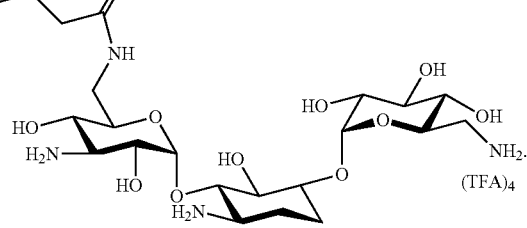

Other embodiments of the present invention contemplate an aminoglycoside-lipid conjugate, wherein at least one lipid is conjugated at a primary amino position of the aminoglycoside through a linker, wherein the aminoglycoside-lipid conjugate is further defined as not the following compound:

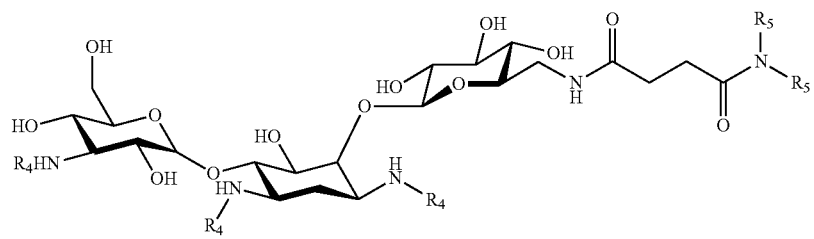

wherein $R_4$ is H or an amino protecting group; and $R_5$ is $C_{18}H_{37}$. The aminoglycoside-lipid conjugate may comprise at least one guanidino group at a primary or secondary amino position of the aminoglycoside, in certain embodiments. The aminoglycoside of the aminoglycoside-lipid may comprise at least one primary or secondary amino group, and the aminoglycoside-lipid may be present as a trifluoroacetic acid salt.

Other aminoglycoside-hydrophobe conjugates of the present invention are shown below, wherein each conjugate may be further defined as an aminoglycoside-aryl/heteroaryl conjugate, such as an aminoglycoside-aryl conjugate:

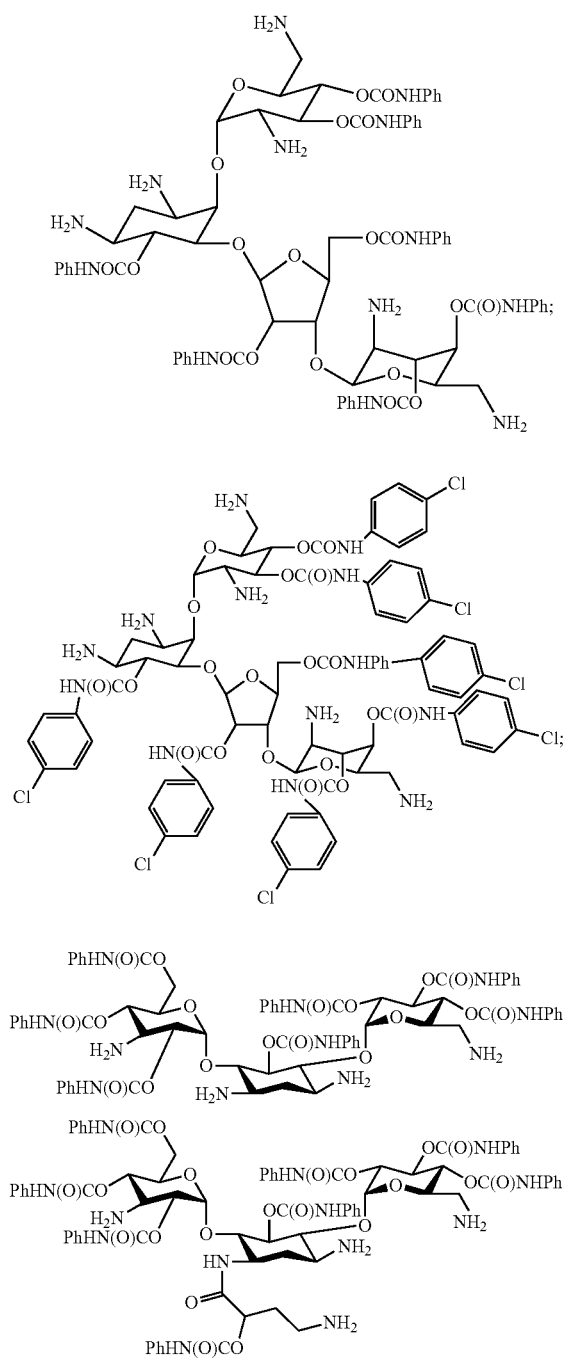

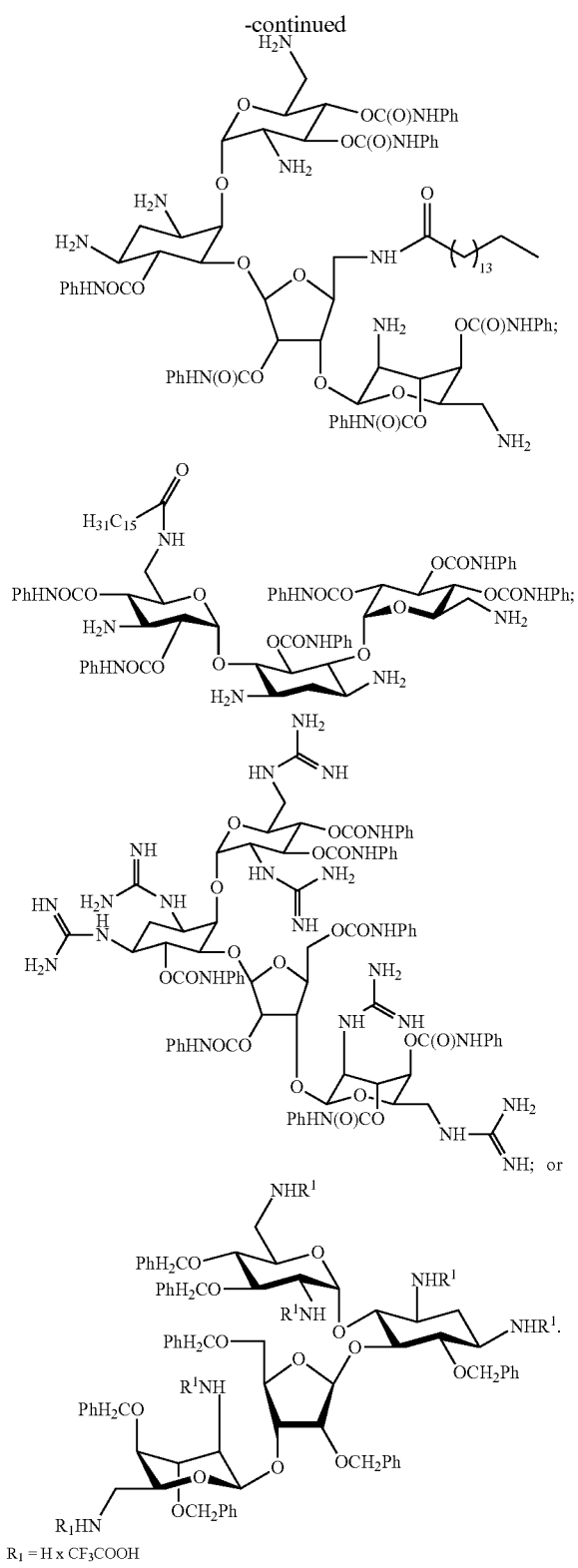

Also contemplated by the present invention are aminoglycoside-hydrophobe conjugates, wherein at least two hydrophobes are conjugated at least two secondary hydroxy positions of the aminoglycoside through at least two linkers. In these or any aminoglycoside-hydrophobe conjugate herein, each hydrophobe may be the same. Each hydrophobe may be further defined as substituted or unsubstituted phenyl in this or any other embodiment herein. In certain embodiments, each of the linkers in an aminoglycoside-hydrophobe conjugate are either both carbamate linkers or both ether linkers. In certain embodiments, at least two hydrophobes are different, wherein at least two linkers are different. In certain embodiments, the aminoglycoside is further defined as an aminoglycoside antibiotic, such as a neomycin, a kanamycin, amikacin, or neamine. In certain embodiments, the aminoglycoside-hydrophobe comprises at least one guanidino group at a primary or secondary amino position of the aminoglycoside. In certain embodiments, the aminoglycoside of the aminoglycoside-hydrophobe comprises at least one primary or secondary amino group, and the aminoglycoside-hydrophobe is present as a trifluoroacetic acid salt. Non-limiting examples of aminoglycoside-hydrophobe conjugates, wherein at least two hydrophobes are conjugated at least two secondary hydroxy positions of the aminoglycoside through at least two linkers, are shown below:

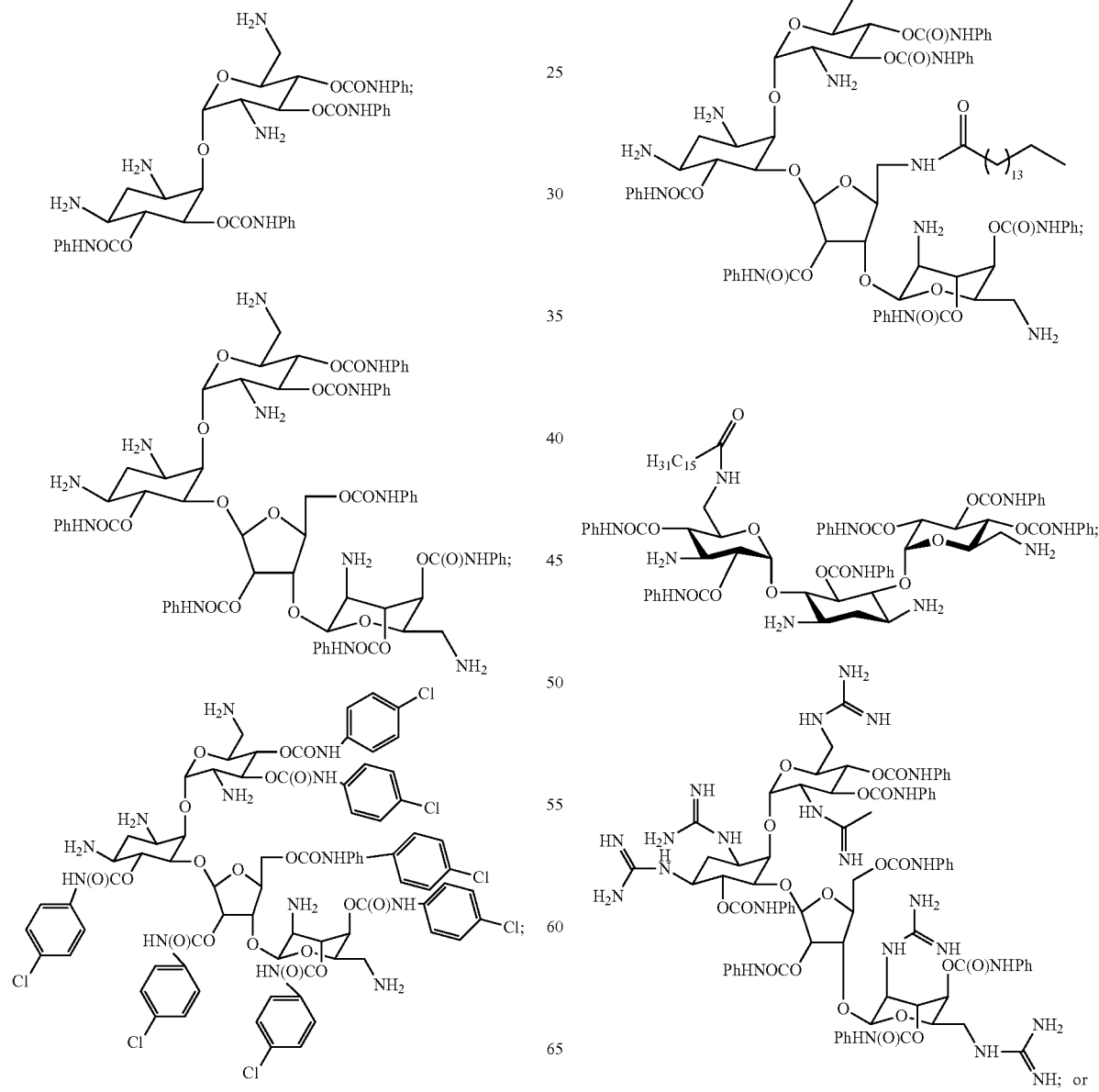

-continued

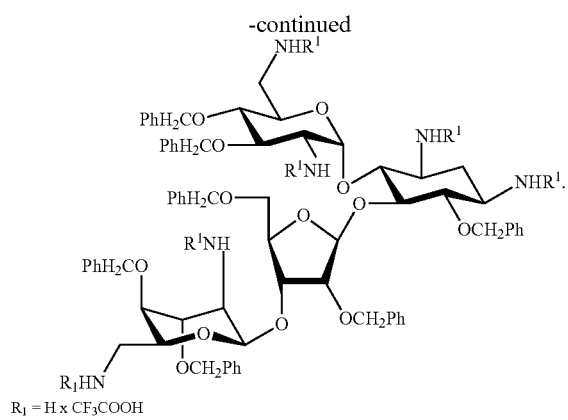

$R_1 = H \times CF_3COOH$

⑦ indicates text missing or illegible when filed

Methods of making hydrophobically enhanced aminoglycosides are also contemplated. For example, the present invention contemplates methods of making an aminoglycoside-lipid conjugate comprising conjugating a reagent comprising a lipid to a primary hydroxy position of an aminoglycoside. The method may further comprise obtaining an aminoglycoside having a primary hydroxy group. The method may further comprise replacing a primary hydroxy group at the primary hydroxy position of the aminoglycoside with a primary amino group. In certain embodiments, the conjugating step may be further defined as conjugating a reagent comprising a lipid to the primary amino group to form a —NHC(O)R group, wherein R is the lipid. The method may further comprise formation of an aminoglycoside comprising a primary azide. The method may further comprise at least one primary amino group of the aminoglycoside with a protecting group. The method may further comprise protecting at least one secondary amino group of the aminoglycoside with a protecting group. The reagent comprising a lipid may, in certain embodiments, be further defined as lipid-$CO_2H$. In certain embodiments, the aminoglycoside-lipid conjugate comprises at least one primary or secondary amino group, the method further comprising converting the primary or secondary amino group to a guanidino group. The method may further comprise oxidizing the primary hydroxy position of an aminoglycoside to a carboxylic acid and conjugating the carboxylic acid with a reagent that is further defined as lipid-$NH_2$ or lipid-OH.

Methods may further comprise conjugating a hydrophobe to the aminoglycoside-lipid conjugate. The hydrophobe may be a second lipid. In this or any other embodiment herein, the hydrophobe may be substituted or unsubstituted phenyl.

Other general aspects of the present invention contemplate a method of making an aminoglycoside-hydrophobe conjugate, wherein the conjugate comprises at least two hydrophobes and wherein each hydrophobe is further defined as substituted or unsubstituted phenyl, comprising conjugating at least two equivalents of a reagent comprising the hydrophobe to at least two secondary hydroxy positions of the aminoglycoside. The reagent may be further defined as, for example, a hydrophobe-isocyanate, wherein the aminoglycoside-hydrophobe conjugate that is made comprises a carbamate linker between the aminoglycoside and each of the hydrophobes. In other embodiments, the reagent may be further defined as a hydrophobe-halide, wherein the aminoglycoside-hydrophobe conjugate that is made comprises an ether linker between the aminoglycoside and each of the hydrophobes. In certain embodiments, the aminoglycoside-hydrophobe conjugate comprises at least one primary or secondary amino group, the method further comprising converting the primary or secondary amino group to a guanidino group. In certain embodiments, the aminoglycoside comprises at least one lipid conjugated to at least one primary amino position of the aminoglycoside through an amide bond.

The present invention also contemplates pharmaceutical compositions. A pharmaceutical composition may comprise, for example, an aminoglycoside-hydrophobe conjugate in a pharmaceutically acceptable formulation. The aminoglycoside-hydrophobe conjugate may be any aminoglycoside-hydrophobe conjugate described herein. Non-limiting examples include an aminoglycoside-hydrophobe conjugate wherein at least one hydrophobe is conjugated at a primary hydroxy position of the aminoglycoside through a linker, and an aminoglycoside-lipid conjugate wherein at least one lipid is conjugated at a primary amino position of the aminoglycoside through a linker, wherein the aminoglycoside-lipid conjugate is further defined as not the following compound:

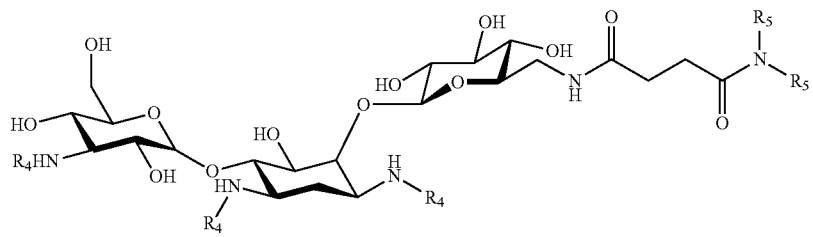

wherein $R_4$ is H or an amino protecting group; and $R_5$ is $C_{18}H_{37}$.

Hydrophobically enhanced aminoglycosides may be used in methods of treatment. For example, the present invention contemplates a method of treating a bacterial infection in a subject comprising administering to the subject an effective amount of an aminoglycoside antibiotic-hydrophobe conjugate. Any aminoglycoside antibiotic-hydrophobe conjugate discussed herein may be employed in such methods, such as an aminoglycoside antibiotic-aryl conjugate, such as wherein the aryl group is substituted or unsubstituted phenyl.

The bacteria causing the bacterial infection may be a multi-drug resistant bacteria, for example. The bacterial infection may be caused by, for example, a Gram-positive bacteria. Non-limiting examples of Gram-positive bacteria include *Staphylococcus aureus* methicillin-resistant *Staphylococcus aureus* (MRSA), *Staphylococcus epidermidis*, methicillin-resistant *S. epidermidis* (MRSE), *Enterococcus faecalis*, *Enterococcus faecium*, *Streptococcus pneumoniae*, or *Mycobacterium tuberculosis*. In particular embodiments, the aminoglycoside is further defined as neomycin. Regarding aminoglycoside-antibiotic hydrophobe conjugates further defined as aminoglycoside-antibiotic lipid conjugates, the lipid may be any lipid described herein. In certain embodiments, the lipid may be further defined as a moiety of formula (I):

$$C_aH_{2a+1} \quad (I)$$

wherein a is 15.

In certain embodiments regarding methods of treating bacterial infection in a subject, or any other embodiment herein, an aminoglycoside antibiotic-hydrophobe conjugate is further defined as a kanamycin-hydrophobe conjugate. Such methods may treat infections caused by, for example, Gram-positive bacteria, such as *S. aureus* or methicillin-resistant *S. aureus*, although these are only non-limiting examples. The lipid may be any lipid described herein, such as a moiety of formula (I):

$$C_aH_{2a+1} \quad (I)$$

wherein a is 15 or 19. The Gram-positive bacteria may be, for example, methicillin-resistant *S. aureus* or methicillin-resistant *S. epidermidis*.

Methods of the present invention may be used to treat bacterial infections caused by a Gram-negative bacteria, in certain embodiments, such as *E. coli*. Other Gram-negative bacteria include *Pseudomonas aeruginosa, Stenotrophomonas maltophilia, Acinetobacter baumannii* and *Klebsiella pneumoniae*. In particular embodiments, an aminoglycoside-lipid conjugate comprises a lipid that is further defined as a compound of formula (I):

$$C_aH_{2a+1} \quad (I)$$

wherein a is 5-7.

In particular embodiments, the following aminoglycoside-aryl conjugate may be employed in methods described herein regarding Gram-negative bacteria:

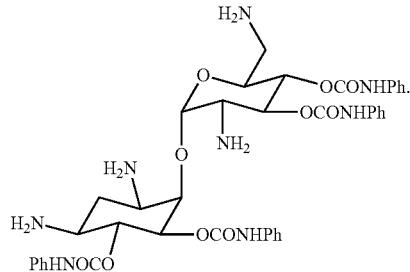

A non-limiting example of an aminoglycoside-hydrophobe that may be employed in methods of the present invention is shown below:

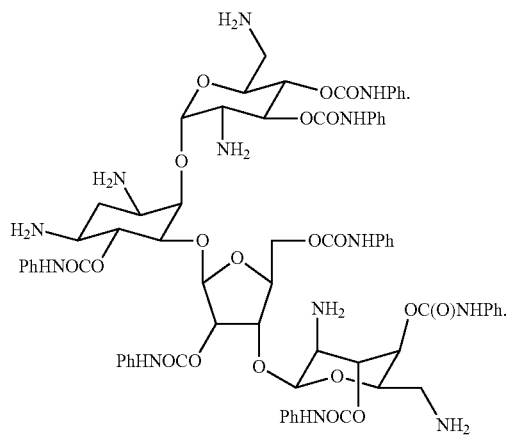

This aminoglycoside-hydrophobe conjugate may be employed, for example, when the bacterial infection is caused by *S. aureus*, methicillin-resistant *S. aureus*, methicillin-resistant *S. epidermidis, Stenotrophomonas maltophilia*, gentamicin-resistant *E. coli* or amikacin-resistant *E. coli*.

In certain embodiments, an aminoglycoside-hydrophobe is further defined as

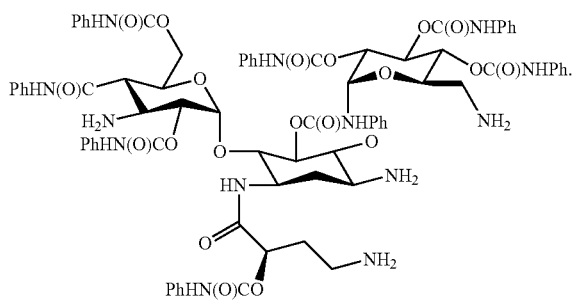

This aminoglycoside-hydrophobe conjugate may be employed, for example, when the bacterial infection is caused by *S. epidermidis*, methicillin-resistant *S. epidermidis, Streptococcus pneumoniae*, or *E. coli*.

In certain embodiments regarding treatment of a bacterial infection using a hydrophobically enhanced aminoglycoside of the present invention, the minimum inhibitory concentration of the aminoglycoside antibiotic-hydrophobe conjugate (MIC) is ≤64 μg/mL. In certain embodiments, the MIC is ≤32 μg/mL. In certain embodiments, the minimum inhibitory concentration is about, at most about, or at least about 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or lower μg/mL, or any range derivable therein. Certain methods contemplate an additional step comprising administration of a second antibacterial agent.

In certain embodiments, methods of the present invention may further comprise diagnosing a subject as needing treatment for a bacterial infection prior to administering an aminoglycoside antibiotic-hydrophobe conjugate. Administration may be via any means described herein such as through topical administration to skin of the subject, wherein the skin has a bacterial infection.

Also contemplated are methods of preventing a bacterial infection in a subject comprising administering to the subject an effective amount of an aminoglycoside antibiotic-lipid conjugate. Such methods may further comprise diagnosing the subject as needing preventative treatment for the bacterial infection prior to administering the aminoglycoside antibiotic-hydrophobe conjugate. The aminoglycoside antibiotic-hydrophobe conjugate may be topically administered to skin of the subject, wherein the skin is at risk of having a bacterial infection.

Another general aspect of the present invention contemplates a method of treating a bacterial infection in a subject comprising administering to the subject an effective amount of a neomycin-hydrophobe (e.g., lipid) conjugate, wherein the effective amount of the neomycin-hydrophobe (e.g., lipid) conjugate is less than the effective amount of neomycin.

In yet another general aspect of the present invention, methods of treating a bacterial infection in a subject comprising administering to the subject an effective amount of a kanamycin-hydrophobe (e.g., lipid) conjugate, wherein the effective amount of the kanamycin-hydrophobe (e.g., lipid) conjugate is less than the effective amount of kanamycin, are contemplated.

In any embodiment herein, a hydrophobically enhanced aminoglycoside may comprise an aryl/heteroaryl group, as described herein. The aryl/heteroaryl group may comprise, for example, substituted phenyl or unsubstituted phenyl. In certain embodiments, the aryl/heteroaryl group comprises a polycyclic aromatic hydrocarbon (PAH), which may be substituted or unsubstituted. In certain embodiments, at least one ring atom of a PAH is substituted by nitrogen, oxygen, or sulfur. A non-limiting example of a PAH is the following:

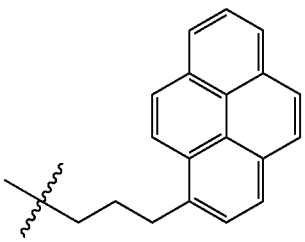

Other hydrophobically enhanced aminoglycosides comprising an aryl/heteroaryl group are described herein.

In particular embodiments, a hydrophobically enhanced aminoglycoside does not comprise a —$C_{18}H_{37}$ group, a cholesteroyl derivative, or a pyrenyl derivative. In certain embodiments, a hydrophobically enhanced aminoglycoside is further defined as not any of the following compounds:

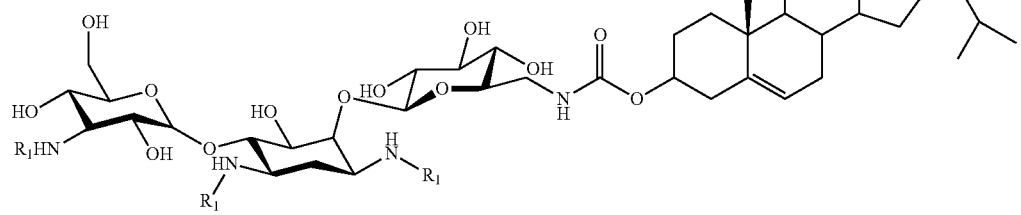

wherein $R_1$ is H, protected amino, or guanidino;

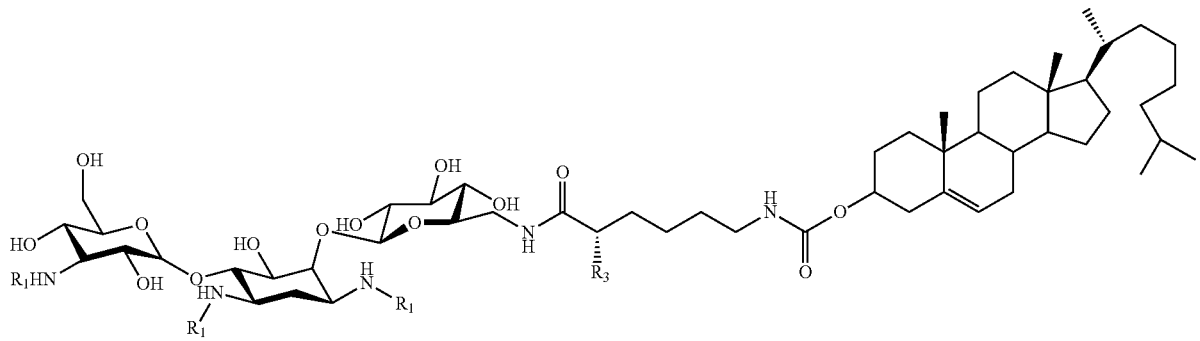

wherein: $R_2$ is H or an amino protecting group; and $R_3$ is H, $NH_2$, protected amino, or

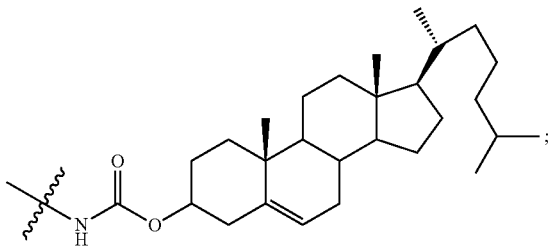

-continued

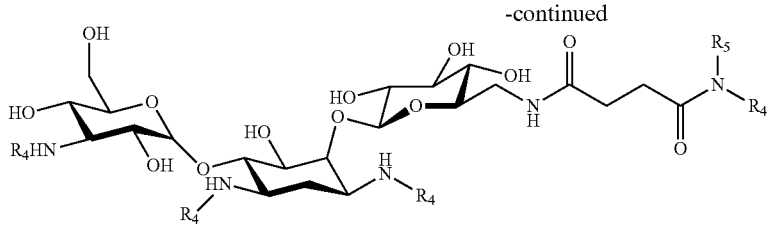

or wherein: $R_4$ is H or an amino protecting group; and $R_5$ is $C_{18}H_{37}$.

In certain embodiments, a hydrophobically enhanced aminoglycoside comprises a linker that not comprise any of the following:
(i) an amide bond in combination with a carbamate bond;
(ii) two amide bonds; or
(iii) a single carbamate bond.

In certain embodiments, the conjugation between an aminoglycoside and a hydrophobic moiety is not through either of the following linkers: carbamate;

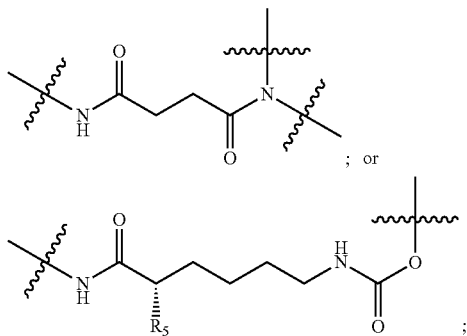

wherein $R_5$ is H, $NH_2$, protected amino, or

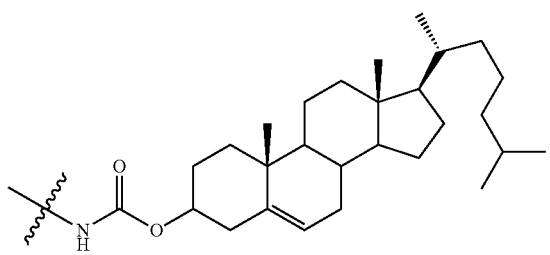

The hydrophobically enhanced aminoglycosides of the present invention differ from other antibiotics in several ways. For example, a hydrophobically enhanced aminoglycoside of the present invention may possess a multiply cationic aminoglycoside "head" as opposed to antimicrobial cationic lipids known in the art, which possesses only one or two positive charges. In certain embodiments, a hydrophobically enhanced aminoglycoside comprises 3, 4, 5, or 6 or more positive charges, or any range derivable therein, in the aminoglycoside "head" group.

As discussed herein, hydrophobically enhanced aminoglycosides offer improvements in antibacterial activity over traditional antibiotics, such as aminoglycoside antibiotics or antimicrobial cationic lipids. For example, hydrophobically enhanced aminoglycosides may exhibit improved antibacterial activity compared to, e.g., neomycin, a kanamycin, paromomycin, amikacin, a gentamicin, netilmycin, a streptomycin, tobramycin, a hygromycin, or a spectinomycin. In particular embodiments, an aminoglycoside antibiotic that is hydrophobically modified as described herein demonstrates improved antibacterial activity versus the unmodified aminoglycoside antibiotic. In certain embodiments, improvements may be seen in one or more of the following bacteria: Staphylococcus aureus methicillin-resistant Staphylococcus aureus (MRSA), Staphylococcus epidermidis, methicillin-resistant S. epidermidis (MRSE), Enterococcus faecalis, Enterococcus faecium, Streptococcus pneumoniae, E. coli, Pseudomonas aeruginosa, Stenotrophomonas maltophilia, Acinetobacter baumannii, Klebsiella pneumoniae or Mycobacterium tuberculosis.

In certain embodiments, aminoglycoside-lipid conjugates offer improved antibiotic activity over a comparison compound, such as an aminoglycoside antibiotic, in various bacteria. In certain embodiments, an aminoglycoside-lipid$_{C15-C19}$ conjugate offers improved activity over the unmodified aminoglycoside alone, such as with MRSA, MRSE, or P. aeruginosa. In certain embodiments, an aminoglycoside-lipid$_{C5-C11}$ conjugate offers improved activity than the aminoglycoside alone, such as with MRSE, or P. aeruginosa.

Certain particular examples of improvements observed with various hydrophobically enhanced aminoglycosides of the present invention are discussed in the Examples below, and in FIG. 4 and FIG. 6. For example, conjugation of neomycin with $C_{16}$- or $C_{20}$-lipids as described in FIG. 4 results in strong antibacterial activity against MRSA while shorter lipids ($C_6$- or $C_{12}$-) result in reduced antibacterial activity relative to neomycin. This is in contrast to the antibacterial activity against Gram-positive E. coli. For instance, compound 13 bearing a $C_6$-lipid chain displays stronger activity against E. coli and gentamycin-resistant E. coli than the $C_{16}$- or $C_{20}$-lipid conjugates. In case of P. aeruginosa, the inventors observed optimal antimicrobial activity for the $C_{20}$-lipid conjugate 16.

By "improved" in the context of comparing an effect of a hydrophobically enhanced aminoglycoside with that of another compound, it is meant that the effective amount of the hydrophobically enhanced aminoglycoside is lower than the effective amount of the comparison compound (e.g., an unmodified aminoglycoside antibiotic (e.g., neomycin), or an antimicrobial cationic lipid (e.g., dioctadecyldimethylammonium bromide (Vieira and Carmona-Ribeiro, 2006, incorporated herein by reference in its entirety)) when administered under similar conditions. The context of the showing of such improvement may be, for example, that a hydrophobically enhanced aminoglycoside shows improved antibacterial activity in that the amount needed to ameliorate or eliminate side effects of the infection or the infection itself is less than the amount of, for example, an aminoglycoside antibiotic needed to produce these results when administered under similar conditions.

As used herein, an "aminoglycoside" refers a large and diverse class of antibiotics that characteristically contain two or more aminosugars linked by glycosidic bonds to an aminocyclitol component. Examples of aminoglycosides are neomycin, kanamycin, tobramycin, neamine, streptomycin and others. An "aminoglycoside antibiotic" or "AA" refers to a class of aminoglycosides that exhibit concentration-dependent antibacterial activity. See, e.g., Hooper, 1982; Haddad et al., 2001.

In any embodiment of the present invention, an aminoglycoside may be further defined as an aminoglycoside antibiotic. Aminoglycoside antibiotics are well-known in the art, and carry up to six amino groups which are predominantly charged at physiological pH (Sitaram and Nagaraj, 2002; Gordon et al., 1994; Terret et al., 1995; Bunin, 1998; Czarnik and De Witt, 1997). In certain embodiments, an aminoglycoside antibiotic of the present invention is further defined as a neomycin, a kanamycin, paromomycin, amikacin, a gentamicin, netilmycin, a streptomycin, tobramycin, a hygromycin, or a spectinomycin. In certain embodiments, the aminoglycoside antibiotic comprises a primary hydroxy position, such as in a neomycin, a kanamycin, amikacin, a streptomycin, tobramycin or a hygromycin. In particular embodiments, the aminoglycoside antibiotic is further defined as a neomycin or a kanamycin. In certain embodiments, the antibiotic is further defined as not a kanamycin, such as not kanamycin A. In certain embodiments, the antibiotic is further defined as not paromomycin.

An "aminoglycoside-lipid conjugate" is a cationic lipid in which a multiple charged cationic head group (the aminoglycoside) is linked to a lipid moiety, wherein the hydrophobicity of the aminoglycoside-lipid conjugate is greater than the hydrophobicity of the aminoglycoside in the absence of the lipid moiety. In certain embodiments, a hydrophobically enhanced aminoglycoside, such as an aminoglycoside-lipid conjugate, may comprise an aminoglycoside moiety having 3, 4, 5, or 6 or more positive charges, or any range derivable therein. Methods of measuring hydrophobicity are described herein. Non-limiting examples of aminoglycoside-lipid conjugates are compounds 13, 14, 15, 16 and 17, as shown herein.

As used herein, "lipid" or "lipid moiety" (used interchangeably) refers to a straight-chain hydrocarbon radical having 5 carbons or higher, wherein the radical may comprise single, double, and/or triple bonds. In certain embodiments, the straight-chain hydrocarbon radical has between 5 and 45 carbon atoms. In certain embodiments, a lipid may comprise only single bonds. In certain embodiments, a lipid may comprise 20 or fewer double bonds. In certain embodiments, a lipid may comprise at most or at least 19, 18, 17, 16, 15, 14, 13, 12, 11, 10, 9, 8, 7, 6, 5, 4, 3, 2, or 1 double bond(s), or any range derivable therein. In certain embodiments, a lipid may comprise 10 or fewer triple bonds. In certain embodiments, a lipid may comprise at most or at least 9, 8, 7, 6, 5, 4, 3, 2, or 1 triple bond(s), or any range derivable therein. In certain embodiments, a lipid may be of the formula $C_aH_{2a+1}$, wherein a is 5-45. In certain embodiments, a is at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or higher, or any range derivable therein. In certain embodiments, a lipid may be of the formula $C_aH_{2a-x}$, wherein a is as defined above and x is an odd number such that 2a-x≥0. In certain embodiments, a lipid may be of the formula $C_aH_{2a-1}$, wherein a is as described above. In certain embodiments, a lipid may be of the formula $C_aH_{2a-3}$, wherein a is as described above. Non-limiting examples of lipids include —$C_5H_{11}$, —$C_{11}H_{23}$, —$C_{15}H_{31}$, —$C_{19}H_{39}$ and —$C_{17}H_{31}$. An aminoglycoside-lipid conjugate may comprise more than one lipid.

An "aminoglycoside-aryl/heteroaryl conjugate" refers to a cationic lipid in which a multiple charged cationic head group (the aminoglycoside) is linked to a moiety comprising an aryl or heteroaryl group, wherein hydrophobicity of the aminoglycoside-aryl/heteroaryl conjugate is greater than the hydrophobicity of the aminoglycoside in the absence of the moiety comprising the aryl or heteroaryl group. In certain embodiments, the aryl or heteroaryl group may be substituted. Non-limiting examples of moieties comprising an aryl or heteroaryl group include aryl, aralkyl, heteroaryl and heteroaralkyl, as these terms are defined below. In certain embodiments, the aryl/heteroaryl moiety comprises a polycyclic aromatic hydrocarbon (PAH), which is an aryl group that consists of at least two fused unsubstituted aryl rings and does not contain heteroatoms or substituents other than hydrogen. Such an example is pyrene. Other non-limiting examples of aminoglycoside-aryl/heteroaryl conjugates are compounds 18 and 19, described herein.

In particular embodiments regarding aminoglycoside-aryl/heteroaryl conjugates, the aryl/heteroaryl group is a substituted or unsubstituted phenyl group. In particular embodiments, the phenyl group is unsubstituted. In certain embodiments, a phenyl group is monosubstituted. In certain embodiments, a phenyl group is di-, tri-, tetra-, or pentasubstituted. In certain embodiments, a substituent is selected from the group consisting of fluoro, chloro, bromo, iodo, hydroxy, amino, mercapto, alkyl, substituted alkyl, alkoxy, substituted alkoxy, alkylamino, substituted alkylamino, dialkylamino and substituted dialkylamino. In certain embodiments, the substituent(s) on the phenyl group only comprise hydrogen and carbon.

An "aminoglycoside-cholesteroyl conjugate" refers to a cationic lipid in which an aminoglycoside is linked to a moiety comprising a cholesteroyl group, wherein a cholesteroyl group comprises the following structure:

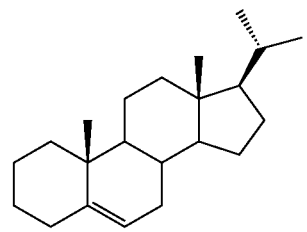

wherein any carbon atom available for bonding (that is, not bound to four other carbon atoms, or not bound to three other carbon atoms in the case of a carbon atom that participates in a double bond) may be used as a point of attachment. The cholesteroyl group may be conjugated to an aminoglycoside through, for example, an alkanediyl group or substituted alkanediyl (each defined below), for example.

An "aminoglycoside-lysine conjugate" is a conjugate wherein the amino group of the side chain of lysine is conjugated at a primary hydroxy position of an aminoglycoside through a —NH— bond. By way of example, compounds 22 and 24 aminoglycoside-lysine conjugates. Conjugates that comprise additional or other amino acids, including peptides, besides the tryptophan seen in 24, are also contemplated: these conjugates may generally be called aminoglycoside-amino acid conjugates. Aminoglycoside-amino acid conjugates are characterized by the joining of the side chain of the amino acid to an aminoglycoside through an —NH— bond at a primary hydroxy position of the aminoglycoside. The amino acid may be comprised in a peptide, such that the entity may be called an aminoglycoside-peptide conjugate. More than one amino acid in such a peptide may be conjugated to an aminoglycoside. Amino acids comprising an amino group at the α, β, γ, δ, or higher position in the amino acid side chain may be employed, for example. In addition to lysine, then, non-liming examples of amino acids that may be conjugated to an aminoglycoside include ornithine and diaminobutyric acid. Other non-limiting examples of peptides that may be employed are described herein. The peptides made from these or other amino acids may be α, β, γ, δ, or higher peptides, and may comprise mixtures as well as D- and L-variants. The peptides may be linear, cyclic, or depsipeptides that may or may not comprise a lactone ring.

It is specifically contemplated that for any embodiment that employs a hydrophobically enhanced aminoglycoside, an aminoglycoside-lipid conjugate, an aminoglycoside-aryl/heteroaryl moiety conjugate, an aminoglycoside-lysine conjugate or other aminoglycoside-amino acid conjugate, an aminoglycoside-peptide conjugate, and/or an aminoglycoside-cholesteroyl conjugate may be alternatively or additionally used, unless specifically noted otherwise. For example, each of these conjugates may be used in any method of treatment or pharmaceutical composition described herein, in any combination. The term "hydrophobe," as used herein (e.g., an aminoglycoside-hydrophobe conjugate), refers to the -lipid, -aryl/heteroaryl, -lysine or other amino acid or peptide and -cholesteroyl moieties as described above, or any combination thereof. In certain embodiments, a hydrophobe refers to a -lipid or a substituted or unsubstituted phenyl group.

Moreover, it is specifically contemplated that definitions or descriptions of compounds may be further defined to exclude any compound or class of compounds discussed herein.

As used herein, "a primary hydroxy position of the aminoglycoside" refers to an aminoglycoside that comprises a primary hydroxy group, such that that position is the "primary hydroxy position." The phrases regarding "a secondary hydroxy group of an aminoglycoside," "a primary amino group of an aminoglycoside" and "a secondary amino group of an aminoglycoside" may be interpreted similarly. For example, kanamycin A, as that compound is known in the art, contains only one primary hydroxy group, only one primary amino group, and several secondary hydroxy and amino groups. Accordingly, kanamyin A contains only one primary hydroxy position, only one primary amino position, and contains several secondary hydroxy and amino positions. As another example, neomycin B contains only one primary hydroxy group, only two primary amino groups, and several secondary hydroxy and amino groups. Accordingly, neomycin B contains only one primary hydroxy position, only two primary amino positions, and several secondary hydroxy and amino positions. Moreover, an aminoglycoside antibiotic may be modified to contain a primary or secondary hydroxy or amino group, such as by methods described herein. When a moiety is bound to an aminoglycoside at, e.g., "a primary hydroxy position of the aminoglycoside," it means that the primary hydroxy group has been modified such that the moiety is now bound at that primary hydroxy position. The same reasoning may be applied to moieties bound to secondary hydroxy positions, primary amino positions, and secondary amino positions.

As used herein, "conjugation" and "conjugate" refer to covalent bonds between entities, unless specifically noted otherwise.

As used herein, the words "link," "linkage," "linker," or "bound" refer to covalent binding between species, unless specifically noted otherwise. An "amide linker" refers to the following connection: —NHC(O)-lipid. An "aminoacyl linker" refers to —C(O)NH-lipid. An "ester linker" refers to —OC(O)-lipid. An "oxyacyl linker" refers to —C(O)O-lipid. A "thioester linker" refers to —OC(S)-lipid. An "oxythioacyl linker" refers to —C(S)O-lipid. A "carbamate linker" refers to aminoglycoside-NHC(O)O-lipid. A "urea linker" refers to aminoglycoside-NHC(O)NH-lipid. A "thiourea linker" refers to aminoglycoside-NHC(S)NH-lipid. An "ether linker" refers to —O—. A "carbonate linker" refers to —OC(O)O—. An "amino linker" refers to —NH-lipid. Any of these linkers may be used with any hydrophobically enhanced aminoglycoside described herein, unless specifically noted otherwise. It is further noted that "through a linker" is to mean through that linker alone and no other atoms are comprised in the linker. In certain embodiments, a connection between an aminoglycoside and a lipid "comprises" any of these linkers—this means that other atoms may be found in the linkage. For example, the following linker comprises an amide linker: —NHC(O)—CH(CH$_3$)-lipid.

The term "alkyl" when used without the "substituted" modifier refers to a non-aromatic monovalent group, having a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "aryl" when used without the "substituted" modifier refers to a monovalent group, having an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group, having an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group, having an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group, having an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "alkanediyl" when used without the "substituted" modifier refers to a non-aromatic divalent group, wherein the alkanediyl group is attached with two 6-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

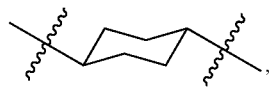 [SMILES: *C1CCC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$^2$—, —CH(Cl)—, —CH(OH)—, —CH(OCH$_3$)—, and —CH$_2$CH(Cl)—.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl, having two or more saturated carbon atoms, at least two of which are attached to the nitrogen atom.

As used herein, an "amino acid" refers to any of the 20 naturally occurring amino acids found in proteins, as well as synthetic analogs (e.g., D-stereoisomers of the naturally occurring amino acids, such as D-threonine). α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Protected amino acids are also contemplated, such as when an N-terminus, C-terminus, and/or functional group of a side chain is protected by a protecting group.

Unnatural amino acids (that is, those that are not naturally found in proteins) are also known in the art, as set forth in, for example, Williams (1989); Evans et al. (1990); Pu et al. (1991); Williams et at (1991); and all references cited therein, each of which is incorporated herein by reference. The present invention thus includes unnatural amino acids and their side chains as well. $\beta$- and $\gamma$-Amino acids are known in the art and are also contemplated by the present invention. Non-limiting examples of unnatural amino acids include ornithine, diaminobutyric acid and others. The following table shows non-limiting examples of unnatural amino acids that are contemplated by the present invention.

| Modified and Unusual Amino Acids | | | |
|---|---|---|---|
| Abbr. | Amino Acid | Abbr. | Amino Acid |
| Aad | 2-Aminoadipic acid | EtAsn | N-Ethylasparagine |
| Baad | 3-Aminoadipic acid | Hyl | Hydroxylysine |
| Bala | $\beta$-alanine, $\beta$-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Moreover, an "amino acid" refers to both an amino acid, alone (e.g., glycine), or an amino acid residue (e.g., glycyl). When two or more amino acids combine to form a peptide and the elements of water are removed, what remains of each amino acid may be called an "amino acid residue." Amino-acid residues are structures that lack a hydrogen atom of the amino group (—NH—CHR—COOH), or the hydroxyl moiety of the carboxyl group (NH$_2$—CHR—CO—), or both (—NH—CHR—CO—); all units of a peptide chain are therefore amino acid residues. Amino acids may terminate in —COOH, —COO(R), wherein R is a carboxylic acid protecting group, —C(O)NHR$_1$, or —NHR$_2$, wherein R$_1$ and R$_2$ are each independently H or an amino protecting group.

As used herein, a "peptide" refers to two or more amino acids joined together by an amide bond. Peptides may terminate in any fashion described above regarding amino acids. "Short" peptides refer to di-, tri- and tetra-peptides. In certain embodiments, peptides comprise up to or include 50 amino acids. Peptides may be linear or cyclic, or of the depsipeptide form that may or may not comprise a lactone moiety. Peptides may be $\alpha$, $\beta$, $\gamma$, $\delta$, or higher, or mixed. Indeed, peptides may comprise any mixture of amino acids as defined herein, such as comprising any combination of D, L, $\alpha$, $\beta$, $\gamma$, $\delta$ or higher amino acids.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups, including examples of their installation and removal, may be found in Greene and Wuts, 1999, incorporated herein by reference in its entirety. Aminoglycoside-lipid conjugates and other hydrophobically enhanced aminoglycosides described herein are contemplated as protected by one or more protecting groups—that is, the present invention contemplates such conjugates in their "protected form," wherein at least one functional group is protected by a protecting group. Non-limiting examples of carboxylic acid protecting groups include benzyl (Bn) and t-butyl. Non-limiting examples of amino protecting groups include Bn, carbobenzyloxy (Cbz), t-butoxycarbonyl (Boc) and 9-fluorenylmethyloxycarbonyl (Fmoc), for example.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S— or the R-configuration, as defined by the IUPAC 1974 Recommendations. In certain aspects, certain compounds of the present invention may comprise S- or R-configurations at particular carbon centers.

Synthetic techniques that may be used to prepare certain compounds of the present invention are provided in the Examples section. These techniques may be expanded to produce other hydrophobically enhanced aminoglycosides using techniques known in the art. Other synthetic techniques to prepare compounds of the present invention, such as precursors, as well as derivatives are well-known to those of skill in the art. For example, Smith and March, 2001 discuss a wide variety of synthetic transformations, reaction conditions, and possible pitfalls relating thereto, including amidation and esterification reactions. Methods of oxidizing a primary hydroxy position of an aminoglycoside such that is may be further reacted to produce a hydrophobically enhanced aminoglycoside are discussed in, for example, Kudyba et al., 2007, which is incorporated herein by reference in its entirety. Methods discussed therein may be adapted to prepare compounds of the present invention from commerically available starting materials.

Solvent choices for preparing hydrophobically enhanced aminoglycosides of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention.

One of ordinary skill in the art will understand that compounds of the present invention can generally be purified at any step, including the purification of intermediates as well as purification of the final products. In certain embodiments, purification is performed via silica gel column chromatography or HPLC.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art, such as methods described herein.

In certain aspects, "derivative" refers to a chemically-modified compound that still retains the desired effects of the compound prior to the chemical modification. Using an aminoglycoside-lipid conjugate as an example, an "aminoglycoside-lipid conjugate derivative" refers to a chemically modified aminoglycoside-lipid conjugate that still retains the desired effects of the parent aminoglycoside-lipid conjugate prior to its chemical modification. Such effects may be enhanced (e.g., slightly more effective, twice as effective, etc.) or diminished (e.g., slightly less effective, 2-fold less effective, etc.) relative to the parent aminoglycoside-lipid conjugate, but may still be considered an aminoglycoside-lipid derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl, or substitution of a phenyl by a larger or smaller aromatic group. Alternatively, in a cyclic or bicyclic structure, heteroatoms such as N, S, or O can be substituted into the structure instead of a carbon atom.

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. Pharmaceutically acceptable salts are also contemplated.

"Pharmaceutically acceptable salts" means salts of compounds of the present invention which are pharmaceutically acceptable, as defined above, and which possess the desired pharmacological activity. Compounds of the present invention are contemplated in their pharmaceutically acceptable salt forms. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prodrug" means a compound that is convertible in vivo metabolically into an aminoglycoside-lipid conjugate, according to the present invention. Such prodrugs of hydrophobically enhanced aminoglycosides are contemplated by the present invention. The prodrug itself may or may not also have activity with respect to a given target. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyl-tartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

Hydrates of compounds of the present invention are also contemplated. The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The terms "inhibiting" or "reducing" or any variation of these terms, when used in the claims and/or the specification, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of bacterial infection following administration of a aminoglycoside-lipid conjugate of the present invention. In a further example, following administering of a aminoglycoside-lipid of the present invention, a patient suffering from a bacterial infection may experience a reduction the number and/or intensity of symptoms of the infection. Non-limiting examples of typical symptoms associated with a bacterial infection include elevated temperature, sweating, chills, and/or excess white blood cells compared to a normal range.

The term "effective," as that term is used in the specification and/or claims, means adequate to accomplish a desired, expected, or intended result. Hydrophobically enhanced aminoglycosides, such as aminoglycoside-lipid conjugates, may be employed in an effective amount in any embodiment herein.

"Therapeutically effective amount" means that amount which, when administered to an animal for treating a disease, condition, or infection, is sufficient to effect such treatment for the disease, condition, or infection. Hydrophobically enhanced aminoglycosides, such as aminoglycoside-lipid conjugates, may be employed in any embodiment herein.

"Treatment" or "treating" includes (1) inhibiting a disease, condition, or infection in a subject or patient experiencing or displaying the pathology or symptomatology of the disease, condition, or infection (e.g., arresting further development of the pathology and/or symptomatology), (2) ameliorating a disease, condition, or infection in a subject or patient that is experiencing or displaying the pathology or symptomatology of the disease, condition, or infection (e.g., reversing the pathology and/or symptomatology), and/or (3) effecting any measurable decrease in a disease, condition, or infection in a subject or patient that is experiencing or displaying the pathology or symptomatology of the disease, condition, or infection. Hydrophobically enhanced aminoglycosides, such as aminoglycoside-lipid conjugates, may be employed for treatment purposes in any embodiment herein, such as treatment of a bacterial infection.

"Prevention" or "preventing" includes: (1) inhibiting the onset of a disease, condition, or infection in a subject or patient which may be at risk and/or predisposed to the disease, condition, or infection but does not yet experience or display any or all of the pathology or symptomatology of the disease, condition, or infection, and/or (2) slowing the onset of the pathology or symptomatology of a disease, condition, or infection in a subject or patient which may be at risk and/or predisposed to the disease, condition, or infection but does not yet experience or display any or all of the pathology or symptomatology of the disease, condition, or infection. Hydrophobically enhanced aminoglycosides, such as aminoglycoside-lipid conjugates, may be employed for preventive purposes in any embodiment herein, such as prevention of a bacterial infection.

As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses.

As used herein, a "multidrug resistant (MDR) bacteria" is resistant to two or more antimicrobial classes. For example, MDRTB (tuberculosis) is used to describe strains that are resistant to two or more of the five first-line anti-TB drugs (isoniazid, rifampin, pyrizinamide, ethambutol and streptomycin).

It is contemplated that any embodiment discussed in this specification can be implemented with respect to any method, compound, or composition of the invention, and vice versa. Furthermore, compounds and compositions of the invention can be used to achieve methods of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 4 Table 1, showing representative minimal inhibitory concentrations (MIC) in μg/mL for various bacterial strains and various aminoglycoside-lipid conjugates: [a]ATCC 29213; [b]methicillin-resistant *S. aureus* (ATCC 33592); [e]ATCC 1490; [d]methicillin-resistant *S. epidermidis* (ATCC 14990); [e]ATCC 49619; [f]ATCC 25922; [g]ATCC 6174 (gentamicin resistant); [h]ATCC 27853.

FIG. 6 Table 2, showing representative minimal inhibitory concentrations (MIC) in μg/mL for various bacterial strains and various aminoglycoside-lipid conjugates: [a]ATCC 29213; [b]methicillin-resistant *S. aureus* (ATCC 33592); [e]ATCC 1490; [d]methicillin-resistant *S. epidermidis* (ATCC 14990); [e]ATCC 49619; [f]ATCC 25922; [g]ATCC 6174 (gentamicin resistant); [h]ATCC 27853.

FIG. 17 Table 3: Antibacterial activity minimal inhibitory concentration (MIC) in µg/ml.

DESCRIPTION OF THE ILLUSTRATIVE EMBODIMENTS

I. Aminoglycoside Antibiotic Resistance

Figure 1:
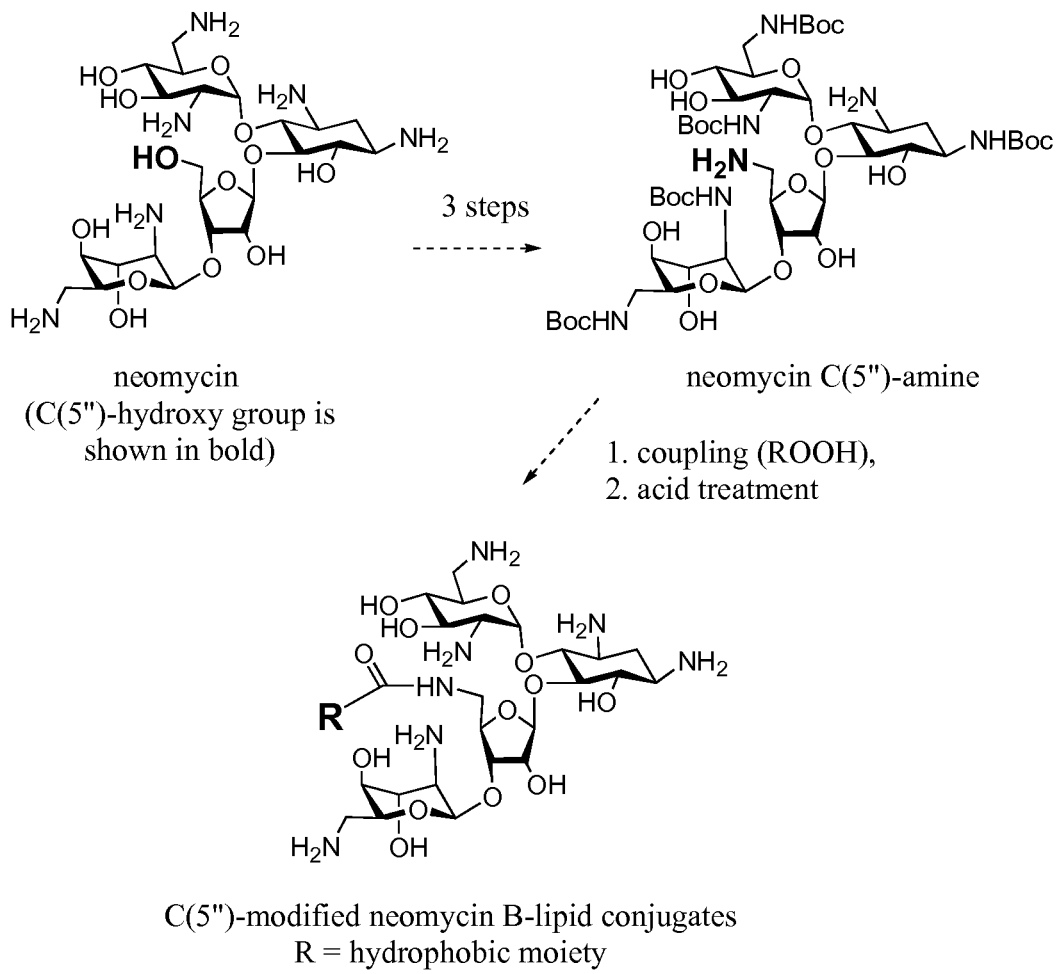
FIG. 1 A non-limiting synthetic strategy for the synthesis of certain C(5″) neomycin B-lipid conjugates.

There are three general mechanisms of aminoglycoside antibiotic-resistance: (1) reduction of the intracellular concentration of the antibiotic within bacterial cells, usually via efflux of the agent out of the bacterial cell by either dedicated or general efflux pumps or other mechanisms; (2) alteration of the molecular target of the antibiotic, usually as result of a spontaneous mutation in the gene encoding the target or substitution of the target's function by an exogenous gene; and (3) enzymatic inactivation of the aminoglycoside (Neu, 1992; Hayes and Wolf, 1990; Jacoby et al., 1991). The rapid emergence of aminoglycoside antibiotic-resistant strains has instigated research efforts to develop novel aminoglycoside antibiotics or modified aminoglycoside antibiotic-analogs that can delay or avoid acquired resistance by pathogenic bacteria. However, progress has been slow due to the fact that novel and purely synthetic aminoglycoside antibiotics are difficult to synthesize and structural modifications on naturally occurring aminoglycoside antibiotics usually require complex multi-step organic synthesis.

Most of the naturally occurring aminoglycoside antibiotics are structurally characterized by amino sugars glycosidically linked to an aminocyclitol which, in most cases, is 2-deoxystreptamine. Several types of 2-deoxy-streptamine derivatives exist: monosubstituted derivatives such as neamine, 4,5-disubstituted (neomycin type derivatives), and 4,6-disubstituted (kanamycin, tobramycin and gentamycin) derivatives. aminoglycoside antibiotics carry up to six amino groups which are predominantly charged at physiological pH (Dorman et al., 1976; Botto and Coxon, 1983) and bind with high affinity to anions and nucleic acids via electrostatic and hydrogen bonding interactions (Ohyama et al., 1998; Chen et al., 1997; Wang and Tor, 1997; Constantinou-Kokotou et al., 2001). Aminoglycoside antibiotics are considered to be non-specific RNA binders that recognize numerous three-dimensional RNA structures including group I introns (Von Ahsen and Noller, 1993), hammerhead ribozymes (Clouet-d'Orval et al., 1995), the HIV-1's TAR (Mei et al., 1995) and RRE (Werstuck et al., 1996; Kirk et al., 2000) regulatory domains. In order to exhibit their antibacterial activity, aminoglycoside antibiotics must bind to the RNA receptor located within the cell. This requires uptake of the aminoglycoside antibiotic by the bacterial cell. However, aminoglycoside antibiotic-resistance may be manifested by reduced drug uptake as a result of activation of drug efflux pumps, modified membrane potential, changes in membrane composition and other factors (Taber et al., 1987).

The hydrophobically enhanced aminoglycosides of the present invention offer improved potencies over previously employed aminoglycoside antibiotics. Without being bound by theory, the inventors posit that the activity of the hydrophobically enhanced aminoglycosides may be ascribed to, for example, improved uptake, changes in mode of action, and/or enhanced affinity to RNA. These aminoglycosides may be used to treat bacterial infections, such as infections that show resistance to treatment by other methods.

II. Pharmaceutical Formulations and Administration

Pharmaceutical compositions of the present invention comprise an effective amount of one or more candidate substances (e.g., an aminoglycoside-lipid conjugate or any other hydrophobically enhanced aminoglycoside) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient, such as a pharmaceutically acceptable carrier, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present invention may be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. In certain embodiments, intramuscular, intravenous, topical administration, or inhalation administration is contemplated. Pharmaceutical compositions comprising a compound of the present invention are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of an aminoglycoside-lipid conjugate or any other hydrophobically enhanced aminoglycoside described herein.

The actual dosage amount of a an aminoglycoside-lipid conjugate or any other hydrophobically enhanced aminoglycoside described herein administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject. Compounds of the present invention may, in certain embodiments, be cleared by the kidneys: thus, it may, in certain embodiments, be important to assess any underlying problems with kidney function. Kidney function may be assessed by measuring the blood levels of creatinine, a protein normally found in the body. If these levels are higher than normal, it is an indication that the kidneys may not be functioning at an optimal rate and dosage may be lowered accordingly The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intra-operative or post-operative.

In certain embodiments, pharmaceutical compositions may comprise, for example, at least about 0.1% of an aminoglycoside-lipid conjugate or any other hydrophobically enhanced aminoglycoside described herein. In other embodiments, an aminoglycoside-lipid conjugate or any other hydrophobically enhanced aminoglycoside described herein may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The aminoglycoside-lipid conjugate or any other hydrophobically enhanced aminoglycoside described herein may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

III. Combination Therapy

In order to enhance or increase the effectiveness of an aminoglycoside-lipid conjugate or any other hydrophobically enhanced aminoglycoside described herein, the conjugate may be combined with another therapy, such as another agent that combats and/or prevents bacterial infection. For example, aminoglycoside-lipid conjugates of the present invention may be provided in a combined amount with an effective amount of an anti-bacterial agent (that is, an antibiotic). Anti-bacterial classes and agents are well-known in the art, and include, for example, the classes of aminoglycoside antibiotics, cephalosporins, penicillins, quinolones, sulfonamides, tetracyclines, beta-lactams and macrolides. Non-limiting specific examples of antibacterial agents include linezolid, tigecycline, tetracycline, oxytetracycline, doxycycline, minocycline, vancomycin, enrofloxacin, erythromycin, tyrocidine, griseofulvin, streptomycin, polymyxin, cephalosporin, ampicillin, cephalothin, lincomycin, gentamicin, carbenicillin, cephalexin and clindamycin. These lists of antibiotics are not exhaustive and one skilled in the art can readily determine other antibiotics which may be employed.

An aminoglycoside-lipid conjugate or any other hydrophobically enhanced aminoglycoside described herein may be combined with, for example, a lipid bilayer permeabilizing agent, such as an ionic lipid or other such agent known in the art. See, e.g., Shelburne et al., 2004.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein an aminoglycoside-lipid conjugate or any other hydrophobically enhanced aminoglycoside described herein is "A" and a second agent, such as an antibacterial agent, is "B":

A/B/A B/A/B B/B/A A/A/B A/B/B B/A/A A/B/B/B B/A/ B/B B/B/B/A B/B/A/B A/A/B/B A/B/A/B A/B/B/A B/B/A/A B/A/B/A B/A/A/B A/A/A/B B/A/A/A A/B/ A/A A/A/B/A

IV. Examples

The following examples are included to demonstrate particular embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Figure 2:
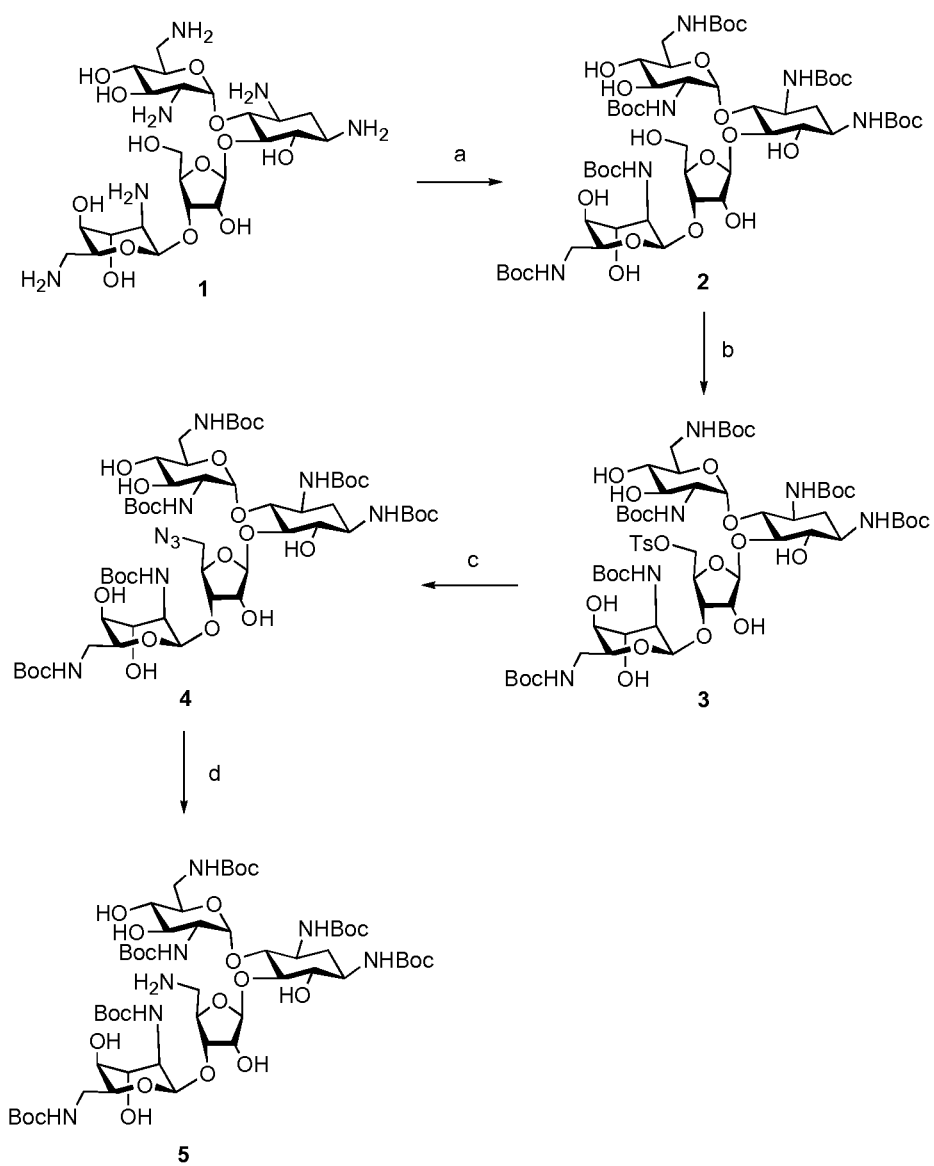
FIG. 2 Scheme 1: Conversion of the C(5″)-hydroxy group of neomycin to an amino group. Reagents and conditions: (a) (Boc)$_2$O, Et$_3$N, DMF-H$_2$O, 80° C., 6 h, 74%; (b) TsCl, Py, rt, 10 h, 81%; (c) NaN$_3$, DMF, 60° C., 8 h, 53%; (d) Pd(OH)$_2$/C, H$_2$, rt, 5 h, 85%.

Synthetic Preparation of Certain Neomycin-Lipid Conjugates of the Present Invention Readily available neomycin sulfate was converted into salt free neomycin 1 via ionic exchange. The amino functions were protected as carbamate 2 by treatment with (BOC)$_2$O in DMF-water mixture as previously described (Michael et al., 1999; Kirk et al., 2000). The primary hydroxyl group at the C5"-position was selectively tosylated by treatment of 2 with p-toluenesulfonyl chloride in neat pyridine affording monotosylated compound 3 in 81% yield (Scheme 1, FIG. 2). Nucleophilic displacement of tosyl-derivative 3 using sodium azide in DMF at 80° C. produced azide 4 (Disney and Barrett, 2007) which was subjected to catalytic hydrogenation using Pearlman's catalyst (Pd(OH)$_2$/H$_2$/C) to provide partially protected 5"-NH$_2$ neomycin analog 5 (Scheme 1, FIG. 2).

Figure 3:
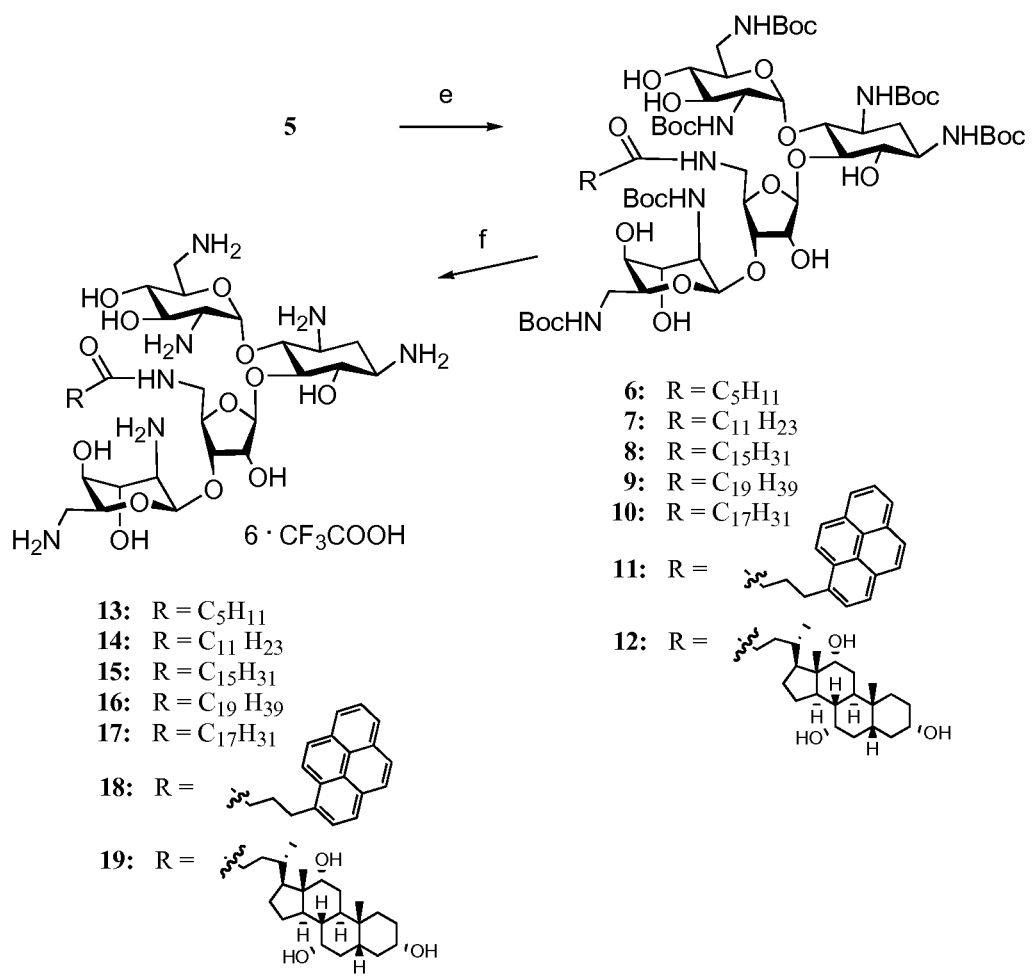
FIG. 3 Scheme 2: Preparation of certain aminoglycoside-lipid conjugates of the present invention. Reagents and conditions: (e) TBTU, DMF, DIPEA, rt, 2 h, 85%-92%, lipophilic acid, (RCOOH, R=hexanoic acid, dodecanoic acid, palmitic acid, arachidic acid, linoleic acid, pyrene butyric acid, cholic acid); (f) TFA, CH$_2$Cl$_2$, 0° C., 3 min, 90%.

Amine 5 served as a precursor for conjugation to lipophilic acids (Scheme 2, FIG. 3). The inventors selected a variety of acids including saturated C$_6$-, C$_{12}$-, C$_{16}$- and C$_{20}$-, a double unsaturated C$_{18}$-acids and other acids containing pyrene and cholic acid in order to study how chain length, saturation and hybridization of the lipophilic moiety affects the antimicrobial activity. The lipophilic acids were coupled to neomycin-based amine 5 by exposure to 2-(1H-benzotriazole-1yl)-1,1, 3,3-tetra-methyluronium tetrafluoroborate (TBTU) as coupling reagent and Hünigs base in DMF to yield the lipid conjugates 6-12 (Scheme 2, FIG. 3). Exposure of the conjugates 6-12 to 95% TFA provided the deblocked neomycin-lipid conjugates 13-19 as TFA salts which were used in the bacterial assays against Gram-positive and Gram-negative organisms.

Figure 7:
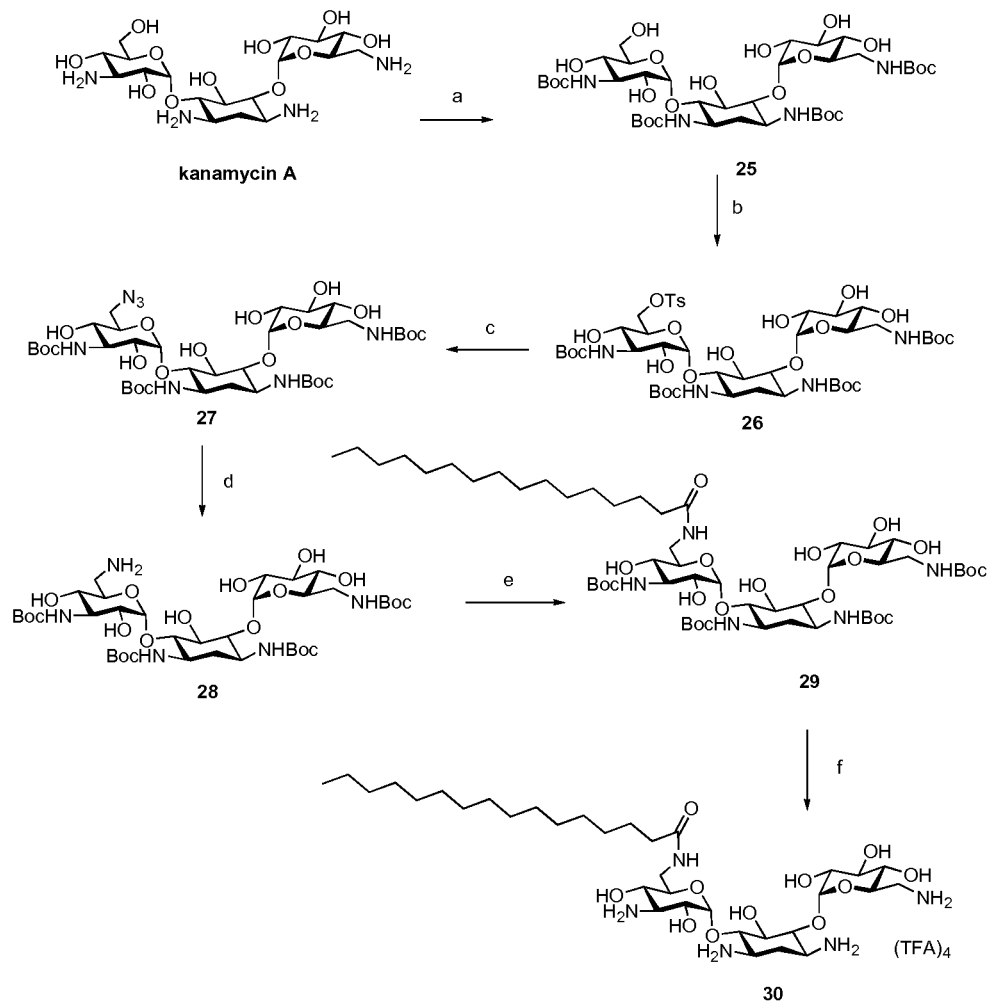
FIG. 7 Scheme 4: Synthesis of kanamycin A-lipid conjugates. Reagents and conditions: (a) (Boc)$_2$O, Et$_3$N, DMF-H$_2$O, 80° C., 6 h, 74%; (b) TsCl, Py, rt, 10 h, 81%; (c) NaN$_3$, DMF, 60° C., 8 h, 53%; (d) Pd(OH)$_2$/C, H$_2$, rt, 5 h, 85%; (e) TBTU, C$_{15}$H$_{31}$COOH, DIEA, DMF, TFA.
Figure 8:
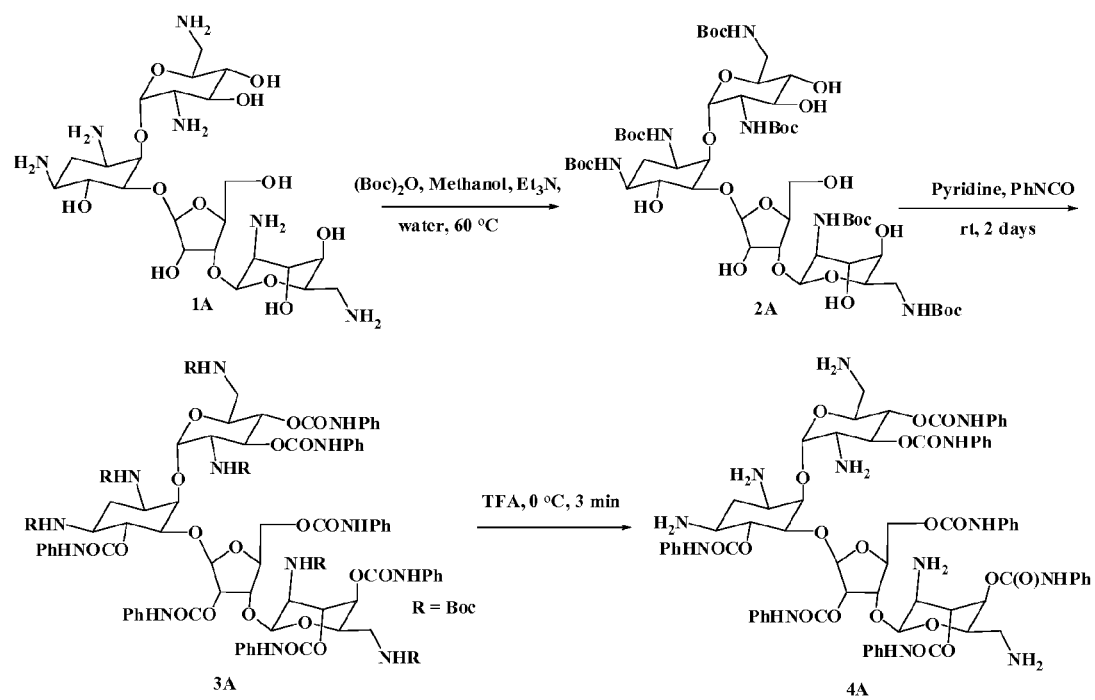
FIG. 8 Scheme 5: Synthesis of neomycin B-based polycationic phenyl carbamate 4A.
Figure 9:
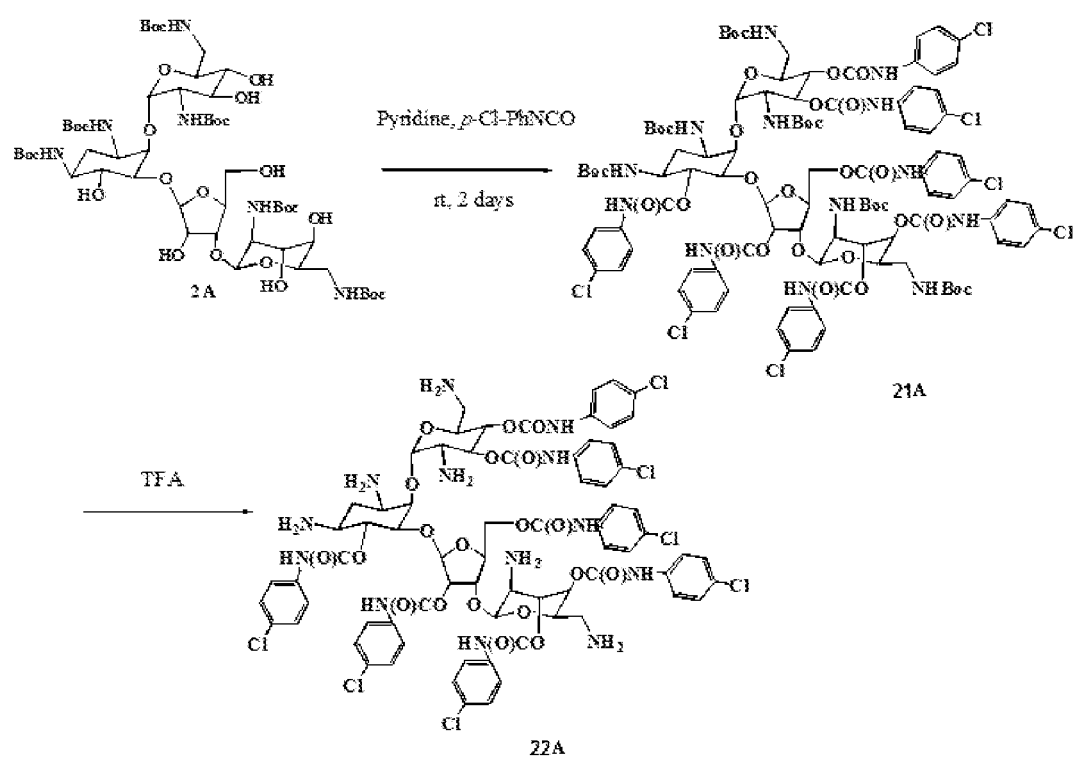
FIG. 9 Scheme 6: Synthesis of neomycin B-based polycationic p-chlorophenyl carbamate 22A.

The same strategy was used to prepare kanamycin A-lipid conjugate 30 (Scheme 4, FIG. 7). The single hydroxyl group in Boc-protected kanamycin A (25) was converted into azide 27 by selective activation as sulfonate ester 26 and nucleophilic substitution with sodium azide as previously described by Quader et al., 2007. Reduction of the azide 27 by catalytic hydrogenation provided amine 28 which was condensed to a hydrophobic acid like hexadecanoic acid afforded amide 29. Deblocking with TFA produced unprotected cationic lipid 30.

Example 2

Characterization Data and Additional Synthetic Methods Regarding Certain Hydrophobically Enhanced Aminoglycoside Antibiotics Methods NMR spectra were recorded on a Brucker Avance 300 spectrometer (300 MHz for $^1$H NMR, 75 MHz for $^{13}$C). Optical rotation was measured with a Perkin-Elmer polarimeter (accuracy 0.002°). GC-MS analyses were performed on a Perkin-Elmer Turbomass—Autosystem XL; alternatively, mass spectra were recorded on a Linear Ion trap (LTQ)-Thermo-Finnigan spectrometer. Analytical thin-layer chromatography was performed on precoated silica gel plates. Visualization was performed by ultraviolet light and/or by staining with ninhydrin solution in ethanol. Chromatographic separations were performed on a silica gel column by flash chromatography (Kiesel gel 40, 0.040-0.063 mm; Merck). Yields are given after purification, unless differently stated. When reactions were performed under anhydrous conditions, the mixtures were maintained under nitrogen.

Characterizations and Additional Methods 1,3,2',6',2''',6''-Hexa-N-(tert-butoxycarbonyl)-5"-O-(p-methyl benzene-sulfonyl)-neomycin (3)

To a stirred solution of 2 (4.0 g, 3.29 mmol) prepared according to procedure by Michael et al., 1999 in dry pyridine (75 mL) was added TsCl (3.8 g, 19.74 mmol) at 0° C. The reaction mixture was stirred at room temperature for 10 h. The solvent was evaporated under reduced pressure. The reaction mixture was partitioned between EtOAc and water. The organic layer was dried over MgSO$_4$, filtered, and the solvents were evaporated in vacuo. Flash column chromatography afforded product 3 as a white solid (3.7 g, 81%). R$_f$ 0.50 (MeOH/CH$_2$Cl$_2$ 1:23); $^1$H NMR (300 MHz, CD$_3$OD): δ 7.90 (d, 2H, J=7.9 Hz, aromatic), 7.54 (d, 2H, J=7.9 Hz, aromatic), 5.84 (br s, 1H, anomeric), 5.18 (br s, 1H, anomeric), 4.90 (s, 1H, anomeric), 2.48 (s, 3H, Me-OTs); EIMS: calcd for C$_{60}$H$_{101}$N$_6$O$_{27}$S$^+$ 1369.64. Found 1369.34 [M+H]$^+$.

5"-Azido-1,3,2',6',2''',6'''-hexa-N-(tert-butoxycarbonyl)-5"-deoxy-neomycin (4)

Sodium azide (189 mg, 2.92 mmol) was added to a solution of 3 (400 mg, 0.292 mmol) in DMF (10 mL) and the mixture was stirred at 80° C. for 8 h. After cooling to room temperature the reaction mixture was then diluted with ethyl acetate (50 mL) and washed with water (2×50 mL). The ethyl acetate layer was dried (Na$_2$SO$_4$), concentrated in vacuo, and purified by flash chromatography yielding 6 as a white amorphous solid (192 mg, 53%); R$_f$ 0.50 (MeOH/CH$_2$Cl$_2$ 1:20); IR (KBr disk) 2105.8 cm$^{-1}$ (N$_3$); $^1$H NMR (300 MHz, CD$_3$OD): δ 5.47 (br s, 1H, anomeric), 5.16 (s, 1H, anomeric), 4.92 (s, 1H, anomeric), 4.53 (s, 1H), 4.33 (t, 1H, J=4.3 Hz), 4.28 (m, 1H), 4.03 (m, 1H), 3.92 (m, 2H), 3.76 (m, 3H), 3.56 (m, 5H), 3.38 (m, 3H), 3.32 (m, 3H), 3.21 (m, 2H), 1.98 (m, 1H), 1.67 (m, 1H), 1.46 (s, 54H); $^{13}$C NMR (75 MHz, CD$_3$OD): δ 159.0, 158.8, 158.4, 158.2, 158.1, 157.8, 111.6 (anomeric), 100.2 (anomeric), 98.7 (anomeric), 87.3, 80.9, 80.8, 80.5, 80.4, 79.8, 79.0, 78.5, 75.5, 75.2, 74.6, 73.4, 73.1, 72.9, 71.6, 69.1, 56.7, 53.7, 53.5, 52.5, 52.4, 51.4, 51.2, 42.7, 41.9, 35.5, 29.0, 28.9; $[\alpha]_D^{25}=+45.6$ (c 0.5, MeOH); EIMS: calcd for $C_{53}H_{93}N_9NaO_{24}^+$ 1262.62. Found: 1262.62 (M+Na)⁺.

5″-Amino-1,3,2′,6′,2‴,6‴-hexa-N-(tert-butoxycarbonyl)-5″-deoxy-neomycin (5)

The solution of neomycin azide (130 mg, 0.104 mmol) and 10% Pd(OH)₂/C in methanol (5 mL) was hydrogenated at normal temperature and pressure for 5 h and then filtered through celite. Filtrate was concentrated and the residue was purified on flush column chromatography by using MeOH/CH₂Cl₂ (1:9) to afford 19 (108 mg, 85%), as a white solid. ¹H NMR (300 MHz, acetone-d₆): δ 5.18 (m, 1H, anomeric), 5.15 (br s, 1H, anomeric), 5.03 (d, 1H, anomeric, J=2.7 Hz), 4.96 (br s, 1H), 4.28 (d, 1H, J=7.7 Hz), 4.16 (br s, 1H), 4.01 (m, 2H), 3.91 (t, 1H, J=5.4 Hz), 3.83 (m, 2H), 3.75 (m, 2H), 3.70 (m, 1H), 3.56 (m, 6H), 3.44 (m, 4H), 3.19 (m, 2H), 3.04 (m, 1H), 1.62 (m, 1H), 1.54 (m, 1H), 1.41 (3 s, 54H); ¹³C NMR (75 MHz, acetone-d₆): δ 158.1, 157.5, 156.8, 156.7, 156.3, 154.3, 110.8 (anomeric), 100.2 (anomeric), 99.7 (anomeric), 87.8, 80.9, 80.1, 79.8, 79.7, 79.3, 79.1, 78.9, 78.8, 75.1, 74.7, 73.7, 73.3, 72.9, 72.7, 70.8, 68.0, 57.3, 53.1, 51.9, 44.6, 42.7, 41.0, 35.7, 28.9, 28.7, 28.6; $[\alpha]_D^{25}=+32.0$ (c 0.15, MeOH); EIMS: calcd for $C_{53}H_{96}N_7O_{24}$ 1214.65. Found: 1214.33 [M+H]⁺.

General procedure for the coupling reaction. To a solution of neomycin amine 5 (1 eq.) in dry DMF, TBTU (2 equiv), lipidic acid (1 eq) and DIPEA (3 equiv) were added and stirred at room temperature for 2 h. The reaction mixture was triturated with water and ethylacetate. The ethylacetate layer was washed with water, brine, dried over sodium sulfate and concentrated. The crude residue was purified using flash silica gel by eluting with CH₂Cl₂/MeOH. The spectroscopic data were given below.

General procedure for final deprotection. All BOC-protected lipids were treated with 95% TFA at 0° C. for 3 min. TFA was removed at reduced pressure. To the residue 2% methanol in ether was added and the solvent was decanted to get the solid neomycin-lipid conjugate as salt. The spectroscopic data are given below.

Procedure for Reductive Amination of Aminoglycoside-Based Aldehyde 20 with Amines.

5″-N-(Fmoc-Lysine-O-Bn)-1,3,2′,6′,2‴,6‴-hexa-N-(tert-butoxycarbonyl)-5″-deoxy-neomycin (21)

A 0.05 M solution of alcohol 2 (1.0 g, 0.823 mmol) in EtOAc at −10° C. was treated with trichloroisocyanuric acid (TCCA; 0.209 g, 0.902 mmol) and a catalytic amount of TEMPO (0.006 g, 0.041 mmol) under N₂, allowed to warm to 25° C. and stirred for 1 h. After completion the reaction mixture was basified with 1 N NaOH. After separation of the phases, the aq layer was extracted with EtOAc (3×50 mL). The combined org. layers were dried (NaSO₄) and evaporated to get the aldehyde 20. This crude aldehyde was used for next reaction.

To a solution of 20 (0.08 g, 0.065 mmol) in MeOH (10 mL) was added lysine benzyl ester (0.060 g, 0.132 mmol) and stirred at room temperature for 1 h and then AcOH (0.36 mL) was added and the mixture was stirred for 30 min. NaBH₃CN (0.045 g, 0.72 mmol) was then added and the mixture was stirred at room temperature for 4 h. The reaction mixture was neutralized with NaOH and extracted with AcOEt (3×50 mL). The combined organic layers were washed with sat. NaCl (3×30 mL), dried over Na₂SO₄, and filtered, and the solvents were evaporated in vacuo to give an oily residue. Flash column chromatography afforded the desired product 21 as a white solid (0.51 g, 47%).

Spectroscopic Data for Coupled Products.

5″-N-(Hexanoyl)-1,3,2′,6′,2‴,6‴-hexa-N-(tert-butoxycarbonyl)-5″-deoxy-neomycin (6)

Yield=89%; $R_f$ 0.50 (MeOH/CH₂Cl₂ 1:12); ¹H NMR (300 MHz, CD₃OD): δ 5.49 (br s, 1H, anomeric), 5.09 (br s, 1H, anomeric), 4.86 (s, 1H, anomeric), 4.30 (br d, 1H, J=4.9 Hz), 4.06 (t, 1H, J=5.6 Hz), 3.91 (m, 4H), 3.76 (m, 2H), 3.56 (m, 3H), 3.49 (m, 3H), 3.48 (m, 2H), 3.39 (m, 2H), 3.28 (m, 3H), 3.08 (m, 1H), 2.32 (m, 2H), 1.96 (d, 1H, J=12.5 Hz), 1.66 (m, 2H), 1.47 (3 s, 54H), 1.35 (m, 5H), 0.93 (t, 3H, J=6.7 Hz); ¹³C NMR (75 MHz, CD₃OD): δ 176.7 (amide CO—NH), 159.1, 158.9, 158.6, 158.5, 158.2, 157.9, 112.2 (anomeric), 100.5 (anomeric), 98.8 (anomeric), 88.6, 81.0, 80.8, 80.7, 80.4, 80.3, 79.3, 75.5, 74.2, 73.4, 72.6, 72.5, 69.0, 56.8, 53.6, 52.6, 51.3, 44.0, 39.0, 37.0, 35.8, 32.7, 29.1, 29.0, 28.8, 27.0, 23.6, 14.5 (aliphatic CH₃); $[\alpha]_D^{25}=+50.0$ (c 0.2, MeOH); EIMS: calcd for $C_{59}H_{105}N_7NaO_{25}^+$ 1334.70. Found: 1334.50 [M+Na]⁺.

1,3,2′,6′,2‴,6‴-Hexaammonium-5″-deoxy-5″-N-(hexanoyl)-neomycin hexakis(trifluoroacetate) (13)

Yield=91%; $R_f$ 0.10 (NH₄OH/MeOH/CH₂Cl₂ 2:5:5); ¹H NMR (300 MHz, CD₃OD): δ 5.83 (d, 1H, anomeric, J=4.1 Hz), 5.41 (d, 1H, anomeric, J=5.3 Hz), 5.31 (br d, 1H, anomeric, J=1.47 Hz), 4.40 (d, 1H, J=3.7 Hz), 4.29 (q, 1H, J=3.7 Hz), 4.22 (q, 1H, J=3.7 Hz), 4.20 (m, 1H), 4.17 (t, 1H, J=3.7 Hz), 4.10 (t, 1H, J=4.5 Hz), 4.03 (m, 2H), 3.89 (t, 1H, J=8.9 Hz), 3.70 (dd, 2H, J=2.5, 14.4 Hz), 3.63 (dd, 1H, J=6.9, 13.9 Hz), 3.56 (dd, 1H, J=3.8, 10.5 Hz), 3.45 (m, 2H), 3.41 (dd, 2H, J=3.4, 6.7 Hz), 3.37 (m, 1H), 3.30-3.20 (m, 3H), 3.18 (m, 1H), 2.46 (m, 1H), 2.26 (t, 2H, J=7.2 Hz), 1.62 (quin, 2H, J=7.2 Hz), 1.35 (s, 5H), 0.93 (t, 3H, J=6.8 Hz); ¹³C NMR (75 MHz, CD₃OD): δ 177.3 (amide CO—NH), 164.0-162.7 (TFA, q with $J^2_{CF}$~34.8 Hz), 124.1-112.4 (q with $J^1_{CF}$~292.0 Hz), 109.7, 97.3, 97.0, 86.8, 83.5, 78.2, 76.8, 75.8, 75.7, 74.2, 73.0, 72.1, 72.0, 69.6, 69.4, 69.3, 58.4, 55.1, 52.8, 51.2, 41.9, 41.8, 37.2, 32.6, 29.7, 26.7, 23.4, 14.4; $[\alpha]_D^{25}=+76.0$ (c 0.05, MeOH); EIMS: calcd for $C_{29}H_{58}N_7O_{13}^+$ 712.41. Found: 712.04 [M+H]⁺.

5″-N-(Dodecanoyl)-1,3,2′,6′,2‴,6‴-hexa-N-(tert-butoxycarbonyl)-5″-deoxy-neomycin (7)

Yield=90%; $R_f$ 0.51 (MeOH/CH₂Cl₂ 1:12); ¹H NMR (300 MHz, CD₃OD): δ 5.49 (br s, 1H, anomeric), 5.09 (br s, 1H, anomeric), 4.86 (s, 1H, anomeric), 4.30 (d, 1H, J=4.3 Hz), 4.06 (t, 1H, J=5.9 Hz), 3.91 (m, 4H), 3.76 (m, 2H), 3.56 (m, 4H), 3.49 (m, 3H), 3.38 (m, 3H), 3.25-3.20 (m, 3H), 3.10 (m, 1H), 2.32 (m, 2H), 1.96 (d, 1H, J=10.7 Hz), 1.66 (m, 3H), 1.47 (3 s, 54H), 1.30 (s, 16H), 0.93 (t, 3H, J=6.9 Hz); ¹³C NMR (75 MHz, CD₃OD): δ 176.7, 159.1, 158.9, 158.6, 158.3, 157.9, 112.2, 100.5, 98.8, 88.6, 81.0, 80.8, 80.7, 80.4, 80.3, 79.3, 76.2, 75.6, 74.4, 73.4, 72.7, 72.5, 71.7, 69.1, 56.9, 56.8, 53.6, 52.7, 51.3, 44.0, 42.0, 39.0, 37.0, 35.7, 33.1, 30.8, 30.7, 30.6, 30.5, 29.1, 29.0, 28.9, 28.8, 27.0, 23.6, 14.5; $[\alpha]_D^{25}=+32.0$ (c 0.25, MeOH); EIMS: calcd for $C_{65}H_{117}N_7NaO_{25}^+$ 1418.79. Found: 1419.01 [M+Na]⁺.

1,3,2′,6′,2‴,6‴-Hexaammonium-5″-deoxy-5″-N-(dodecanoyl)-neomycin hexakis(trifluoroacetate) (14)

Yield=93%; $R_f$ 0.11 (NH₄OH/MeOH/CH₂Cl₂, 2:5:5); ¹H NMR (300 MHz, CD₃OD): δ 5.83 (d, 1H, J=4.1 Hz), 5.41 (d, 1H, J=4.8 Hz), 5.31 (br s, 1H), 4.41 (d, 1H, J=3.7 Hz), 4.39 (d, 1H, J=4.1 Hz), 4.30 (m, 1H), 4.23 (m, 1H), 4.20 (m, 1H), 4.17 (m, 1H), 4.07 (t, 1H, J=5.4 Hz), 4.02 (m, 2H), 3.89 (t, 1H, J=8.9 Hz), 3.71 (m, 3H), 3.54 (dd, 1H, J=3.7, 9.9 Hz), 3.45 (m, 2H), 3.41 (m, 2H), 3.37 (m, 1H), 3.29 (d, 1H, J=3.2 Hz), 3.24 (d, 1H, J=6.0 Hz), 3.21 (m, 1H), 2.46 (m, 1H), 2.26 (t, 2H, J=7.7 Hz), 2.10 (t, 1H, J=12.8 Hz), 1.62 (t, 2H, J=7.1 Hz), 1.30 (br s, 16H), 0.93 (t, 3H, J=6.8 Hz); $^{13}$C NMR (75 MHz, CD$_3$OD): δ 177.2, 164.0-162.7 (TFA carbons, q with $J^1_{CF}$~34.8 Hz), 124.1-112.4 (TFA carbons, q with $J^1_{CF}$~292.0 Hz), 109.8, 97.8, 96.8, 86.6, 83.5, 78.2, 76.4, 75.7, 74.1, 73.0, 72.1, 72.0, 69.5, 69.3, 55.1, 52.9, 51.2, 50.4, 49.9, 41.9, 41.8, 41.7, 37.2, 33.1-23.7 (aliphatic carbons, C-2), 14.4; $[α]_D^{25}$=+32.8 (c 1.5, MeOH); EIMS: calcd for $C_{35}H_{70}N_7O_{13}^+$ 796.49. Found: 796.16 [M+H]$^+$.

5″-N-(Hexadecanoyl)-1,3,2′,6′,2‴,6‴-hexa-N-(tert-butoxycarbonyl)-5″-deoxy-neomycin (8)

Yield=88%; $R_f$ 0.51 (MeOH/CH$_2$Cl$_2$ 1:12); $^1$H NMR (300 MHz, CD$_3$OD): δ 5.49 (br s, 1H, anomeric), 5.09 (br s, 1H, anomeric), 4.86 (s, 1H, anomeric), 4.30 (d, 1H, J=3.4 Hz), 4.06 (t, 1H, J=5.5 Hz), 3.91 (m, 4H), 3.76 (m, 2H), 3.56 (m, 4H), 3.49 (m, 3H), 3.39 (m, 4H), 3.28-3.09 (m, 3H), 2.34 (m, 2H), 1.96 (dt, 1H, J=3.8, 12.5 Hz), 1.66 (t, 2H, J=6.1 Hz), 1.47 (3 s, 54H), 1.35 (s, 25H), 0.93 (t, 3H, J=6.1 Hz); $^{13}$C NMR (75 MHz, CD$_3$OD): δ 176.8, 159.1, 158.9 (2×), 158.5, 158.2, 157.9, 100.5, 98.9, 98.8, 88.5, 81.1, 80.9, 80.7, 80.4, 80.3, 76.3, 75.5, 74.6, 73.3, 72.6, 72.5, 71.8, 69.2, 56.9, 53.5, 51.3, 48.5, 44.0, 42.1, 37.0, 35.8, 33.1, 30.8-23.8 (aliphatic carbons), 14.5; $[α]_D^{25}$=+36.0 (c 0.8, MeOH); EIMS: calcd for $C_{69}H_{125}N_7NaO_{25}^+$ 1474.86. Found: 1474.41 [M+Na]$^+$.

1,3,2′,6′,2‴,6‴-Hexaammonium-5″-deoxy-5″-N-(hexadecanoyl)-neomycin hexakis(trifluoroacetate) (15)

Yield=92%; $R_f$ 0.11 (NH$_4$OH/MeOH/CH$_2$Cl$_2$, 2:5:5); $^1$H NMR (300 MHz, CD$_3$OD): δ 5.83 (d, 1H, J=4.1 Hz), 5.41 (d, 1H, J=4.9 Hz), 5.31 (br d, 1H, J=1.5 Hz), 4.41 (t, 1H, J=4.3 Hz), 4.29 (dd, 1H, J=3.7, 6.3 Hz), 4.22 (m, 2H), 4.17 (t, 1H, J=3.8 Hz), 4.09 (t, 1H, J=5.8 Hz), 4.02 (m, 2H), 3.92 (t, 1H, J=8.9 Hz), 3.70 (m, 3H), 3.63 (dd, 2H, J=3.5, 10.5 Hz), 3.45 (m, 2H), 3.40 (dd, 2H, J=3.2, 7.7 Hz), 3.37 (m, 1H), 3.30-3.16 (m, 3H), 2.49 (dt, 1H, J=3.8, 12.5 Hz), 2.26 (t, 2H, J=7.7 Hz), 1.62 (quintet, 2H, J=6.9 Hz), 1.30 (s, 25H), 0.93 (t, 3H, J=6.8 Hz); $^{13}$C NMR (75 MHz, CD$_3$OD): δ 177.2, 164.0-162.7 (TFA, q with $J^2_{CF}$~34.8 Hz), 124.1-112.4 (q with $J^1_{CF}$~292.0 Hz), 109.5, 97.3, 96.8, 86.6, 83.5, 78.2, 76.5, 75.7, 75.6, 75.4, 74.1, 72.8, 72.0, 69.5, 69.3, 69.2, 58.4, 55.1, 52.9, 51.1, 41.8, 41.9, 41.7, 37.1, 33.1, 30.8-23.7 (aliphatic carbons), 14.4; $[α]_D^{25}$=+40.0 (c 0.3, MeOH); EIMS: calcd for $C_{39}H_{78}N_7O_{13}^+$ 852.55. Found: 852.22 [M+H]$^+$.

5″-N-(Nonadecanoyl)-1,3,2′,6′,2‴,6‴-hexa-N-(tert-butoxycarbonyl)-5″-deoxy-neomycin (9)

Yield=89%; $R_f$ 0.53 (MeOH/CH$_2$Cl$_2$ 1:12); $^1$H NMR (300 MHz, CD$_3$OD): δ 5.49 (br s, 1H), 5.09 (br s, 1H), 4.86 (s, 1H), 4.30 (br d, 1H, J=3.6 Hz), 4.06 (t, 1H, J=5.6 Hz), 3.95 (d, 2H, J=5.8 Hz), 3.91 (d, 2H, J=3.5 Hz), 3.86 (m, 1H), 3.76 (m, 3H), 3.56-3.45 (m, 6H), 3.40 (m, 3H), 3.29-3.09 (m, 3H), 2.32 (m, 2H), 1.96 (d, 1H, J=12.8 Hz), 1.66 (m, 3H), 1.47 (s, 54H), 1.30 (s, 32H), 0.93 (t, 3H, J=7.1 Hz); $^{13}$C NMR (75 MHz, CD$_3$OD): δ 176.6, 159.0, 158.9, 158.6, 158.2, 157.9, 112.1, 100.5, 98.8, 88.5, 81.1, 80.8, 80.7, 80.4, 76.2, 75.6, 74.5, 73.5, 72.6, 71.7, 69.1, 56.9, 53.6, 52.4, 51.3, 48.7, 42.8, 42.1, 37.1, 35.8, 33.1, 30.9, 30.7-23.8 (aliphatic carbons), 14.6; $[α]_D^{25}$=+37.0 (c 0.8, MeOH); EIMS: calcd for $C_{73}H_{133}N_7NaO_{25}^+$ 1530.92. Found: 1530.73 [M+Na]$^+$.

1,3,2′,6′,2‴,6‴-Hexaammonium-5″-deoxy-5″-N-(nonadecanoyl)-neomycin hexakis(trifluoroacetate) (16)

Yield=92%; $R_f$ 0.12 (NH$_4$OH/MeOH/CH$_2$Cl$_2$, 2:5:5); $^1$H NMR (300 MHz, CD$_3$OD): δ 5.83 (d, 1H, J=2.8 Hz), 5.41 (d, 1H, J=4.3 Hz), 5.31 (s, 1H), 4.41 (t, 1H, J=3.7 Hz), 4.30 (m, 1H), 4.22 (br d, 2H, J=3.8 Hz), 4.17 (br t, 1H, J=2.6 Hz), 4.06 (t, 1H, J=5.8 Hz), 4.03 (t, 2H, J=9.3 Hz), 3.89 (t, 1H, J=5.8 Hz), 3.70 (m, 3H), 3.56 (dd, 2H, J=2.7, 10.3 Hz), 3.45 (m, 3H), 3.40 (d, 2H, J=5.2 Hz), 3.28-3.16 (m, 3H), 2.48 (d, 1H, J=11.4 Hz), 2.26 (t, 2H, J=7.7 Hz), 1.62 (m, 3H), 1.30 (s, 32H), 0.93 (t, 3H, J=6.8 Hz); $^{13}$C NMR (300 MHz, CD$_3$OD): δ 177.2, 164.0-162.7 (TFA, q with $J^2_{CF}$~34.8 Hz), 124.1-112.4 (q with $J^1_{CF}$~292.0 Hz), 109.5, 97.3, 97.3, 96.8, 86.6, 83.5, 78.2, 76.5, 75.7, 74.0, 77.0, 72.0, 71.9, 69.5, 69.4, 69.3, 55.2, 52.9, 51.1, 50.3, 41.9, 41.8, 41.7, 37.1, 33.1-23.8 (aliphatic carbons), 14.4; $[α]_D^{25}$=+29.0 (c 0.25, MeOH); EIMS: calcd for $C_{43}H_{86}N_7O_{13}^+$ 908.63. Found: 908.22 [M+H]$^+$.

5″-N-(9Z,12Z,Octadeca-di-ene-oyl)-1,3,2′,6′,2‴,6‴-hexa-N-(tert-butoxycarbonyl)-5″-deoxy-neomycin (10)

Yield=88%; $R_f$ 0.53 (MeOH/CH$_2$Cl$_2$ 1:12); $^1$H NMR (300 MHz, CD$_3$OD): δ 5.49 (br s, 1H), 5.42-5.28 (m, 4H), 5.09 (br s, 1H), 4.89 (s, 1H), 4.30 (d, 1H, J=3.5 Hz), 4.06 (t, 1H, J=5.3 Hz), 3.91 (m, 4H), 3.76 (m, 2H), 3.56 (m, 4H), 3.49 (m, 3H), 3.40 (m, 4H), 3.25 (d, 1H, J=8.8 Hz), 3.20 (m, 2H), 2.79 (t, 1H, J=5.8 Hz), 2.40-2.21 (m, 2H), 2.08 (q, 3H, J=6.4 Hz), 1.96 (m, 1H), 1.68 (m, 3H), 1.47 (s, 54H), 1.47 (s, 16H), 0.93 (t, 3H, J=6.8 Hz); $^{13}$C NMR (75 MHz, CD$_3$OD): δ 176.6, 159.0, 158.9 (2×), 158.6, 158.2, 157.9, 130.9, 129.1, 112.1, 100.5, 98.8, 88.7, 81.1, 80.8, 80.7, 80.4, 79.4, 76.2, 75.6, 74.5, 73.4, 72.6, 72.5, 71.7, 69.1, 56.9, 53.6, 52.8, 51.6, 44.0, 42.8, 42.1, 37.1, 33.1, 32.7, 30.8-23.8 (aliphatic carbons), 14.6; $[α]_D^{25}$=+51.0 (c 0.35, MeOH); EIMS: calcd for $C_{71}H_{125}N_7NaO_{25}^+$ 1498.87. Found: 1498.80 [M+Na]$^+$.

1,3,2′,6′,2‴,6‴-Hexaammonium-5″-deoxy-5″-N-(9Z,12Z,ocadeca-di-ene-oyl)-neomycin hexakis(trifluoroacetate) (17)

Yield=90%; $R_f$ 0.12 (NH$_4$OH/MeOH/CH$_2$Cl$_2$, 2:5:5); $^1$H NMR (300 MHz, CD$_3$OD): δ 5.84 (br s, 1H), 5.41 (m, 2H), 5.36 (br s, 1H), 5.34 (br s, 1H), 5.30 (m, 2H), 4.40 (t, 1H, J=4.0 Hz), 4.30 (m, 1H), 4.22 (m, 2H), 4.16 (t, 1H, J=3.1 Hz), 4.08 (m, 3H), 3.89 (t, 1H, J=8.7 Hz), 3.69 (m, 3H), 3.53 (d, 2H, J=10.5 Hz), 3.45 (m, 2H), 3.40 (m, 3H), 3.26-3.17 (m, 3H), 2.79 (t, 1H, J=5.8 Hz), 2.50 (d, 1H, J=10.4 Hz), 2.27 (t, 2H, J=7.7 Hz), 2.07 (q, 3H, J=6.4 Hz), 1.62 (m, 3H), 1.35 (s, 16H), 0.92 (t, 3H, J=6.8 Hz); $^{13}$C NMR (75 MHz, CD$_3$OD): δ 177.5, 164.0-162.7 (TFA, q with $J^2_{CF}$~34.8 Hz), 131.0, 129.1, 124.1-112.4 (q with $J^1_{CF}$~292.0 Hz), 109.5, 97.4, 96.6, 86.9, 83.3, 78.0, 76.5, 75.7, 74.0, 72.9, 72.0, 71.9, 69.5, 69.3, 69.2, 65.0, 58.4, 55.2, 52.8, 51.3, 50.1, 41.8, 41.7, 37.1-23.9 (aliphatic carbons, C-2), 14.4; $[α]_D^{25}$=+25.0 (c 0.7, MeOH); EIMS: calcd for $C_{41}H_{78}N_7O_{13}^+$ 875.55. Found: 876.20 [M+H]$^+$.

5″-Deoxy-5″-N-((4-pyrenyl)-butanoyl)-1,3,2′,6′,2‴,6‴-hexa-N-(tert-butoxycarbonyl)-neomycin B (11)

Yield=87%; $R_f$ 0.53 (MeOH/CH$_2$Cl$_2$ 1:10); $^1$H NMR (300 MHz, CD$_3$OD): δ 8.37 (d, 1H, J=9.2 Hz), 8.19 (t, 2H, J=6.7

Hz), 8.14 (dd, 2H, J=2.1, 7.9 Hz), 8.03 (br s, 1H), 8.00 (t, 1H, J=7.7 Hz), 7.92 (d, 1H, J=7.9 Hz), 7.04 (d, 1H, J=4.3 Hz), 5.49 (br s, 1H), 5.12 (s, 1H), 4.91 (s, 1H), 4.31 (m, 1H), 4.10 (m, 2H), 3.99 (m, 2H), 3.92 (m, 2H), 3.77 (m, 3H), 3.59 (m, 2H), 3.50 (m, 5H), 3.40 (m, 2H), 3.22 (m, 3H), 2.81 (m, 2H), 2.56 (m, 2H), 2.20 (m, 2H), 1.95 (d, 1H, J=11.5 Hz), 1.68 (m, 1H), 1.47 (2 s, 27H), 1.39 (s, 18H), 1.31 (s, 9H); $^{13}$C NMR (75 MHz, CD$_3$OD): δ 176.2, 159.0, 158.9, 158.6, 158.2, 157.9, 137.6-124.6 (aromatic carbons), 112.1, 100.7, 99.1, 88.4, 81.3, 80.9, 80.8, 80.7, 80.4, 80.3, 76.2, 75.6, 74.5, 73.4, 72.7, 71.8, 69.2, 57.1, 57.0, 53.6, 52.6, 51.4, 44.0, 42.8, 42.2, 39.0, 36.8, 35.8, 29.4, 29.1, 28.9, 28.8; $[α]_D^{25}$=+59.0 (c 0.25, MeOH); EIMS: calcd for C$_{73}$H$_{H1}$N$_7$NaO$_{25}^+$ 1506.73. Found: 1506.98 [M+Na]$^+$.

1,3,2',6',2''',6'''-Hexaammonium-5''-deoxy-5''-N-((4-pyrenyl)-butanoyl)-neomycin hexakis(trifluoroacetate) (18)

Yield=91%; R$_f$ 0.12 (NH$_4$OH/MeOH/CH$_2$Cl$_2$ 2:5:5); $^1$H NMR (300 MHz, CD$_3$OD): δ 8.29 (d, 1H, J=8.1 Hz), 8.12 (t, 4H, J=8.1 Hz), 7.99 (m, 2H), 7.95 (d, 1H, J=7.2 Hz), 7.87 (d, 1H, J=7.2 Hz), 5.90 (s, 1H), 5.44 (br d, 1H, J=3.2 Hz), 5.31 (s, 1H), 4.40 (t, 1H, J=4.3 Hz), 4.27 (m, 2H), 4.16 (m, 1H), 4.12 (t, 1H, J=5.2 Hz), 4.02 (d, 2H, J=8.9 Hz), 3.92 (t, 1H, J=8.9 Hz), 3.69 (m, 3H), 3.59 (m, 2H), 3.46 (m, 3H), 3.36 (m, 3H), 3.23 (d, 2H, J=11.8 Hz), 3.11 (dd, 1H, J=8.4, 11.8 Hz), 2.46 (m, 3H), 2.16 (m, 3H); $^{13}$C NMR (75 MHz, CD$_3$OD): δ 176.8, 164.0-162.7 (TFA, q with J$^2_{CF}$~34.8 Hz), 137.3-124.3 (aromatic carbons), 124.1-112.4 (q with J$^1_{CF}$~292.0 Hz), 109.5, 97.4, 96.6, 86.6, 83.4, 78.3, 76.5, 75.7, 74.1, 73.1, 72.1, 72.0, 69.5, 69.4, 69.2, 58.4, 55.1, 52.9, 51.3, 41.9, 41.7, 38.9, 36.8, 33.9, 29.0; $[α]_D^{25}$=+30.0 (c 0.85, MeOH); EIMS: calcd for C$_{43}$H$_{62}$N$_7$O$_{13}^+$ 884.44. Found: 884.11 [M+H]$^+$.

5''-N-(Cholanoyl)-5''-deoxy-1,3,2',6',2''',6'''-hexa-N-(tert-butoxycarbonyl)-neomycin (12)

Yield=89%; R$_f$ 0.52 (MeOH/CH$_2$Cl$_2$ 1:10); $^1$H NMR (300 MHz, CD$_3$OD): δ 5.44 (s, 1H), 5.10 (br s, 1H), 4.88 (s, 1H), 4.29 (d, 1H, J=3.8 Hz), 4.05 (t, 1H, J=4.7 Hz), 3.99 (m, 3H), 3.81 (m, 2H), 3.76 (m, 2H), 3.58 (m, 3H), 3.53 (m, 1H), 3.49 (m, 3H), 3.45 (m, 4H), 3.25-3.10 (m, 5H), 2.46 (m, 1H), 2.28 (m, 3H), 2.01-1.80 (m, 9H), 1.62 (m, 6H), 1.46 (3 s, 54H), 1.35 (m, 4H), 1.14 (m, 3H), 1.04 (d, 3H, J=5.8 Hz), 0.93 (s, 3H), 0.72 (s, 3H); $^{13}$C NMR (75 MHz, CD$_3$OD): δ 177.6, 159.1, 158.9, 158.6, 158.3, 157.7, 112.7, 100.9, 98.9, 88.2, 81.3, 80.7, 80.4, 80.3, 80.2, 76.0, 75.3, 74.4, 73.8, 73.4, 72.9, 72.6, 71.6, 69.1, 61.6, 57.0, 53.6, 52.5, 51.4, 47.6, 43.3, 42.9, 41.1, 40.6, 37.1, 36.6-23.3 (aliphatic carbons), 18.0, 13.3; $[α]_D^{25}$=+46.0 (c 0.45, MeOH); EIMS: calcd for C$_{77}$H$_{133}$N$_7$NaO$_{28}^+$ 1626.90. Found: 1628.09 [M+Na]$^+$.

1,3,2',6',2''',6'''-Hexaammonium-5''-N-(cholanoyl)-5''-deoxy-neomycin hexakis(trifluoroacetate) (19)

Yield=92%; R$_f$ 0.10 (NH$_4$OH/MeOH/CH$_2$Cl$_2$ 2:8:5); $^1$H NMR (300 MHz, CD$_3$OD): δ 5.85 (d, 1H, J=2.5 Hz), 5.41 (d, 1H, J=4.5 Hz), 5.31 (br s, 1H), 4.39 (t, 1H, J=4.3 Hz), 4.29 (m, 1H), 4.22 (d, 1H, J=2.4 Hz), 4.17 (d, 2H, J=2.5 Hz), 4.07 (t, 1H, J=4.3 Hz), 3.99 (m, 2H), 3.91 (m, 1H), 3.83 (m, 2H), 3.70 (m, 3H), 3.57 (d, 2H, J=9.9 Hz), 3.45 (m, 5H), 3.30 (m, 4H), 2.46 (m, 2H), 2.32-2.20 (m, 4H), 2.01-1.80 (m, 9H), 1.62 (m, 6H), 1.53-1.26 (m, 5H), 1.04 (d, 3H, J=5.6 Hz), 0.93 (s, 3H), 0.72 (s, 3H); $^{13}$C NMR (75 MHz, CD$_3$OD): δ 177.0, 164.0-162.7 (TFA, q with J$^2_{CF}$~34.8 Hz), 124.1-112.4 (q with J$^1_{CF}$~292.0 Hz), 109.8, 97.3, 96.8, 87.0, 83.2, 78.4, 76.6, 75.6, 74.1, 73.2, 72.7, 72.1, 69.4, 69.3, 69.2, 54.9, 52.9, 50.8, 47.4, 43.2, 43.0, 41.9, 41.6, 40.8, 40.4, 37.0-23.2 (aliphatic carbons), 17.8, 13.0; $[α]_D^{25}$=+42.0 (c 0.65, MeOH); EIMS: C$_{47}$H$_{86}$N$_7$O$_{16}^+$ 1004.61. Found: 1004.33 [M+H]$^+$.

1,3,2',6',2''',6'''-hexaammonium-5''-N—(NHFmoc-Lysine-O-Bn)-5''-deoxy-neomycin-hexafluoroacetate (22)

$^1$H NMR (300 MHz, Methanol-d$_4$): δ 7.80 (d, 2H, J=7.3 Hz), 7.66 (t, 2H, J=7.4 Hz), 7.40 (d, 2H, J=7.3 Hz), 7.30 (m, 7H), 5.97 (d, 1H, J=4.3 Hz), 5.82 (d, 1H, J=1.8 Hz), 5.35 (t, 1H, J=4.3 Hz), 5.33 (br s, 1H), 5.15 (dd, 2H, J=6.6, 10.5 Hz), 4.76 (m, 1H), 4.61 (m, 1H), 4.40 (m, 2H), 4.32 (dd, 2H, J=6.6, 10.5 Hz), 4.25-4.12 (m, 3H), 4.10 (m, 1H), 4.05-3.88 (m, 4H), 3.73 (q, 2H, J=9.0 Hz), 3.71 (m, 2H), 3.67-3.58 (m, 2H), 3.49-3.40 (m, 3H), 3.26 (m, 1H), 3.18 (m, 3H), 2.86 (t, 1H, J=7.3 Hz), 2.49 (m, 1H), 2.22 (m, 1H), 1.86 (m, 1H), 1.66 (m, 2H), 1.43 (m, 2H), 1.20 (m, 1H); $^{13}$C NMR (75 MHz, CD$_3$OD): δ 173.8, 158.7, 145.3, 145.1, 142.6, 137.2, 129.6, 129.4, 129.1, 128.8, 128.2, 126.2, 120.9, 111.2, 99.4, 98.9, 87.8, 82.1, 79.3, 77.9, 77.2, 75.0, 74.3, 73.6, 72.0, 71.4, 71.2, 71.0, 70.9, 69.8, 69.4, 69.3, 69.2, 68.1, 62.1, 61.5, 55.4, 55.2, 52.7, 51.4, 50.4, 50.2, 42.1, 42.0, 41.6, 40.5, 31.9, 29.8, 27.9, 23.8. EIMS: calcd. for C$_{51}$H$_{75}$N$_8$O$_{16}^+$ 1055.53. Found: 1055.49 [M+H]$^+$.

1,3,2',6',2''',6'''-hexaammonium-5''-N—(NHFmoc-Trp-Lysine-O-Bn)-5''-deoxy-neomycin-heptafluoroacetate (24)

Procedure same as above for 21 and 22. Yield=87%; $^1$H NMR (300 MHz, Methanol-d$_4$): δ 7.82 (dd, 2H, J=3.4, 7.3 Hz), 7.72 (d, 2H, J=7.9 Hz), 7.60 (d, 2H, J=7.3 Hz), 7.41 (t, 2H, J=7.5 Hz), 7.35 (m, 3H), 7.22 (m, 3H), 7.16 (m, 3H), 7.03 (t, 1H, J=7.5 Hz), 5.97 (d, 1H, J=3.4 Hz), 5.85 (d, 1H, J=3.6 Hz), 5.46 (m, 1H), 5.39 (d, 1H, J=3.4 Hz), 5.33 (m, 1H), 5.29 (m, 1H), 5.18 (m, 2H), 4.97 (m, 1H), 4.58 (d, 1H, J=5.5 Hz), 4.45 (d, 1H, J=14.6 Hz), 4.32 (m, 3H), 4.16 (m, 2H), 4.03 (m, 3H), 3.87 (m, 1H), 3.75 (dd, 1H, J=4.8, 10.1 Hz), 3.69 (br d, 1H, J=2.8 Hz), 3.64 (m, 1H), 3.59 (m, 1H), 3.44 (m, 5H), 3.28 (m, 1H), 3.24 (m, 1H), 3.20 (m, 1H), 3.17 (d, 1H, J=4.5 Hz), 3.10 (m, 2H), 2.83 (m, 1H), 2.48 (m, 2H), 2.16 (m, 1H), 2.01 (m, 1H), 1.72 (m, 1H), 1.58 (m, 1H), 1.08 (m, 2H); $^{13}$C NMR (75 MHz, CD$_3$OD): δ 173.6, 158.4, 145.5, 145.2, 142.8, 139.4, 138.1, 129.6, 128.8, 128.5, 128.4, 128.3, 125.7, 125.3, 122.6, 121.2, 121.1, 119.9, 119.7, 110.4, 97.1, 96.6, 86.4, 82.1, 79.3, 78.5, 77.2, 76.9, 75.1, 74.3, 74.0, 73.3, 72.0, 71.8, 71.0, 69.8, 69.4, 69.2, 68.4, 58.9, 55.9, 55.2, 54.9, 52.9, 51.4, 51.2, 50.6, 50.3, 50.2, 44.3, 42.0, 41.6, 31.9, 30.1, 29.9, 29.7, 28.8, 23.8; EIMS: calcd. for C$_{62}$H$_{85}$N$_{10}$O$_{17}^+$1241.60. Found: 1241.58 [M+H]$^+$.

1,3,6',3''-Tetra-N-(tert-butoxycarbonyl)-6''-azido-6''-deoxy-kanamycin A (27)

R$_f$: 0.36 (MeOH/CH$_2$Cl$_2$ 1:12); IR (KBr disk) 2106.3 cm$^{-1}$ (N$_3$); $^1$H NMR (300 MHz, CD$_3$OD): δ 5.11 (br s, 1H), 5.10 (br s, 1H), 4.33 (d, 1H, J=9.8), 3.74 (d, 2H, J=9.8 Hz), 3.64 (t, 1H, J=9.2 Hz), 3.69 (dd, 1H, J=4.3, 11.5 Hz), 3.59 (m, 2H), 3.56 (d, 1H, J=2.5 Hz), 3.51 (d, 1H, J=2.5 Hz), 3.45 (dd, 2H, J=4.3, 11.5 Hz), 3.41 (d, 2H, J=3.8 Hz), 3.38 (t, 3H, J=3.6 Hz), 3.21 (t, 1H, J=9.4 Hz), 2.09 (br d, 1H, J=12.2 Hz), 1.55 (m, 1H), 1.47 (2 s, 36H); $^{13}$C NMR (75 MHz, CD$_3$OD): δ 156.4, 155.6, 154.9, 101.4 (anomeric), 97.6 (anomeric), 84.6, 79.6, 78.0, 75.1, 72.7, 72.2, 71.2, 70.4, 70.1, 68.2, 55.5, 50.7, 49.9, 49.1, 40.8, 34.7, 27.9, 27.6; EIMS: calcd for $C_{38}H_{67}N_4NaO_{18}^+$ 932.44. Found: 932.38 [M+Na]$^+$.

1,3,6',3''-Tetra-N-(tert-butoxycarbonyl)-6''-amino-6''-deoxy-kanamycin A (28)

The solution of kanamycin azide (500 mg, 0.549 mmol) and 10% Pd(OH)$_2$/C in methanol (25 mL) was hydrogenated at normal temperature and pressure for 4 h and then filtered through celite. Filtrate was concentrated and the residue was purified on flush column chromatography by using MeOH/CH$_2$Cl$_2$ (1:9) to afford 28 (411 mg, 85%), as a white solid. $^1$H NMR (300 MHz, CD$_3$OD-d$_6$): δ 5.06 (d, 1H, J=3.2 Hz), 5.03 (d, 1H, J=3.5 Hz), 4.52 (m, 1H), 4.34 (m, 1H), 4.23 (t, 1H, J=10.6 Hz), 4.03 (d, 1H, J=10.6 Hz), 3.80 (m, 1H), 3.72 (m, 1H), 3.69 (m, 1H), 3.66 (m, 1H), 3.62 (m, 2H), 3.52 (m, 2H), 3.46 (m, 1H), 3.42 (m, 2H), 3.22 (t, 1H, J=10.0 Hz), 3.00 (q, 1H, J=10.0 Hz), 2.10 (m, 1H), 1.52 (m, 1H), 1.46 (2 s, 36H); $^{13}$C NMR (75 MHz, CD$_3$OD): δ 159.2, 158.7, 157.6, 157.2, 123.2, 102.5, 99.8, 87.4, 85.9, 83.1, 80.4, 74.0, 73.4, 72.0, 71.2, 70.7, 69.7, 56.8, 51.6, 50.4, 41.4, 35.4, 28.9, 28.8; EIMS: calcd. for $C_{38}H_{70}N_5O_{18}^+$ 884.47. Found: 884.44 (M+H)$^+$.

6''-N-(Hexadecanoyl)-1,3,6',3''-tetra-N-(tert-butoxycarbonyl)-6''-deoxy-kanamycin (29)

Yield=87%; R$_f$ 0.31 (MeOH/CH$_2$Cl$_2$ 1:15); [α]$_D^{25}$=50.0 (c 0.7, MeOH); $^1$H NMR (300 MHz, CD$_3$OD): δ 5.09 (d, 1H J=2.5 Hz), 5.04 (d, 1H J=3.5 Hz), 4.21 (t, 1H, J=8.2 Hz), 3.71 (dd, 1H, J=9.6, 16.6 Hz), 3.64 (d, 3H, J=9.4 Hz), 3.58 (t, 2H, J=7.7 Hz), 3.54-3.36 (m, 8H), 3.24 (d, 1H, J=9.3 Hz), 3.19 (t, 1H, J=9.0 Hz), 2.23 (t, 2H, J=7.7 Hz), 2.06 (br d, 1H, J=11.2 Hz), 1.62 (m, 3H), 1.47 (2 s, 36H), 1.26 (s, 24H), 0.90 (t, 3H, J=6.7 Hz); $^{13}$C NMR (75 MHz, CD$_3$OD): δ 176.7, 159.3, 159.1, 158.0, 157.7, 102.9 (anomeric), 100.3 (anomeric), 86.2, 81.8, 80.6, 80.4, 80.1, 77.1, 74.6, 74.0, 72.4, 72.1, 72.0, 71.8, 71.3, 57.4, 52.3, 50.9, 42.1, 41.9, 37.3, 35.9, 33.1, 30.9, 29.0, 28.9, 27.0, 23.8, 14.6; EIMS: calcd. for $C_{54}H_{99}N_5NaO_{19}^+$ 1141.68. Found: 1141.57 (M+Na)$^+$.

1,3,6',3''-Tetraammonium-6''-deoxy-6''-N-(hexadecanoyl)-kanamycin-tetrakis-(trifluoroacetate) (30)

Yield=90%; R$_f$ 0.20 (NH$_4$OH/MeOH/CH$_2$Cl$_2$, 1:5:5); [α]$_D^{25}$=49.1 (c 0.1, MeOH); $^1$H NMR (300 MHz, CD$_3$OD): δ 5.46 (d, 1H J=3.5 Hz), 5.04 (d, 1H J=3.5 Hz), 4.06 (dt, 1H, J=2.2, 9.4 Hz), 3.95 (m, 1H), 3.84 (m, 4H), 3.71 (t, 2H, J=9.3 Hz), 3.64 (dd, 2H, J=4.8, 14.4 Hz), 3.61 (d, 1H, J=6.9 Hz), 3.54 (dd, 2H, J=3.6, 9.3 Hz), 3.50 (m, 1H), 3.39 (dd, 3H, J=2.3, 9.3 Hz), 3.22 (t, 1H, J=9.7 Hz), 3.02 (dd, 1H, J=9.4, 13.2 Hz), 2.53 (dt, 1H, J=3.6, 12.3 Hz), 2.25 (t, 2H, J=7.7 Hz), 2.01 (m, 1H), 1.62 (quintet, 2H, J=6.9 Hz), 1.30 (s, 24H), 0.90 (t, 3H, J=6.7 Hz); $^{13}$C NMR (75 MHz, CD$_3$OD): δ 177.7, 164.0-162.7 (TFA carbons, q with J$^1_{CF}$~34.8 Hz), 124.1-112.4 (TFA carbons, q with J$^1_{CF}$~292.0 Hz), 102.5 (anomeric), 97.0 (anomeric), 85.4, 81.9, 74.4, 73.5, 73.5, 73.0, 72.9, 70.6, 70.3, 68.4, 56.3, 51.8, 42.2, 40.8, 37.0, 33.1, 30.8, 30.7, 30.5, 30.4, 27.0, 23.8, 14.6; EIMS: calcd. for $C_{34}H_{68}N_5O_{11}^+$ 722.49. Found: 722.09 (M+H)$^+$.

Compound 31: EI HRMS: calcd. for 31 [M+H]$^+$= 1104.69655. Found 1104.69649; Elemental analysis for 31: $C_{57}H_{95}F_{18}N_{19}O_{25}$ calcd. C, 38.28; H, 5.35; F, 19.12; O, 22.36. Found: C, 38.18; H, 5.45; F, 19.34; O, 22.50.

Example 3

Antibacterial Testing of Certain Hydrophobically Enhanced Aminoglycoside Antibiotics of the Present Invention Methods Standard reference antibiotic susceptibility testing methods (NCCLS[CLS] (Clinical and Laboratory Standards Institute, 2006)) agar or dilutional methods was used to assess the activity of all prepared antimicrobials. Compounds were tested against Gram-positive strains including S. aureus, methicillin-resistant S. aureus (MRSA), S. epidermidis, methicillin-resistant S. epidermidis (MRSE) and S. pneumoniae as well as Gram-negative strains E. coli, gentamycin resistant E. coli and P. aeruginosa. The minimum inhibitory concentrations (MIC) in µg/mL were determined and are shown in Table 1 (FIG. 4). Gentamycin and neomycin served as positive controls. MIC values defined as the lowest concentration of antimicrobial agent which inhibits the development of visible growth after 24 h at 37° C. was determined.

For those compounds whose numbers end in A: Microorganisms from the American Type Culture Collection (ATCC) and Canadian Intensive Care Unit (CAN-ICU) were used, including: S. aureus ATCC 29213, methicillin-resistant Staphylococcus aureus (MRSA) ATCC 33592, S. epidermidis ATCC 14990, methicillin-resistant Staphylococcus epidermidis (MRSE) (Cefazolin-CZ MIC>32 µm/mL) CAN-ICU 61589, E. faecalis ATCC 29212, E. faecium ATCC 27270, S. pneumoniae ATCC 49619, E. coli ATCC 25922, E. coli ATCC (Gentamicin-resistant) CAN-ICU 61714, E. coli ATCC (Amikacin MIC 32 µg/mL) CAN-ICU 63074, P. aeruginosa ATCC 27853, P. aeruginosa (Gent-R) CAN-ICU 62308, S. maltophilia CAN-ICU 62584, A. baumannii CAN-ICU 63169 and K. pneumoniae ATCC 13883. The minimum inhibitory concentrations (MIC) in µg/mL were determined using established methods (Clinical and Laboratory Standards Institute, 2006) and are shown in Table 3 (FIG. 17). Gentamicin, neomycin B and kanamycin A served as positive controls.

Results

Figure 5:
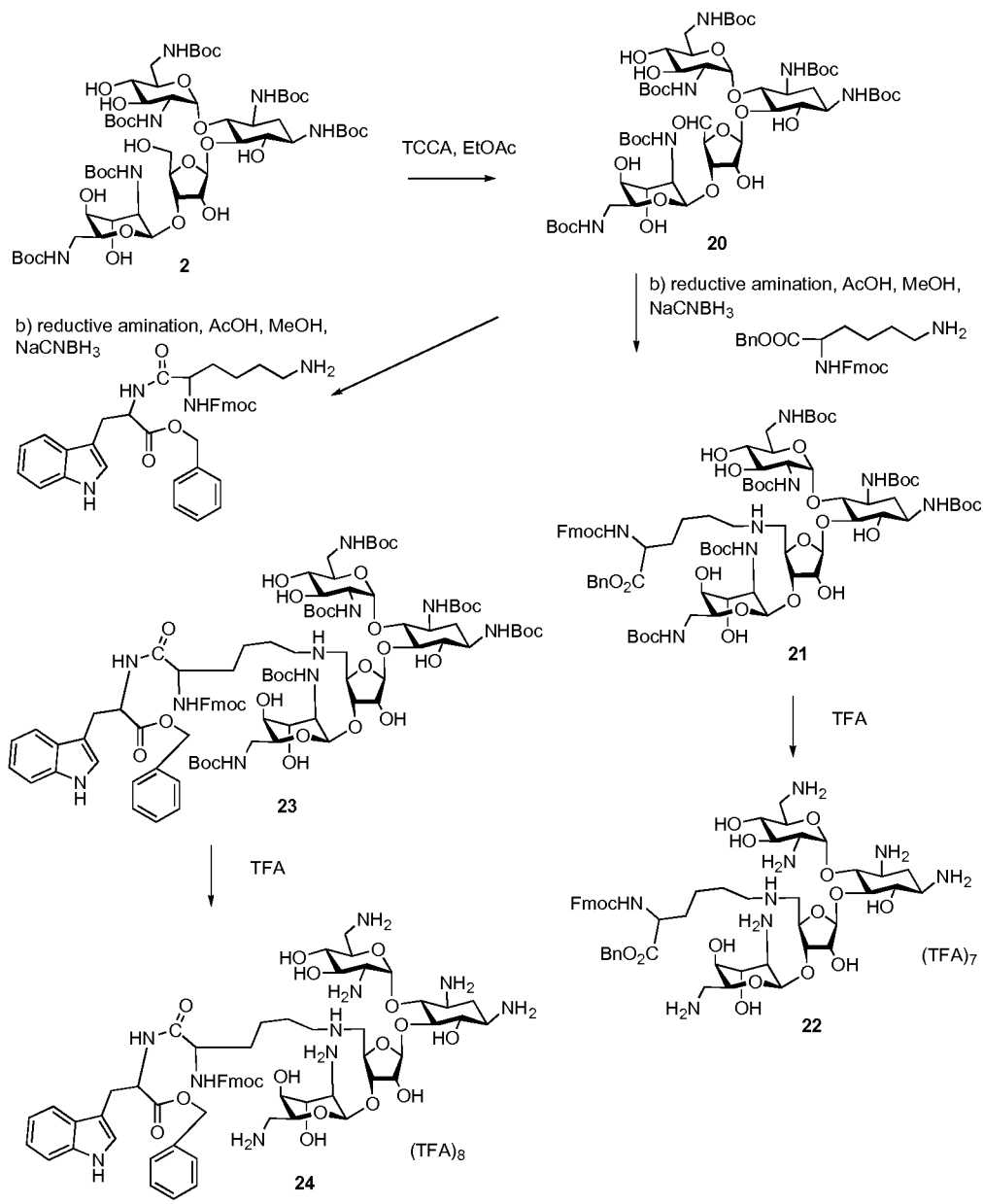
FIG. 5 Scheme 3: Reductive amination of aminoglycoside-based aldehyde 20 with hydrophobic amino acids and peptide-based amines.

It appears that saturated, aliphatic and long fatty acid chains induce optimal Gram-positive activity while hydrophobically enhanced neomycin analogs bearing pyrene or cholesterol appendages do result in significantly reduced antibacterial activities. A remarkable 32-fold enhancement against MRSA is observed for compounds 15 and 16 (MIC≤8 µg/mL) when compared to neomycin (MIC~8 µg/mL). In case of kanamycin A-lipid conjugate 30 (FIG. 7), the inventors observed a 56-fold enhancement in antimicrobial activity against MRSE and a 35-fold enhancement in antimicrobial activity against MRSA when compared to unmodified kanamycin A (Table 1, FIG. 4). The inventors also explored reductive amination reactions of neomycin derived aldehyde 20 described previously by Kudyba et al., 2007 with hydrophobic amines (amino acids, peptide amines) as shown in Scheme 3 (FIG. 5) and explored the antimicrobial activity against bacterial strains (Table 2, FIG. 6).

The results for compound 31 (Table 1 in FIG. 4) show that the conversion of the amino functions into the guanidine functions in neomycin-lipid conjugates results in potent Gram-positive and Gram-negative antibacterial activity.

It is to be noted that fatty acids exhibit significantly reduced antimicrobial activities. For instance, the most active fatty acid against MRSA and MSSA (methicillin-susceptible *S. aureus*) is lauric acid ($C_{12}$, MIC=400 μg/mL).

Regarding the compounds whose numbers end in A: Phenyl carbamoylation of the hydroxyl groups in neomycin B overcomes resistance in various multi-drug resistant Gram-positive and Gram negative organisms. For instance, neomycin B-modified phenyl carbamate 4A exhibits a 128-fold enhancement in antimicrobial activity against Gram-positive MRSA and Gram-negative *S. maltophilia* when compared to unmodified neomycin B. Potent antimicrobial activity is also observed against other multi-drug resistant organisms such as MRSE (MIC=0.5 μg/ml), gentamicin-resistant *E. coli* (MIC=16 μg/ml) and amikacin-resistant *E. coli* (MIC=16 μg/ml). In addition, very potent activity is observed against Gram-positive *S. aureus* (MIC=1 μg/ml) and *S. epidermidis* (MIC=0.5 μg/ml). The least antibacterial activity is observed for *K. pneumoniae* and *P. aeruginosa*.

Guanidinylated neomycin B analog 9A exhibits slightly reduced antibacterial activity when compared to 4A. Replacement of a hydrogen atom by a chlorine atom results in a significant drop in antimicrobial activity for most investigated bacteria. For instance, a 64-fold drop in antibacterial activity is observed against Gram-positive *S. aureus*, MRSA and MRSE while a 32-fold loss in activity is observed against Gram-negative *S. maltophilia*. By comparison, reduced Gram-positive antibacterial activities are observed for kanamycin A-, amikacin-, and neamine-based phenylcarbamates 11A, 20A and 17A, respectively. Moreover, kanamycin A- and amikacin-based phenylcarbamates exhibit poor Gram-negative activity while neamine-based phenyl carbamate exhibits higher Gram-negative activity.

How phenyl carbamate-lipid conjugation influences antibacterial activity was also investigated. A previous study (U.S. Provisional Appl. No. 61/079,338 filed Jul. 9, 2008, incorporated herein by reference) has shown that conjugation of C16 lipids to the C5' position of neomycin can result in enhanced antibacterial activity against MRSA. However, neomycin B-based phenylcarbamate-lipid conjugate 7A and kanamycin A-based lipid conjugate 14A show poor Gram-positive and Gram-negative activity against all studied organisms.

Example 4

Synthesis and Characterization of Various Aminoglycoside-Hydrophobe Conjugates

The following aminoglycoside-hydrophobe conjugates, wherein the hydrophobe is phenyl, substituted phenyl, or lipid, were prepared. FIG. 8 through FIG. 16 show some of the reaction schemes for the compounds described in this Example.

Neomycin-Based Polycationic Carbamates 4A and 22A

The synthesis of neomycin-based polycationic carbamates is outlined in Schemes 1 and 2. Initially, tert-butyloxycarbamate-protected neomycin 2A (Quader et al., 2007) reacted with phenyl isocyanate in pyridine for two days to produce oligophenylcarbamate 3A (Scheme 5, FIG. 8) which by exposure to trifluoroacetic acid was converted into polycationic phenylcarbamate 4A in quantitative yield. Similarly, treatment of 2A with p-chlorophenylisocyanate produced p-chlorophenylisocyanate 21A that was converted into polycationic p-chlorophenylcarbamate 22A (Scheme 6, FIG. 9).

Kanamycin-Based Polycationic Carbamate 11A

Figure 10:
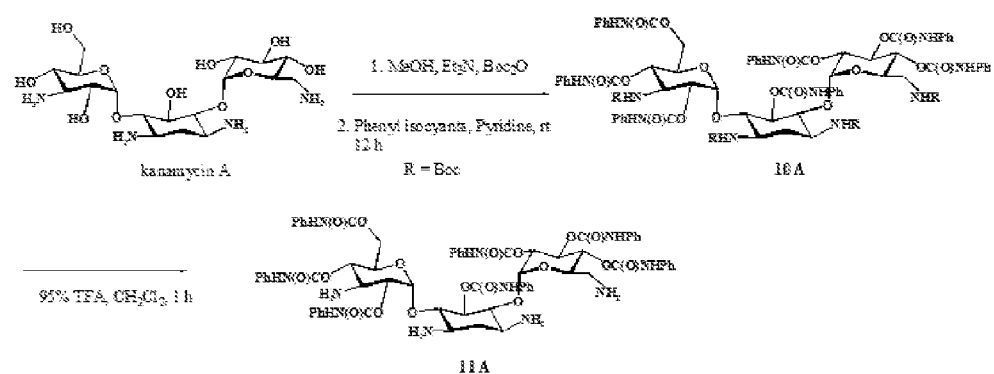
FIG. 10 Scheme 7: Synthesis of kanamycin A-based polycationic phenyl carbamate 11A.

The synthesis of a kanamycin-based polycationic carbamates is outlined in Scheme 7 (FIG. 10). Initially, tert-butyloxycarbamate-protected kanamycin 10A (Disney and Barrett, 2007) reacted with phenyl isocyanate in pyridine for two days to produce oligophenylcarbamate 10A which, by exposure to trifluoroacetic acid, was converted into polycationic phenylcarbamate 11A.

Amikacin-Based Polycationic Carbamate 20A

Figure 11:
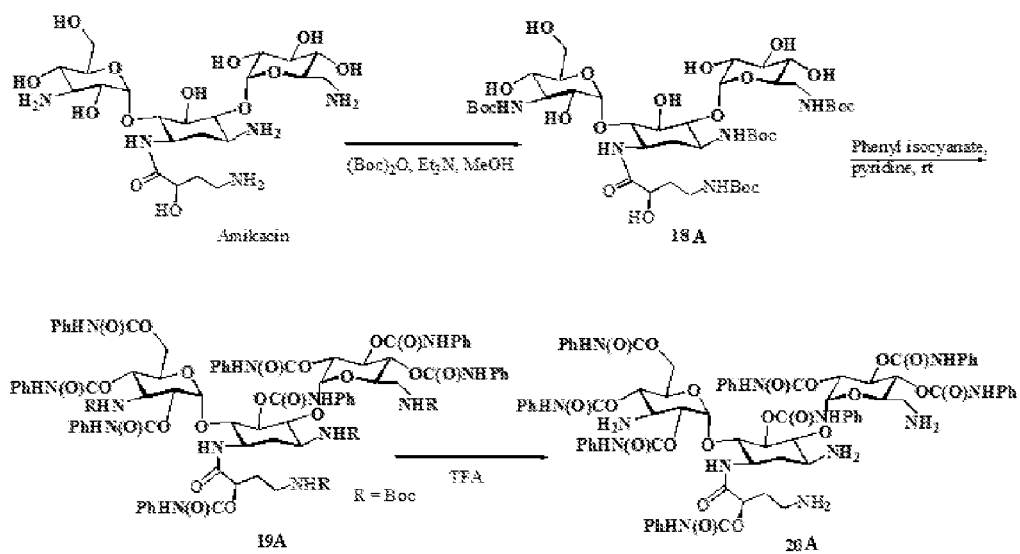
FIG. 11 Scheme 8: Synthesis of amikacin-based polycationic phenyl carbamate 20A.

The synthesis of amikacin-based polycationic carbamates is outlined in Scheme 8, FIG. 11. Initially, tertbutyloxycarbamate-protected amikacin 18A reacted with phenyl isocyanate in pyridine for two days to produce oligophenylcarbamate 19A which by exposure to trifluoroacetic acid was converted into polycationic phenylcarbamate 20A.

Neamine-Based Polycationic Carbamate 17A

Figure 12:
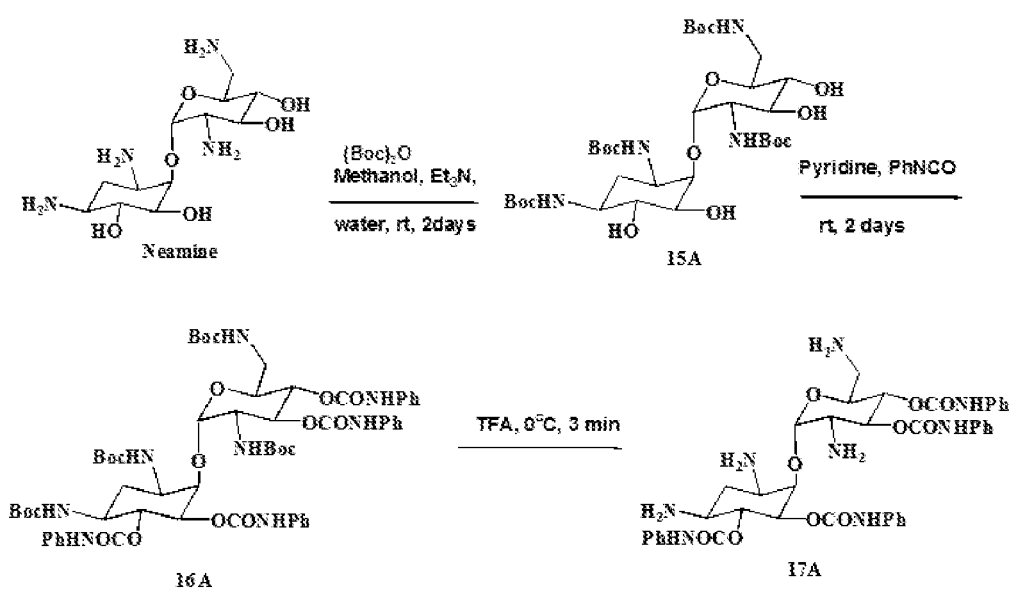
FIG. 12 Scheme 9: Synthesis of neamine-based polycationic phenyl carbamate 17A.

The synthesis of neamine-based polycationic carbamate 17A is outlined in Scheme 9, FIG. 12. Initially, tertbutyloxycarbamate-protected neamine 15A (Tohma et al., 1980) reacted with phenyl isocyanate in pyridine for two days to produce oligophenylcarbamate 16A which by exposure to trifluoroacetic acid was converted into polycationic phenylcarbamate 17A.

Synthesis of Polycationic Lipid Carbamates

Synthesis of Neomycin B-Based Polycationic Lipid-Carbamate 7A

Figure 13:
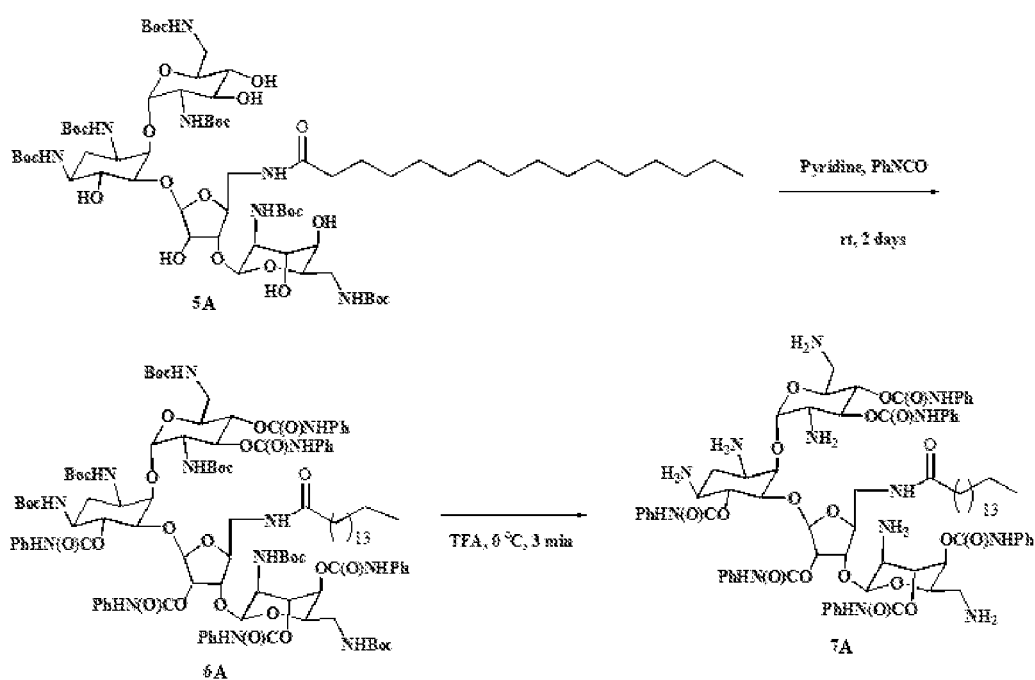
FIG. 13 Scheme 10: Synthesis of neomycin B-based polycationic lipid-phenyl carbamate 7A.

The synthesis of neomycin-based polycationic lipid-carbamates is outlined in Scheme 10, FIG. 13. Initially, lipid-modified tertbutyloxycarbamate-protected neomycin 5A (U.S. Provisional Appl. No. 61/079,338) reacted with phenyl isocyanate in pyridine for two days to produce lipid oligophenylcarbamate 3A which, by exposure to trifluoroacetic acid, was converted into polycationic lipid-phenylcarbamate 7A.

Synthesis of Kanamycin A-Based Polycationic Lipid Carbamate 14A

Figure 14:
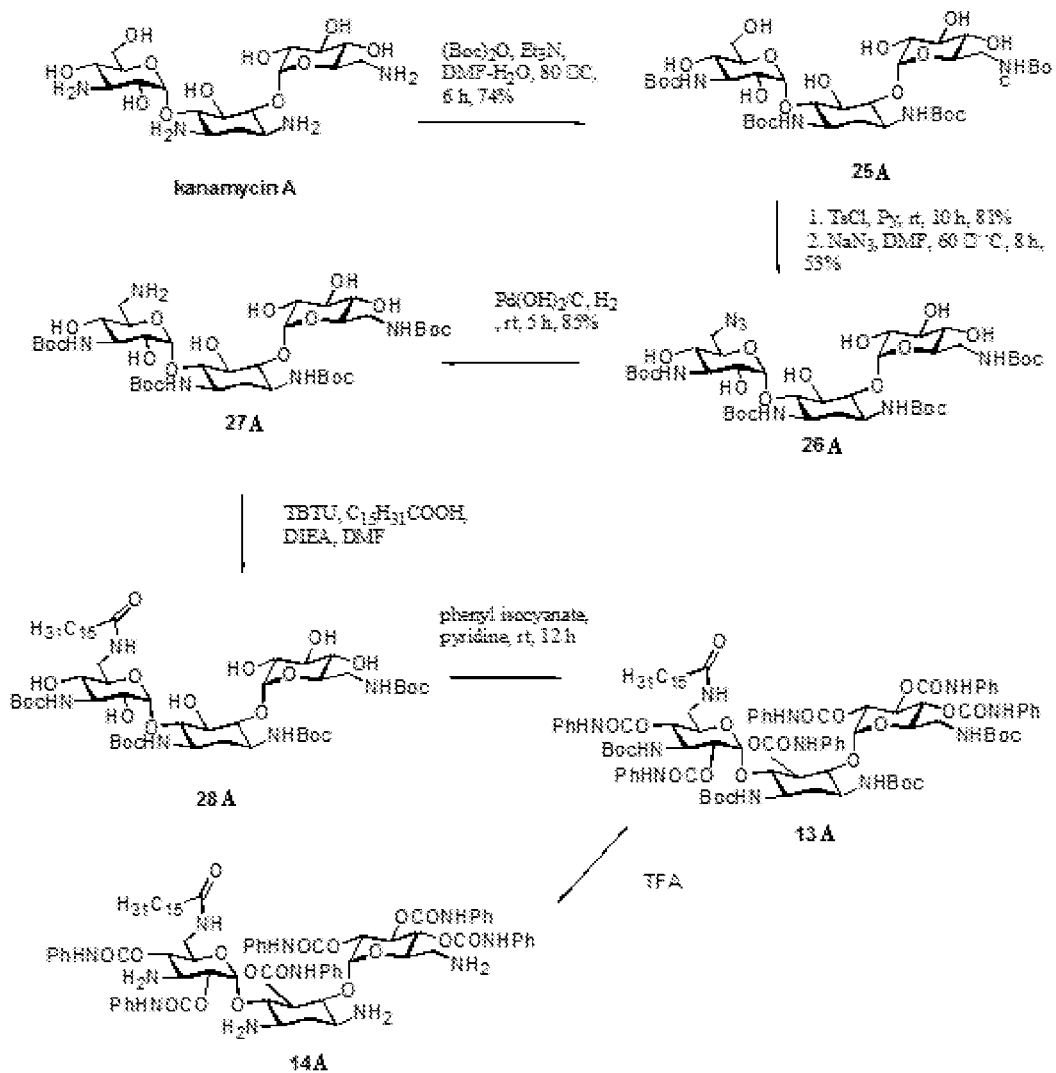
FIG. 14 Scheme 11: Synthesis of kanamycin A-based polycationic lipid-phenyl carbamate 14A.

The synthesis of kanamycin A-based polycationic lipid-carbamate 14A is outlined in Scheme 14, FIG. 14. Initially, Boc-protected kanamycin A reacted with p-toluenesulfonyl-chloride in pyridine to form the sulfonate ester that was treated with sodium azide in dimethylformamide at elevated temperature to produce azide 26A. Catalytic hydrogenation of the azide function generated amine 27A that was coupled to palmitic acid to form kanamycin A-lipid conjugate 28A. Compound 28A reacted with phenyl isocyanate in pyridine for two days to produce lipid oligophenylcarbamate 13A which, by exposure to trifluoroacetic acid, was converted into polycationic lipid-phenyl carbamate 14A.

Synthesis of Oligoguanidino Phenyl Carbamate 9A

Figure 15:
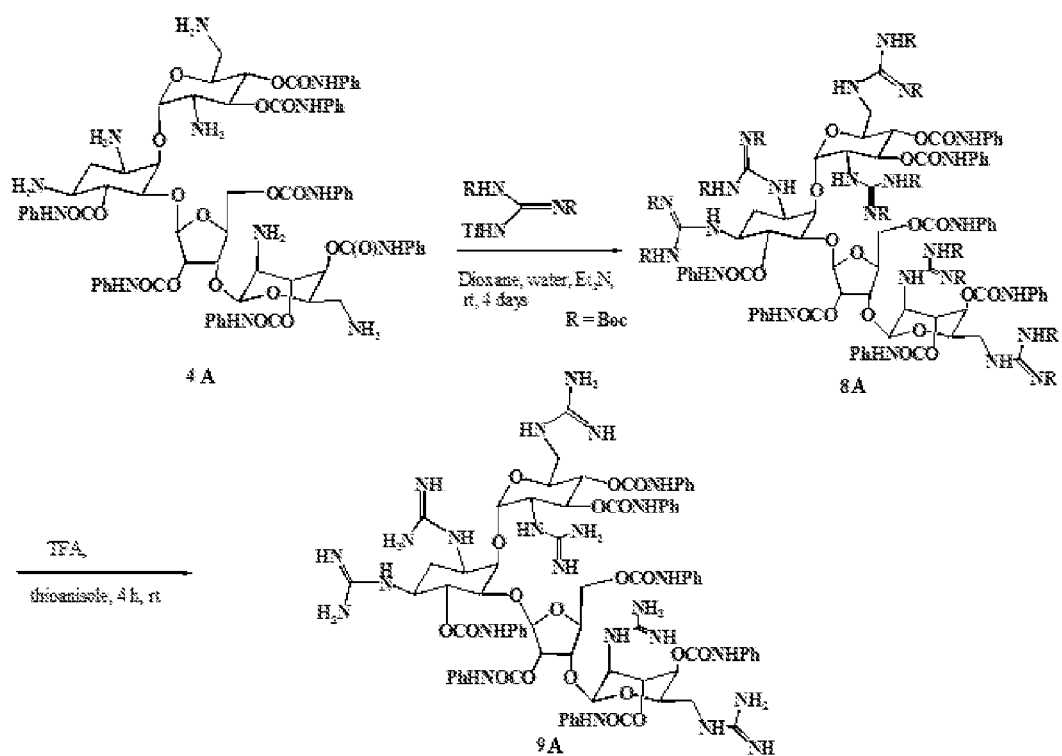
FIG. 15 Scheme 12: Synthesis of neomycin B-based polyguanidinyl phenyl carbamate 9A.

The synthesis of neomycin B-based oligoguanidinylated phenyl carbamate 9A is shown in Scheme 12, FIG. 15. Initially, previously synthesized oligophenyl carbamate 4 reacted with N,N'-diBoc-N"-triflylguanidine (Baker et al., 2000) in a solvent mixture containing dioxane, water and triethylamine to form compound 8A that was exposed to trifluoroacetic acid to generate neomycin B-based oligoguanidinylated phenyl carbamate 9A.

Synthesis of Polycationic Polyether 24A

Figure 16:
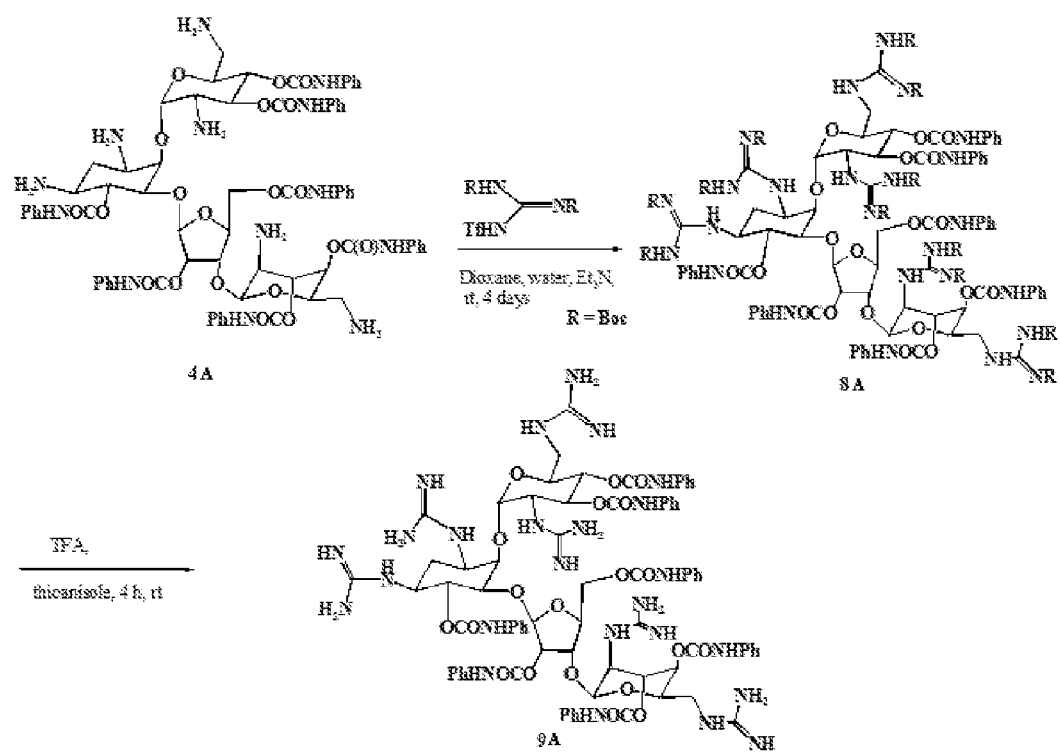
FIG. 16 Scheme 13: Synthesis of polycationic polyether 24A.
Figure 18:
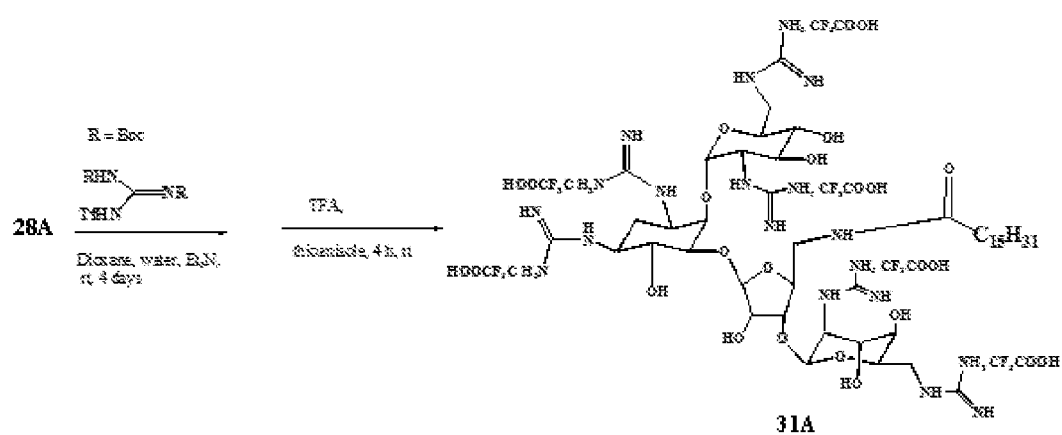
FIG. 18 Structure and synthesis of compound 31.

The synthesis of polycationic benzylether 24A is outlined in Scheme 13, FIG. 16. Initially, tertbutyloxycarbamate-protected neomycin 2A (Quader et al., 2007) was treated with barium hydroxide and benzylbromide in dimethylformamide at 0° C.-rt for 48 hours to afford protected cationic polyphenylether 23A. Exposure of compound 23A to trifluoroacetic acid provided deblocked cationic polyether 24A in quantitative yield.

General Procedure for Carbamate Formation:

To a solution of Boc protected aminoglycoside (1 equiv.) in dry pyridine phenylisocynate (1.5 eq) was added and stirred at rt for the time stated above. Pyridine was removed under reduced pressure and the crude residue was purified by flush column chromatography, eluted by MeOH/CH$_2$Cl$_2$ to get pure carbamate derivatives as amorphous solid.

General Procedure for Removal of Boc Group:

Carbamate derivatives (0.050 mmol) were treated with 99% trifluoroacetic acid (4 mL) for 3 min at 0° C. The volatiles were removed in vacuo. The non-polar residues were removed by washing with ether/methanol (1%) mixture and decanted the solvent to get carbamate derivative as TFA salt.

4,3',4',2'',5''3''',4''''-Hepta-O-phenylcarbamoyl-1,3,2', 6',2''',6'''-hexa-N-(tert-butoxycarbonyl)-5''-deoxyneomycin (3A)

Yield=87%; R$_f$ 0.55 (CH$_2$Cl$_2$/MeOH 15:1); $^1$H NMR (500 MHz, Pyridine-d$_5$): δ 7.95 (d, 1H, J=7.8 Hz), 7.81 (d, 5H, J=8.1 Hz), 7.77 (d, 4H, J=6.9 Hz), 7.72 (m, 8H), 7.29 (m, 9H), 7.03 (t, 3H, J=7.4 Hz), 7.04 (m, 4H), 6.77 (br s, 1H), 6.37 (br d, 1H, J=4.2 Hz), 5.84 (t, 2H, J=9.6 Hz), 5.50 (t, 2H, J=9.6 Hz), 5.37 (m, 4H), 5.21 (br s, 2H), 4.61 (d, 2H, J=9.6 Hz), 4.42 (t, 2H, J=9.1 Hz), 4.32 (m, 1H), 4.10 (m, 5H), 4.01 (t, 2H, J=9.6 Hz), 3.69 (d, 2H, J=12.3 Hz), 2.50 (d, 1H, J=12.2 Hz), 1.89 (q, 1H, J=12.2 Hz), 1.51 (s, 12H), 1.42 (2 s, 30H), 1.21 (s, 12H); $^{13}$C NMR (75 MHz, CD$_3$OD): δ 158.4, 158.3, 157.8, 157.7, 157.6, 155.5, 155.4, 154.8, 154.5, 153.8, 153.3, 140.5, 139.9, 139.8, 139.6, 130.1, 129.9, 129.8, 129.7, 124.4, 124.3, 123.8, 120.5, 120.4, 120.0, 109.4, 99.6, 98.9, 84.8, 81.8, 80.9, 80.5, 80.4, 78.1, 76.6, 75.9, 73.8, 72.3, 71.7, 70.8, 65.1, 61.5, 55.3, 51.6, 50.5, 49.8, 47.0, 41.4, 35.4, 29.1, 28.9, 28.8, 28.7, 28.6, 28.3; [α]$_D^{25}$=+45.0 (c 1.6, MeOH); EIMS: calcd. for C$_{102}$H$_{129}$N$_{13}$NaO$_{32}^+$ 2070.87. Found: 2071.45 [M+Na]$^+$.

1,3,2',6',2''',6'''-Hexaammonium-4,3',4',2'',5''3''',4''''-hepta-β-phenylcarbamoyl-5''-deoxy-neomycin-hexafluoroacetate (4A)

Yield=91%; R$_f$ 0.48 (CH$_2$Cl$_2$/MeOH/NH$_4$OH, 5:4:1); $^1$H NMR (300 MHz, CD$_3$OD): δ 7.72 (d, 2H, J=8.1 Hz), 7.69 (d, 2H, J=7.9 Hz), 7.47 (d, 3H, J=8.2 Hz), 7.42 (m, 5H), 7.30 (m, 7H), 7.23 (m, 5H), 7.04 (m, 4H), 6.90 (t, 2H, J=7.5 Hz), 6.81 (t, 2H, J=7.5 Hz), 6.66 (t, 1H, J=7.5 Hz), 6.50 (t, 2H, J=7.5 Hz), 5.77 (br s, 1H), 5.75 (t, 2H, J=9.6 Hz), 5.42 (br s, 1H), 5.26 (br s, 1H), 5.13 (br d, 2H, J=4.2 Hz), 5.02 (m, 4H), 4.69 (t, 1H, J=9.6 Hz), 4.48 (t, 1H, J=9.1 Hz), 4.37 (m, 3H), 4.29 (m, 4H), 3.69 (m, 2H), 3.32 (m, 2H), 3.13 (d, 1H, J=12.2 Hz), 2.63 (br d, 1H, J=5.3 Hz), 2.29 (m, 1H); $^{13}$C NMR (75 MHz, CD$_3$OD): δ 164.0-162.7 (TFA carbons, q with J$^1_{CF}$~34.8 Hz), 155.4, 154.3, 154.2, 154.1, 153.4, 152.9, 140.1, 139.4, 139.2, 139.1, 130.7, 130.4, 130.1, 130.0, 129.9, 129.8, 129.5, 124.8, 124.7, 124.1-112.4 (TFA carbons, q with J$^1_{CF}$~292.0 Hz), 123.6, 120.3, 119.7, 118.9, 116.2, 111.6, 96.9, 94.7, 85.5, 80.1, 76.2, 75.9, 75.6, 75.1, 72.6, 72.1, 71.9, 70.2, 68.7, 68.3, 67.4, 53.9, 50.7, 41.5, 39.9, 29.6; [α]$_D^{25}$=+29 (c 0.4, MeOH); EIMS: calcd. for C$_{72}$H$_{82}$N$_{13}$O$_{20}^+$ 1448.57. Found: 1448.15 [M+H]$^+$.

6,3',4',2'',5'',4'''-Hexa-O-phenylcarbamoyl-1,3,2',6', 2''',6'''-hexa-N-(tert-butoxycarbonyl)-5''-hexadecanoyl-5''-deoxy-neomycin (6A)

Yield=87%; R$_f$ 0.45 (CH$_2$Cl$_2$/MeOH 17:1); $^1$H NMR (300 MHz, CD$_3$OD): δ 7.72 (m, 2H), 7.60 (m, 5H), 7.50 (m, 3H), 7.43 (m, 2H), 7.30 (m, 13H), 7.15 (m, 3H), 7.04 (m, 2H), 6.09 (br s, 1H), 5.60 (br s, 1H), 5.20 (m, 2H), 4.98 (m, 2H), 4.90 (m, 2H), 4.60 (m, 1H), 4.32 (m, 1H), 4.15 (m, 3H), 3.90 (m, 6H), 3.69 (m, 1H), 3.52 (m, 2H), 3.20 (m, 3H), 2.31 (m, 2H), 1.70 (m, 2H), 1.47 (s, 54H), 1.29 (s, 26H), 0.88 (t, 3H, J=7.5 Hz); $^{13}$C NMR (75 MHz, CD$_3$OD): δ 176.3, 158.4, 158.0, 157.4, 156.7, 156.2, 155.5, 154.5, 152.9, 152.7, 140.0, 139.7, 138.9, 138.8, 138.6, 138.0, 131.1, 130.3, 130.2, 130.0, 129.8, 125.5, 124.3, 121.4, 121.2, 119.5, 110.1, 99.2, 98.1, 87.4, 83.4, 82.8, 80.6, 80.5, 78.7, 76.3, 73.4, 71.7, 71.3, 70.1, 69.7, 54.7, 51.1, 50.0, 43.8, 41.0, 37.7, 33.1, 30.9, 30.8, 30.6, 30.5, 29.0, 28.8, 28.7, 23.8, 14.6; [α]$_D^{25}$=+53.0 (c 0.35, MeOH); EIMS: calcd. for C$_{111}$H$_{155}$N$_{13}$NaO$_{31}^+$ 2189.08. Found: 2189.15 [M+Na]$^+$.

1,3,2',6',2''',6'''-Hexaammonium-6,3',4',2'',5'',4'''-hexa-β-phenylcarbamoyl-5''-hexadecanoyl-5''-deoxy-neomycin-hexafluoroacetate (7A)

Yield=89%; R$_f$ 0.58 (CH$_2$Cl$_2$/MeOH/NH$_4$OH 5:4:1); $^1$H NMR (300 MHz, acetone-d$_6$): δ 7.50 (m, 2H), 7.44 (m, 3H), 7.40 (m, 2H), 7.40 (m, 4H), 7.36 (m, 3H), 7.32-7.24 (m, 12H), 7.11 (m, 4H), 6.09 (br s, 1H), 5.60 (br s, 1H), 5.36 (br s, 1H), 5.22 (m, 2H), 5.05 (m, 1H), 4.49 (m, 2H), 4.22 (m, 3H), 3.99 (m, 2H), 3.74 (m, 1H), 3.60 (m, 3H), 3.45 (m, 4H), 3.27 (m, 2H), 3.22 (m, 2H), 2.48 (m, 1H), 2.27 (m, 2 H), 1.67 (m, 1H), 1.29 (s, 26H), 0.88 (t, 3H, J=7.5 Hz); $^{13}$C NMR (75 MHz, CD$_3$OD): δ 176.3, 164.0-162.7 (TFA carbons, q with J$^1_{CF}$~34.8 Hz), 155.9, 154.5, 152.6, 154.4, 152.7, 140.0, 139.5, 138.7, 138.2, 138.0, 131.1, 130.3, 130.2, 130.0, 129.8, 125.6, 124.7, 124.1-112.4 (TFA carbons, q with J$^1_{CF}$~292.0 Hz), 121.2, 120.1, 119.5, 116.1, 105.2, 102.7, 96.2, 80.6, 80.5, 78.7, 76.3, 72.9, 70.4, 69.7, 61.6, 58.3, 54.7, 51.1, 50.0, 43.8, 41.0, 37.7, 33.1, 30.9, 30.8, 30.6, 30.5, 29.0, 28.8, 23.8, 14.6; [α]$_D^{25}$=+33.0 (c 0.3, MeOH); EIMS: calcd. for C$_{81}$H$_{108}$N$_{13}$O$_{19}^+$ 1566.78. Found: 1566.67 [M+H]$^+$.

4,3',4',2'',5''3''',4''''-Hepta-O-phenylcarbamoyl-1,3,2', 6',2''',6'''-hexa-N-((N',N'-tert-butoxycarbonyl)-guanidinyl)-5''-deoxy-neomycin (8A)

Yield=77%; R$_f$ 0.35 (CH$_2$Cl$_2$/MeOH 12:1); $^1$H NMR (500 MHz, CD$_3$OD): δ 7.62 (d, 1H, J=7.8 Hz), 7.50 (d, 1H, J=8.1 Hz), 7.40 (m, 3H), 7.34 (m, 6H), 7.27-7.14 (m, 16H), 7.05 (t, 4H, J=8.1 Hz), 7.00 (d, 3H, J=8.1 Hz), 6.68 (m, 1H), 5.97 (br s, 1H), 5.59 (br s, 1H), 5.22 (m, 1H), 5.16 (m, 1H), 5.09 (m, 1H), 5.04 (m, 1H), 4.79 (m, 2H), 4.71 (m, 1H), 4.59 (m, 1H), 4.42 (m, 1H), 4.32 (m, 2H), 4.19 (m, 3H), 4.04 (m, 3H), 3.80 (m, 1H), 3.52 (m, 3H), 3.08 (m, 2H), 2.35 (m, 1H), 1.80 (m, 1H), 1.60 (s, 9H), 1.59 (s, 12H), 1.52 (3 s, 12H), 1.48 (s, 49H), 1.36 (s, 26H); $^{13}$C NMR (75 MHz, CD$_3$OD): δ 169.4, 164.4, 163.3, 157.8, 157.7, 157.6, 157.3, 157.0, 155.2, 154.8, 154.6, 154.0, 153.8, 153.6, 153.2, 140.0, 139.7, 139.5, 139.4, 139.3, 130.0, 130.1, 129.9, 129.8, 129.7, 129.6, 124.7, 124.0, 120.5, 120.1, 119.5, 108.6, 98.8, 98.6, 84.9, 84.8, 84.7, 84.6, 83.9, 81.1, 80.9, 80.6, 80.5, 76.9, 76.8, 75.6, 73.1, 69.9, 69.8, 69.7, 64.1, 61.5, 55.3, 51.0, 50.9, 41.9, 35.0, 31.2, 30.7, 28.8, 28.4, 28.3, 28.2; [α]$_D^{25}$=+43.0 (c 0.55, MeOH); EIMS: calcd. for C$_{138}$H$_{189}$N$_{25}$O$_{44}$ 2900.33. Found: 1473.70 (M/2+Na)$^+$.

4,3',4',2'',5''3''',4''''-Hexa-O-phenylcarbamoyl-1,3,2', 6',2''',6'''-hexa-N-(guanidinyl)-5''-deoxy-neomycin-hexafluoroacetate (9A)

Yield=88%; R$_f$ 0.19 (CH$_2$Cl$_2$/MeOH/NH$_4$OH, 5:5:2); $^1$H NMR (500 MHz, CD$_3$OD): δ 7.54 (t, 4H, J=8.4 Hz), 7.41 (t, 4H, J=7.5 Hz), 7.37 (t, 7H, J=7.8 Hz), 7.21 (m, 4H), 7.11 (t, 2H, J=7.5 Hz), 7.10 (m, 5H), 6.94 (m, 2H), 6.80 (t, 1H, J=7.5 Hz), 6.65 (d, 1H, J=7.8 Hz), 6.16 (d, 1H, J=3.2 Hz), 5.62 (br s, 1H), 5.47 (t, 1H, J=7.9 Hz), 5.15 (s, 1H), 5.08 (d, 1H, J=5.6 Hz), 5.00 (m, 1H), 4.97 (m, 1H), 4.92 (m, 1H), 4.82 (m, 1H), 4.76 (m, 1H), 4.32 (m, 4H), 4.12 (t, 1H, J=9.0 Hz), 4.04 (m, 3H), 3.76 (m, 1H), 3.64 (m, 1H), 3.57-3.54 (m, 3H), 3.08 (br d, 1H, J=13.3 Hz), 2.24 (br d, 1H, J=12.2 Hz), 1.92 (q, 1H, J=12.2 Hz); $^{13}$C NMR (75 MHz, CD$_3$OD): δ 164.0-162.7 (TFA carbons, q with $J^1_{CF}$~34.8 Hz), 159.4, 158.9, 158.6, 158.4, 157.4, 155.5, 154.8, 154.6, 154.2, 153.6, 139.7, 139.5, 139.4, 139.3, 130.2, 130.0, 129.9, 129.8, 129.7, 129.6, 124.7, 124.2, 124.1-112.4 (TFA carbons, q with $J^1_{CF}$~292.0 Hz), 120.3, 120.1, 119.7, 111.2, 98.8, 96.2, 82.9, 80.9, 78.6, 75.6, 73.1, 70.2, 68.2, 54.2, 52.0, 51.8, 50.9, 42.8, 33.6, 29.9; $[α]_D^{25}$=+45.0 (c 0.02, MeOH); EIMS: calcd. for $C_{78}H_{94}N_{25}NaKO_{20}^+$ 1700.71. Found: 1772.71 (M+K+Na)$^+$.

5,2",4",6",2"',3"',4"'-Hepta-O-phenylcarbamoyl-1,3, 6',3"-tetra-N-(tert butoxycarbonyl)-6"-deoxy-kanamycin (10A)

Yield=85%; R$_f$ 0.51 (CH$_2$Cl$_2$/MeOH 15:1); $^1$H NMR (300 MHz, CD$_3$OD): δ 7.94 (m, 5H), 7.83 (m, 2H), 7.74 (d, 2H, J=6.9 Hz), 7.64 (t, 2H, J=6.3 Hz), 7.52 (m, 2H), 7.40 (m, 6H), 7.27 (m, 4H), 7.12 (m, 6H), 7.01 (m, 3H), 6.94 (m, 2H), 6.75 (m, 1H), 5.60 (s, 1H), 5.58 (t, 1H, J=9.8 Hz), 5.20 (br d, 2H, J=25.2 Hz), 5.03 (m, 3H), 4.72 (d, 3H, J=8.2 Hz), 4.50 (br d, 3H, J=25.2 Hz), 4.04 (m, 2H), 3.78 (m, 3H), 3.20 (br s, 1H), 2.23 (m, 1H), 1.70 (m, 1H), 1.44 (2 s, 27H), 1.21 (s, 9H); $^{13}$C NMR (75 MHz, CD$_3$OD): δ 173.0, 158.3, 157.8, 157.3, 155.0, 154.1, 139.9, 139.8, 139.6, 139.0, 130.4, 130.1, 129.9, 129.7, 129.4, 129.2, 124.6, 124.2, 123.6, 120.6, 120.3, 119.7, 99.7, 96.9, 81.1, 80.8, 80.6, 80.4, 71.7, 71.2, 70.0, 65.0, 53.5, 52.6, 51.1, 41.4, 36.9, 29.0, 28.7, 28.4; $[α]_D^{25}$=+38.0 (c 1.35, MeOH); EIMS: calcd. for $C_{87}H_{103}NaN_{11}O_{26}^+$ 1740.69. Found: 1740.46 (M+Na)$^+$.

1,3,6',3"-Tetraammonium-5,2",4",6",2"',3"',4"'-hepta-β-phenylcarbamoyl-6"-deoxy-kanamycin-tetrafluoroacetate (11A)

Yield=89%; R$_f$ 0.55 (CH$_2$Cl$_2$/MeOH/NH$_4$OH, 5:5:1); $^1$H NMR (300 MHz, CD$_3$OD): δ 7.54 (d, 3H, J=7.9 Hz), 7.39 (t, 8H, J=6.3 Hz), 7.33 (t, 4H, J=8.0 Hz), 7.25 (m, 2H), 7.16 (m, 6H), 7.09 (m, 3H), 7.01 (m, 5H), 6.87 (t, 2H, J=7.7 Hz), 6.64 (t, 2H, J=7.2 Hz), 5.48 (d, 1H, J=3.0 Hz), 5.40 (t, 1H, J=8.9 Hz), 5.17 (dd, 1H, J=10.2, 3.9 Hz), 5.11 (br s, 1H), 5.01 (dd, 1H, J=10.5, 3.8 Hz), 4.99 (d, 1H, J=9.8 Hz), 4.44 (t, 2H, J=9.8 Hz), 4.31 (m, 2H), 4.17 (t, 2H, J=12.0 Hz), 3.87 (t, 1H, J=3.0 Hz), 3.85 (m, 3H), 3.47 (t, 2H, J=9.9 Hz), 3.22 (dd, 1H, J=7.5, 15.4 Hz), 2.44 (m, 1H), 2.06 (m, 1H); $^{13}$C NMR (75 MHz, CD$_3$OD): δ 164.0-162.7 (TFA carbons, q with $J^1_{CF}$~34.8 Hz), 154.9, 154.7, 154.2, 154.1, 153.9, 139.9, 139.4, 139.1, 129.9, 129.8, 129.7, 129.6 124.6, 124.5, 124.3, 124.1-112.4 (TFA carbons, q with $J^1_{CF}$~292.0 Hz), 120.4, 120.0, 99.8, 98.1, 82.4, 72.2, 71.9, 71.4, 70.9, 69.2, 52.5, 50.6, 49.9, 49.6, 49.3, 49.1, 48.8, 48.4, 48.2, 29.2; $[α]_D^{25}$=+22.1 (c 1.2, MeOH); EIMS: calcd. for $C_{67}H_{71}N_{11}O_{18}^+$ 1318.50. Found: 1318.42 (M+H)$^+$.

5,2',4',2",3",4"-Hexa-O-phenylcarbamoyl-1,3,6',3"-tetra-N-(tert butoxycarbonyl)-6"-hexadecanoyl-6"-deoxy-kanamycin (13A)

Yield=85%; R$_f$ 0.46 (CH$_2$Cl$_2$/MeOH 17:1); $^1$H NMR (300 MHz, CD$_3$OD): δ 7.53 (d, 2H J=6.4 Hz), 7.44 (t, 3H J=6.9 Hz), 7.36 (t, 2H, J=8.1 Hz), 7.25 (m, 2H), 7.22 (dd, 3H, J=7.3 Hz), 7.17 (d, 2H, J=9.2 Hz), 7.13 (br d, 3H, J=10.1 Hz), 7.02 (m, 5H), 6.91 (m, 7H), 6.60 (t, 1H, J=6.2 Hz), 5.53 (br s, 1H), 5.43 (t, 2H, J=9.8 Hz), 5.17 (m, 3H), 4.99 (t, 2H, J=9.4 Hz), 4.68 (t, 2H, J=9.8), 4.21 (t, 3H, J=9.8 Hz), 3.96 (m, 1H), 3.74 (m, 4H), 3.22 (m, 2H), 2.72 (m, 1H), 2.26 (m, 1H), 2.06 (m, 1H), 1.66 (m, 2H), 1.47 (2 s, 24H), 1.26 (s, 36H), 0.90 (t, 3H, J=6.7 Hz); $^{13}$C NMR (75 MHz, CD$_3$OD): δ 175.9, 158.6, 157.8, 157.5, 157.3, 155.1, 155.0, 154.9, 154.7, 154.3, 154.1, 140.5, 140.2, 139.5, 139.3, 139.2, 138.8, 129.9, 129.8, 129.7, 129.6, 129.5, 129.2, 124.7, 124.5, 124.4, 124.1, 123.9, 123.6, 120.8, 120.5, 120.4, 120.0, 119.9, 99.3, 96.5, 80.9, 80.6, 80.1, 77.1, 72.8, 72.0, 71.9, 71.1, 70.5, 70.1, 53.0, 51.0, 41.3, 37.4, 36.5, 33.1, 30.8, 30.7, 30.4, 30.3, 27.0, 23.8, 14.5; $[α]_D^{25}$=+73.5 (c 0.65, MeOH); EIMS: calcd. for $C_{96}H_{129}N_{11}NaO_{25}^+$ 1858.90. Found: 1858.60 (M+Na)$^+$.

1,3,6',3"-Tetraammonium-5,2',4',2",3",4"-hexa-O-phenylcarbamoyl-6" hexadecanoyl-6"-deoxy-kanamycin-tetrafluoroacetate (14A)

Yield=91%; R$_f$ 0.54 (CH$_2$Cl$_2$/MeOH/NH$_4$OH, 5:4:1); $^1$H NMR (300 MHz, CD$_3$OD): δ 7.53 (d, 2H J=7.5 Hz), 7.44 (t, 4H J=6.9 Hz), 7.36 (t, 3H, J=7.9 Hz), 7.25 (m, 11H), 7.11 (dd, 3H, J=7.5 Hz), 7.00 (m, 6H), 6.88 (t, 1H, J=7.3 Hz), 5.52 (d, 1H, J=3.1 Hz), 5.43 (t, 1H, J=9.8 Hz), 5.17 (dd, 1H, J=3.4, 9.8 Hz), 5.09 (dd, 2H, J=2.9, 9.8 Hz), 4.81 (t, 2H, J=9.8), 4.45 (t, 1H, J=9.4 Hz), 4.35 (t, 1H, J=9.3 Hz), 4.26 (t, 1H, J=9.8 Hz), 4.02 (d, 1H, J=9.4 Hz), 3.80 (t, 2H, J=10.1 Hz), 3.61 (q, 1H, J=6.6 Hz), 3.46 (t, 1H, J=6.6 Hz), 3.33 (m, 2H), 3.21 (t, 1H, J=6.2 Hz), 3.13 (dd, 1H, J=4.8, 14.9 Hz), 2.72 (dd, 1H, J=4.3, 12.4 Hz), 2.34 (q, 1H, J=12.2 Hz), 1.90 (t, 1H, J=7.4 Hz), 1.36 (t, 1H, J=4.2 Hz), 1.29 (br s, 26H), 0.90 (t, 3H, J=6.7 Hz); $^{13}$C NMR (75 MHz, CD$_3$OD): δ 175.9, 164.0-162.7 (TFA carbons, q with $J^1_{CF}$~34.8 Hz), 155.5, 154.9, 154.7, 154.4, 154.3, 154.0, 140.5, 139.7, 139.5, 139.4, 139.3, 139.2, 130.0, 129.9, 129.8, 129.7, 124.8, 124.7, 124.5, 124.4, 124.1-112.4 (TFA carbons, q with $J^1_{CF}$~292.0 Hz), 123.9, 120.6, 120.5, 120.4, 120.3, 99.3, 97.9, 81.9, 77.1, 72.0, 71.9, 71.5, 69.2, 69.1, 58.4, 52.7, 52.6, 50.7, 50.4, 41.3, 39.2, 36.9, 33.1, 30.8, 30.7, 30.4, 30.3, 29.2, 26.7, 23.8, 14.5; $[α]_D^{25}$=+36.0 (c 0.15, MeOH); EIMS: calcd. for $C_{76}H_{98}N_{11}O_{17}^+$ 1436.71. Found: 1436.57 (M+H)$^+$.

1,3,2',6'-Tetra-N-(tert-butoxycarbonyl)neamine (15A)

A solution of neamine (1) (1.0 g, 1.626 mmol) in a mixture of MeOH (20 mL), water (4 mL) and triethylamine (2 mL) was treated with di-tert-butyldicarbonate (2.1 g, 9.75 mmol, 6.0 equiv). The reaction solution was stirred at rt. The volatiles were removed in vacuo. The residue was partitioned between water (30 mL) and ethyl acetate (60 mL). The aqueous layer was separated and extracted with ethyl acetate (2×25 mL). The combined organic layer was washed with brine, dried over Na$_2$SO$_4$, and concentrated in vacuo. Flash column chromatography afforded the desired product as a white solid (1.8 g, 91%). R$_f$ 0.36 (MeOH/CH$_2$Cl$_2$ 1:15); $^1$H NMR (300 MHz, CD$_3$OD): δ 5.27 (br s, 1H), 3.72 (m, 1H), 3.55 (m, 3H), 3.47 (d, 1H, J=3.2 Hz), 3.44 (d, 1H, J=3.2 Hz), 3.42 (d, 2H, J=5.3 Hz), 3.36 (m, 1H), 3.25 (m, 1H), 3.17 (t, 1H, J=9.3 Hz), 2.05 (m, 1H), 1.58 (m, 1H), 1.47 (3 s, 36H); $^{13}$C NMR (75 MHz, CD$_3$OD): δ 159.2, 158.6, 158.2, 157.8, 100.5, 82.1, 80.6, 80.3, 80.2, 78.9, 76.5, 72.9, 72.8, 72.3, 57.0, 52.4, 50.9, 47.9, 42.0, 36.2, 28.9, 28.8, 28.7, 28.1; $[α]_D^{25}$=+59.0 (c 0.2, MeOH); EIMS: calcd. for $C_{32}H_{58}N_4NaO_{14}^+$ 722.39. Found: 722.08 [M+Na]$^+$.

4,5,3',4'-Tetra-O-phenylcarbamoyl-1,3,2',6'-Tetra-N-(tert-butoxycarbonyl)neamine (16A)

Yield=86%; R$_f$ 0.51 (CH$_2$Cl$_2$/MeOH 15:1); $^1$H NMR (300 MHz, CD$_3$OD): δ 7.45 (d, 1H, J=8.7 Hz), 7.38 (d, 3H, J=9.2 Hz), 7.30 (m, 4H), 7.24 (m, 3H), 7.18 (m, 3H), 7.10 (d, 3H, J=7.7 Hz), 6.98 (t, 1H, J=7.7 Hz), 6.91 (dd, 2H, J=7.0, 14.0 Hz), 6.00 (br s, 1H), 5.56 (d, 1H, J=8.4 Hz), 5.16 (d, 1H, J=10.0 Hz), 5.06 (d, 1H, J=8.7 Hz), 4.82 (t, 1H, J=9.6 Hz), 4.80 (d, 1H, J=10.0 Hz), 4.03 (d, 1H, J=10.0 Hz), 3.92 (dt, 1H, J=3.9, 10.4 Hz), 3.75 (m, 3H), 3.13 (d, 1H, J=14.4 Hz), 2.18 (d, 1H, J=12.3 Hz), 1.53 (m, 1H), 1.47 (s, 26H), 1.30 (s, 10H); $^{13}$C NMR (75 MHz, CD$_3$OD): δ 157.1, 156.5, 155.5, 153.9, 153.5, 152.8, 137.8, 137.7, 128.8, 128.7, 128.6, 128.5, 123.4, 123.2, 123.1, 118.9, 118.4, 99.2, 80.3, 79.8, 77.5, 77.3, 77.1, 76.7, 75.3, 72.1, 70.1, 69.3, 60.5, 53.1, 49.8, 40.0, 35.0, 28.3, 28.2, 28.0; $[α]_D^{25}$=+48 (c 0.25, MeOH); EIMS: calcd. for C$_{60}$H$_{78}$N$_8$NaO$_{18}^+$ 1221.53. Found: 1221.31 [M+Na]$^+$.

1,3,2',6'-Tetraammonium-4,5,3',4'-tetra-O-phenylcarbamoyl-neamine-tetrafluoroacetate (17A)

Yield=89%; R$_f$ 0.50 (CH$_2$Cl$_2$/MeOH/NH$_4$OH, 5:4:1); $^1$H NMR (300 MHz, CD$_3$OD): δ 7.40 (d, 4H, J=7.6 Hz), 7.34 (t, 4H, J=7.2 Hz), 7.26 (m, 4H), 7.16 (m, 3H), 7.03 (m, 5H), 5.80 (d, 1H, J=3.2 Hz), 5.67 (t, 1H, J=8.5 Hz), 5.36 (t, 2H, J=9.4 Hz), 5.30 (t, 1H, J=9.4 Hz), 5.01 (t, 1H, J=8.0 Hz), 4.73 (t, 1H, J=9.2 Hz), 4.50 (m, 1H), 3.77 (m, 3H), 3.41 (d, 1H, J=4.7 Hz), 2.67 (m, 1H), 2.31 (m, 1H); $^{13}$C NMR (75 MHz, CD$_3$OD): δ 164.0-162.7 (TFA carbons, q with $J^1_{CF}$~34.8 Hz), 155.0, 154.4, 154.1, 153.9, 139.4, 139.3, 139.2, 138.8, 130.2, 129.9, 129.8, 129.7, 124.8, 124.6, 124.1-112.4 (TFA carbons, q with $J^1_{CF}$~292.0 Hz), 120.7, 120.4, 120.3, 120.2, 116.3, 94.7, 77.0, 75.8, 74.1, 71.0, 70.5, 69.8, 53.1, 50.1, 49.9, 40.9, 38.9, 29.5, 28.9; $[α]_D^{25}$=+32.4 (c 0.45, MeOH); EIMS: calcd. for C$_{40}$H$_{47}$N$_8$O$_{10}$ 799.34. Found: 799.07 [M+H]$^+$.

3,6',3'',1'''-Tetra-N-(tert-butoxycarbonyl)-amikacin (18A)

Yield=79%; R$_f$ 0.46 (CH$_2$Cl$_2$/MeOH 10:1); $^1$H NMR (300 MHz, CD$_3$OD): δ 5.14 (br d, 1H, J=4.2 Hz), 5.06 (br d, 1H, J=4.2 Hz), 4.07 (m, 1H), 4.01 (dd, 1H, J=3.6, 9.2 Hz), 3.87 (d, 2H, J=2.1 Hz), 3.79 (m, 3H), 3.75 (m, 2H), 3.66 (m, 3H), 3.52 (d, 2H, J=3.0 Hz), 3.48 (d, 3H, J=3.5 Hz), 3.40 (d, 1H, J=3.5 Hz), 3.20 (m, 3H), 2.99 (q, 1H, J=7.3 Hz), 2.13 (d, 1H, J=12.1 Hz), 1.97 (m, 1H), 1.78 (m, 1H) 1.58 (m, 1H), 1.47 (s, 36H); $^{13}$C NMR (75 MHz, CD$_3$OD): δ 177.1, 159.4, 158.5, 157.3, 102.8, 100.4, 84.9, 81.9, 80.5, 79.8, 77.4, 74.4, 73.9, 72.2, 71.6, 71.1, 70.1, 62.1, 57.1, 50.8, 35.4, 29.0, 28.9, 28.8, 27.9; $[α]_D^{25}$=+48.8 (c 0.7, MeOH); EIMS: calcd. for C$_{42}$H$_{75}$N$_5$NaO$_{21}$ 985.49. Found: 985.29 (M+Na)$^+$.

5,2',4',2'',3'',4''-Hexa-O-phenylcarbamoyl-3,6',3'',1'''-Tetra-N-(tert-butoxycarbonyl)-6''-deoxy-amikacin (19A)

Yield=82%; R$_f$ 0.56 (CH$_2$Cl$_2$/MeOH 15:1); $^1$H NMR (300 MHz, Pyridine-d$_5$): δ 7.98 (d, 2H J=8.0 Hz), 7.81 (d, 2H J=7.7 Hz), 7.84 (d, 2H, J=8.5 Hz), 7.74 (m, 3H), 7.65 (dd, 2H, J=8.0 Hz), 7.44 (q, 4H, J=8.3 Hz), 7.34 (m, 8H), 7.29 (m, 4H), 7.11 (m, 5H), 7.04 (m, 5H), 6.94 (m, 2H), 6.78 (m, 1H), 5.56 (m, 5H), 5.40 (m, 2H), 5.24 (m, 1H), 4.68 (m, 4H), 4.42 (m, 3H), 4.04 (m, 4H), 3.76 (m, 1H), 3.32 (m, 2H), 2.40 (m, 2H), 2.15 (m, 1H), 2.01 (m, 1H), 1.48 (4 s, 27H), 1.23 (s, 9H); $^{13}$C NMR (75 MHz, CD$_3$OD): δ 172.4, 157.4, 154.9, 154.2, 150.1, 140.5, 139.1, 130.3, 130.2, 130.1, 130.0, 129.9, 129.8, 129.8, 129.7, 129.5, 129.1, 124.3, 124.1, 123.9, 121.4, 120.6, 120.4, 119.9, 99.7, 96.4, 80.9, 80.7, 80.2, 78.1, 74.9, 71.9, 70.7, 70.2, 49.8, 37.6, 33.1, 28.9, 28.8, 28.6, 28.4, 28.0; $[α]_D^{25}$=+35.4 (c 0.4, MeOH); EIMS: calcd. for C$_{98}$H$_{115}$N$_{13}$NaO$_{29}^+$ 1960.78. Found: 1960.58 (M+Na)$^+$.

3,6',3'',1'''-Tetraammonium-5,2',4',2'',3'',4''-hexa-O-phenylcarbamoyl-6''-deoxy-amikacin-tetrafluoroacetate (20A)

Yield=87%; R$_f$ 0.55 (CH$_2$Cl$_2$/MeOH/NH$_4$OH, 5:4:1); $^1$H NMR (300 MHz, CD$_3$OD): δ 7.56 (d, 2H J=8.2 Hz), 7.54 (m, 2H), 7.44 (m, 5H), 7.35 (m, 8H), 7.24 (m, 10H), 7.13 (d, 2H J=7.3 Hz), 7.04 (m, 5H), 6.98 (m, 4H), 6.81 (t, 2H J=7.5 Hz), 5.74 (d, 1H, J=10.1 Hz), 5.32 (m, 2H), 5.18 (dd, 2H, J=3.4, 10.2 Hz), 5.02 (d, 2H, J=10.2 Hz), 4.39 (m, 2H), 4.36 (m, 1H), 4.27 (m, 2H), 4.16 (m, 2H), 3.67 (t, 1H, J=9.9 Hz), 3.58 (m, 1H), 3.42 (m, 3H), 3.18 (m, 2H), 3.10 (m, 1H), 2.62 (m, 1H), 2.32 (m, 1H), 2.21 (m, 2H); $^{13}$C NMR (75 MHz, CD$_3$OD): δ 172.2, 164.0-162.7 (TFA carbons, q with $J^1_{CF}$~34.8 Hz), 154.7, 153.8, 153.7, 139.6, 139.6, 139.4, 139.3, 130.3, 130.2, 130.1, 129.9, 129.8, 129.8, 129.7, 129.5, 124.4, 124.1-112.4 (TFA carbons, q with $J^1_{CF}$~292.0 Hz), 122.1, 120.7, 120.6, 120.5, 120.4, 98.6, 96.0, 76.9, 72.0, 71.4, 71.1, 69.0, 50.8, 50.7, 50.5, 50.4, 49.7, 41.6, 37.4, 36.6, 30.9, 28.4; $[α]_D^{25}$=+35.7 (c 0.1, MeOH); EIMS: calcd. for C$_{78}$H$_{54}$N$_{13}$O$_{21}^+$ 1538.58. Found: 1538.35 (M+H)$^+$.

4,3',4',2'',5''3''',4'''-Hepta-O-(4-Chloro-phenylcarbamoyl)-1,3,2',6',2''',6'''-hexa-N-(tert-butoxycarbonyl)-5''-deoxy-neomycin (21A)

Yield=78%; R$_f$ 0.59 (CH$_2$Cl$_2$/MeOH 15:1); $^1$H NMR (500 MHz, CD$_3$OD-d$_5$): δ 7.54 (d, 2H, J=7.8 Hz), 7.43 (m, 5H), 7.33 (m, 8H), 7.26 (m, 5H), 7.20 (m, 4H), 6.37 (m, 2H), 5.48 (br s, 1H), 5.18 (t, 1H, J=10.8 Hz), 5.07 (m, 2H), 4.99 (m, 2H), 4.72 (m, 3H), 4.65 (m, 1H), 4.59 (m, 1H), 4.23 (d, 1H, J=11.4 Hz), 4.10 (m, 6H), 3.81-3.70 (m, 3H), 3.49 (m, 2H), 3.21 (m, 2H), 1.98 (m, 1H), 1.67 (m, 1H), 1.42 (s, 54H); $^{13}$C NMR (75 MHz, CD$_3$OD): δ 158.4, 158.3, 157.8, 157.7, 157.4, 155.4, 154.6, 154.4, 153.8, 152.9, 138.9, 138.7, 138.6, 131.6, 130.4, 129.9, 129.8, 129.7, 122.6, 121.9, 121.5, 121.0, 119.9, 109.9, 99.3, 98.2, 85.7, 81.3, 80.5, 78.7, 76.6, 75.4, 73.8, 72.3, 70.5, 64.9, 55.0, 51.1, 50.5, 42.3, 41.1, 35.1, 30.7, 29.1, 28.9, 28.6; EIMS: calcd. for C$_{102}$H$_{122}$C$_{17}$N$_{13}$O$_{32}$Na$^+$ 2304.61. Found: 2304.78 (M+Na)$^+$.

1,3,2',6',2''',6'''-Hexaammonium-4,3',4',2'',5''3''',4'''-hepta-O-(4-Chloro-phenylcarbamoyl)-5''-deoxy-neomycin-hexafluoroacetate (22A)

Yield=88%; R$_f$ 0.46 (CH$_2$Cl$_2$/MeOH/NH$_4$OH, 5:4:1); $^1$H NMR (300 MHz, CD$_3$OD): δ 7.72 (d, 2H, J=8.0 Hz), 7.63 (d, 2H, J=8.3 Hz), 7.47 (d, 5H, J=8.2 Hz), 7.37 (m, 7H), 7.27 (m, 3H), 7.22 (m, 4H), 6.82 (m, 2H), 6.66 (br s, 1H), 6.50 (m, 1H), 5.77 (br s, 1H), 5.75 (s, 1H), 5.36 (m, 1H), 5.21 (br s, 1H), 5.07 (m, 3H), 4.81 (m, 3H), 4.69 (m, 2H), 4.55 (t, 1H, J=9.1 Hz), 4.44 (m, 1H), 4.21 (m, 4H), 3.80-3.57 (m, 4H), 3.22 (m, 2H), 3.15 (m, 1H), 2.55 (m, 1H), 2.26 (m, 1H); $^{13}$C NMR (75 MHz, CD$_3$OD): δ 164.0-162.7 (TFA carbons, q with $J^1_{CF}$~34.8 Hz), 155.2, 154.1, 153.8, 153.7, 153.3, 152.8, 152.5, 138.9, 138.7, 138.4, 138.2, 138.1, 137.9, 131.4, 131.0, 130.8, 130.6, 130.4, 129.9, 129.8, 129.5, 129.2, 124.1-112.4 (TFA carbons, q with $J^1_{CF}$~292.0 Hz), 121.4, 121.1, 120.8, 119.8, 111.4, 97.0, 94.4, 85.5, 79.8, 76.2, 75.9, 75.2, 74.8, 72.6, 72.5, 72.4, 70.2, 68.7, 68.3, 67.4, 53.9, 50.5, 41.3, 39.8, 29.6; EIMS: calcd. for C$_{72}$H$_{75}$C$_{17}$N$_{13}$O$_{20}^+$ 1686.30. Found: 1686.45 (M+H)$^+$.

4,3',4',2'',5''3''',4'''-Hepta-O-benzyloxy-1,3,2',6',2''',6'''-hexa-N-(tert-butoxycarbonyl)-5''-deoxy-neomycin (23A)

To a solution of compound 2 (1.0 g, 0.82 mmol) in DMF, Ba(OH)$_2$ (0.21 g, 20.6 mmol) was added and cooled to 0° C.

and then benzyl bromide (1.68 g, 9.84 mmol) was added and stirred at rt for 48 h. After completion of reaction the reaction mixture was filtered on celite and washed with ethylacetate. Removed the solvent at reduced pressure and the crude reaction mixture was purified through flush silica gel column chromatography to get 23. Yield=87%; $R_f$ 0.55 ($CH_2Cl_2$/MeOH 15:1); $^1$H NMR (500 MHz, Pyridine-$d_5$): δ 7.39 (d, 2H, J=7.8 Hz), 7.33 (m, 15H), 7.27 (m, 13H), 7.17 (m, 3H), 7.00 (m, 2H), 6.84 (d, 1H, J=10.2 Hz), 6.70 (d, 1H, J=10.2 Hz), 6.63 (d, 1H, J=10.2 Hz), 6.54 (br s, 1H), 5.96 (br s, 1H), 5.84 (br s, 1H), 5.71 (t, 2H, J=9.6 Hz), 5.17 (br s, 1H), 4.75 (m, 5H), 5.66 (m, 2H), 4.60 (m, 5H), 4.43 (t, 1H, J=7.4 Hz), 4.31 (t, 2H, J=13.3 Hz), 4.12 (m, 4H), 3.93 (m, 2H), 3.88 (m, 1H), 3.84 (d, 1H, J=3.5 Hz), 3.80 (t, 1H, J=5.6 Hz), 3.76 (br d, 1H, J=2.1 Hz), 3.75 (m, 1H), 3.63 (t, 3H, J=8.7 Hz), 3.52 (m, 3H), 3.46 (m, 2H), 3.21 (m, 2H), 1.85 (m, 1H), 1.55 (m, 1H), 1.42 (s, 54H); $^{13}$C NMR (75 MHz, $CD_3OD$): δ 158.4, 158.1, 157.8, 157.7, 140.2, 140.1, 139.8, 139.7, 129.6, 129.5, 129.4, 129.3, 128.9, 128.6, 111.4, 98.9, 97.8, 85.3, 83.6, 82.8, 82.6, 81.4, 80.9, 80.5, 80.4, 80.1, 78.4, 76.6, 76.1, 74.8, 74.0, 73.8, 73.4, 73.3, 71.2, 69.5, 56.1, 52.3, 50.8, 42.7, 36.0, 29.1, 28.9, 28.8; EIMS: calcd. for $C_{102}H_{136}N_6O_{25}Na^+$ 1867.95. Found: 1868.06 (M+Na)$^+$.

1,3,2',6',2''',6'''-Hexaammonium-4,3',4',2'',5''3''',4'''-hepta-O-benzyloxy-5''-deoxy-neomycin-hexafluoroacetate (24A)

Yield=91%; $R_f$ 0.49 ($CH_2Cl_2$/MeOH/$NH_4OH$, 5:4:1); $^1$H NMR (300 MHz, $CD_3OD$): δ 7.38 (m, 27H), 7.27 (m, 3H), 7.22 (m, 4H), 6.02 (t, 1H, J=10.2 Hz), 5.64 (m, 1H), 5.10 (br s, 1H), 5.08 (m, 2H), 4.99 (m, 1H), 4.88 (m, 1H), 4.83 (m, 1H), 4.78 (m, 1H), 4.73 (t, 1H, J=4.5 Hz), 4.69 (m, 2H), 4.63 (m, 1H), 4.54 (m, 2H), 4.49 (m, 2H), 4.46 (d, 1H, J=4.9 Hz), 4.33 (m, 2H), 4.28 (m, 2H), 4.10 (m, 3H), 3.99 (d, 1H, J=4.9 Hz), 3.82 (t, 1H, J=9.7 Hz), 3.77 (m, 1H), 3.46 (m, 3H), 3.23 (m, 2H), 3.04 (m, 2H), 2.90 (m, 1H), 2.51 (dt, 1H, J=4.3, 12.2 Hz), 2.19 (m, 1H), 1.42 (s, 54H); $^{13}$C NMR (75 MHz, $CD_3OD$): δ 164.0-162.7 (TFA carbons, q with $J^1_{CF}$~34.8 Hz), 139.4, 139.1, 139.0, 129.9, 129.5, 129.4, 129.3, 129.1, 124.1-112.4 (TFA carbons, q with $J^1_{CF}$~292.0 Hz), 120.1, 116.2, 109.1, 96.9, 94.7, 84.5, 83.3, 81.6, 76.6, 76.1, 75.9, 75.5, 74.6, 74.0, 72.5, 52.8, 51.5, 50.9, 50.1, 41.2, 41.1, 32.6; EIMS: calcd. for $C_{72}H_{89}N_6O_{13}{}^+$ 1245.64. Found: 1245.79 (M+H)$^+$.

Procedure for the Coupling Reaction:

To a solution of kanamycin amine 28A (1 eq.) in dry DMF, TBTU (2 equiv), hexadecanoic acid (1 eq) and DIPEA (3 equiv) were added and stirred at room temperature for 2 h. The reaction mixture was triturated with water and ethylacetate. The ethylacetate layer was washed with water, brine, dried over sodium sulfate and concentrated. The crude residue was purified using flash silica gel by eluting with MeOH/$CH_2Cl_2$. The spectroscopic data were given below.

General Procedure for Final Deprotection:

All of the BOC-protected aminoglycoside-based compounds were treated with 95% TFA for 3 min at 0° C. TFA was removed at reduced pressure. To the residue 2% methanol in ether was added and the solvent was decanted to get the solid kanamycin-lipid conjugate, kanamycin amine and neomycin amine and related compounds as salt. The spectroscopic data were given below.

1,3,6',3''-Tetra-N-(tert-butoxycarbonyl)-6''-azido-6''-deoxy-kanamycin A (26A)

$R_f$: 0.36 (MeOH/$CH_2Cl_2$ 1:12); IR (KBr disk) 2106.3 cm$^{-1}$ ($N_3$); $^1$H NMR (300 MHz, $CD_3OD$): δ 5.11 (br s, 1H), 5.10 (br s, 1H), 4.33 (d, 1H, J=9.8), 3.74 (d, 2H, J=9.8 Hz), 3.64 (t, 1H, J=9.2 Hz), 3.69 (dd, 1H, J=4.3, 11.5 Hz), 3.59 (m, 2H), 3.56 (d, 1H, J=2.5 Hz), 3.51 (d, 1H, J=2.5 Hz), 3.45 (dd, 2H, J=4.3, 11.5 Hz), 3.41 (d, 2H, J=3.8 Hz), 3.38 (t, 3H, J=3.6 Hz), 3.21 (t, 1H, J=9.4 Hz), 2.09 (br d, 1H, J=12.2 Hz), 1.55 (m, 1H), 1.47 (2 s, 36H); $^{13}$C NMR (75 MHz, $CD_3OD$): δ 156.4, 155.6, 154.9, 101.4 (anomeric), 97.6 (anomeric), 84.6, 79.6, 78.0, 75.1, 72.7, 72.2, 71.2, 70.4, 70.1, 68.2, 55.5, 50.7, 49.9, 49.1, 40.8, 34.7, 27.9, 27.6; EIMS: calcd for $C_{38}H_{67}N_4NaO_{18}{}^+$ 932.44. Found: 932.38 [M+Na]$^+$.

1,3,6',3''-Tetra-N-(tert-butoxycarbonyl)-6''-amino-6''-deoxy-kanamycin A (27A)

The solution of kanamycin azide (500 mg, 0.549 mmol) and 10% Pd(OH)$_2$/C in methanol (25 mL) was hydrogenated at normal temperature and pressure for 4 h and then filtered through celite. Filtrate was concentrated and the residue was purified on flush column chromatography by using MeOH/$CH_2Cl_2$ (1:9) to afford 19A (411 mg, 85%), as a white solid. $^1$H NMR (300 MHz, $CD_3OD$-$d_6$): δ 5.06 (d, 1H, J=3.2 Hz), 5.03 (d, 1H, J=3.5 Hz), 4.52 (m, 1H), 4.34 (m, 1H), 4.23 (t, 1H, J=10.6 Hz), 4.03 (d, 1H, J=10.6 Hz), 3.80 (m, 1H), 3.72 (m, 1H), 3.69 (m, 1H), 3.66 (m, 1H), 3.62 (m, 2H), 3.52 (m, 2H), 3.46 (m, 1H), 3.42 (m, 2H), 3.22 (t, 1H, J=10.0 Hz), 3.00 (q, 1H, J=10.0 Hz), 2.10 (m, 1H), 1.52 (m, 1H), 1.46 (2 s, 36H); $^{13}$C NMR (75 MHz, $CD_3OD$): δ 159.2, 158.7, 157.6, 157.2, 123.2, 102.5, 99.8, 87.4, 85.9, 83.1, 80.4, 74.0, 73.4, 72.0, 71.2, 70.7, 69.7, 56.8, 51.6, 50.4, 41.4, 35.4, 28.9, 28.8; EIMS: calcd. for $C_{38}H_{70}N_5O_{18}$ 884.47. Found: 884.44 (M+H)$^+$.

6''-N-(Hexadecanoyl)-1,3,6',3''-tetra-N-(tert-butoxycarbonyl)-6''-deoxy-kanamycin (28A)

Yield=87%; $R_f$ 0.31 (MeOH/$CH_2Cl_2$ 1:15); $[α]_D^{25}$=50.0 (c 0.7, MeOH); $^1$H NMR (300 MHz, $CD_3OD$): δ 5.09 (d, 1H J=2.5 Hz), 5.04 (d, 1H J=3.5 Hz), 4.21 (t, 1H, J=8.2 Hz), 3.71 (dd, 1H, J=9.6, 16.6 Hz), 3.64 (d, 3H, J=9.4 Hz), 3.58 (t, 2H, J=7.7 Hz), 3.54-3.36 (m, 8H), 3.24 (d, 1H, J=9.3 Hz), 3.19 (t, 1H, J=9.0 Hz), 2.23 (t, 2H, J=7.7 Hz), 2.06 (br d, 1H, J=11.2 Hz), 1.62 (m, 3H), 1.47 (2 s, 36H), 1.26 (s, 24H), 0.90 (t, 3H, J=6.7 Hz); $^{13}$C NMR (75 MHz, $CD_3OD$): δ 176.7, 159.3, 159.1, 158.0, 157.7, 102.9 (anomeric), 100.3 (anomeric), 86.2, 81.8, 80.6, 80.4, 80.1, 77.1, 74.6, 74.0, 72.4, 72.1, 72.0, 71.8, 71.3, 57.4, 52.3, 50.9, 42.1, 41.9, 37.3, 35.9, 33.1, 30.9, 29.0, 28.9, 27.0, 23.8, 14.6; EIMS: calcd. for $C_{54}H_{99}N_5NaO_{19}{}^+$ 1141.68. Found: 1141.57 (M+Na)$^+$.

Example 5

Human Treatment with Aminoglycoside-Hydrophobe Conjugates

This example describes an exemplary protocol to facilitate the treatment of a bacterial infection in a patient using an aminoglycoside-hydrophobe conjugate. Patients may, but need not, have received previous anti-bacterial treatment.

A composition of the present invention is typically administered orally or topically in dosage unit formulations containing standard, well known non-toxic physiologically acceptable carriers, adjuvants, and/or vehicles as desired. The term "parenteral" as used herein includes subcutaneous injections, intravenous, intramuscular, intra-arterial injection, or infusion techniques. Aminoglycoside-hydrophobe conjugates may be delivered to the patient before, after, or concurrently with any other anti-bacterial agent(s), if desired.

A typical treatment course comprises dosing over a 7-14 day period. Dosing may include 1-3 dosages per day (e.g., swallowing of a pill comprising a compound of the present invention three times a day). Upon election by the clinician, the regimen may be continued for days or weeks on a more frequent or less frequent basis (e.g., twice a day, four times a day, etc.) basis. Of course, these are only exemplary times for treatment, and the skilled practitioner will readily recognize that many other time-courses are possible.

To treat a bacterial infection using the methods and compositions described in the present invention, one will generally contact a target bacteria with an aminoglycoside-hydrophobe conjugate. These compositions are provided in an amount effective to treat the infection, or, at a minimum, decrease side effects associated with the infection.

Regional delivery of an aminoglycoside-hydrophobe conjugate is an efficient method for delivering a therapeutically effective dose to counteract the bacterial. Alternatively systemic delivery of an aminoglycoside-hydrophobe conjugate may be appropriate. A therapeutic composition of the present invention may be administered to the patient directly at the site of the infection. This is in essence a topical treatment of the surface of the infection. The volume of the composition comprising the an aminoglycoside-hydrophobe conjugate should usually be sufficient to ensure that the infection is contacted by the aminoglycoside-hydrophobe conjugate.

Clinical responses may be defined by acceptable measure. For example, a complete response may be defined by the disappearance of all measurable infection for at least a month. A partial response may be defined by a 50% or greater reduction of the number of excess white blood cells, wherein excess white blood cells is defined as an amount of white blood cells that exceeds a normal range.

Of course, the above-described treatment regimes may be altered in accordance with the knowledge gained from clinical trials, such as those described in Example 5. Those of skill in the art are able to take the information disclosed in this specification and optimize treatment regimes based on the results from the trials.

Example 6

Clinical Trials of the Use of Aminoglycoside-Hydrophobe Conjugates in Treating Bacterial Infections This example is concerned with the development of human treatment protocols using an aminoglycoside-hydrophobe conjugate. These conjugates are of use in the clinical treatment of various bacterial infections in which infectious bacteria, such as multi-drug resistant infectious bacteria, play a role.

The various elements of conducting a clinical trial, including patient treatment and monitoring, are known to those of skill in the art in light of the present disclosure. The following information is being presented as a general guideline for studying aminoglycoside-hydrophobe conjugates in clinical trials.

Patients with a bacterial infection, such as a bacterial infection of the abdomen, urinary tract, blood (bacteremia), heart (endocarditis), or an infection on the skin are chosen for clinical study. Administration of an aminoglycoside-hydrophobe conjugate may be orally or topically. The starting dose may be 5 mg/kg body weight. Three patients may be treated at each dose level. Dose escalation may be done by 100% increments (5 mg, 10 mg, 20 mg, 40 mg) until drug related toxicity is detected. Thereafter, dose escalation may proceed by 25% increments, if at all, depending on the tolerance of the patient.

The aminoglycoside-hydrophobe conjugate may be administered over a 7 to 14 day period. The aminoglycoside-hydrophobe conjugate may be administered alone or in combination with, for example, another anti-bacterial agent. The infusion given at any dose level is dependent upon the toxicity achieved after each. Increasing doses of the aminoglycoside-hydrophobe conjugate in combination with an anti-bacterial agent is administered to groups of patients until approximately 60% of patients show unacceptable toxicity in any category. Doses that are $\frac{2}{3}$ of this value could be defined as the safe dose.

Physical examination, visual assessment of the infection site and laboratory tests (e.g., white blood cell counts) should, of course, be performed before treatment and at intervals of about 3-4 weeks later. Laboratory studies should include CBC, differential and platelet count, urinalysis, SMA-12-100 (liver and renal function tests), and any other appropriate chemistry studies to determine the extent of the infection, or determine the cause of existing symptoms.

Clinical responses may be defined by acceptable measure. For example, a complete response may be defined by the disappearance of all measurable infection for at least a month. A partial response may be defined by a 50% or greater reduction of the number of excess white blood cells, wherein excess white blood cells is defined as an amount of white blood cells that exceeds a normal range.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference.

U.S. Provisional Appl. No. 61/079,338
Baker et al., *J. Org. Chem.*, 65:9054-9058, 2000.
Begg and Barclay, *Br. J. Clin. Pharmacol.*, 39:597-603, 1995.
Biehl, *Vet. Clin. North. Am. Food Anim. Pract.*, 2:481-488, 1986.
Botto and Coxon, *J. Am. Chem. Soc.*, 105:1021-1028, 1983.
Bunin, In: *The Combinatorial Index*, Academic Press, 1998.
Chen et al., *Biochemistry*, 36:11402-11407, 1997.
Clinical and Laboratory Standards Institute, M100-S16. CLSI/NCCLS M100-S15, 2006.
Clouet-d'Orval et al., *Biochemistry*, 32:11186-11190, 1995.
Constantinou-Kokotou et al., *Bioorg. Med. Chem. Lett.*, 11:1015-1018, 2001.
Czarnik and De Witt, In: *A Practical Guide to Combinatorial Chemistry*, American Chemical Society, 1-360, 1997.

Disney and Barrett, *Biochem.*, 46:11223-11230, 2007.
Dorman et al., *J. Am. Chem. Soc.* 98:6885-6888, 1976.
Evans et al., *J. Amer. Chem. Soc.*, 112:4011-4030, 1990.
Gordon et al., *J. Med. Chem.*, 37:1233-1252; 1386-1401, 1994.
Greene and Wuts, In: *Protective Groups in Organic Synthesis*, 2nd Ed.; Wiley, NY, 1999.
Haddad et al., In: *Glycochemistry Principles, Synthesis, and Application*, Wang et al. (Eds.), Marcel Dekker, NY, 307-424, 2001.
*Handbook of Pharmaceutical Salts: Properties, Selection and Use* (P. H. Stahl & C.
G. Wermuth eds., Verlag Helvetica Chimica Acta, 2002
Hayes and Wolf, *Biochem. J.*, 272:281-295, 1990.
Hooper, In: Aminoglycoside Antibiotics, Springer-Verlag, NY, 1982.
Jacoby and Archer, *J. Med.*, 324:601-612, 1991.
Kirk et al., *J. Am. Chem. Soc.*, 122:980-981, 2000.
Kudyba et al., *Carb. Res.*, 342:499-519, 2007.
Mei et al., *Bioorg. Med. Chem. Chem. Lett.*, 5:2755-2760, 1995.
Michael et al., *Bioorg. Med. Chem.*, 7:1361-1371, 1999.
Mingeot-Leclercq and Tulkens, *Antimicrob. Agent. Chemother.*, 43:1003-1012, 1999.
Mingeot-Leclercq et al., *Antimicrob. Agent. Chemother.*, 43:727-737, 1999.
Moazed and Noller, *Nature*, 327:389-394, 1987.
Nakagawa et al., *J. Antibiot.*, 40:1627-1635, 1987.
Neu, *Science*, 257:1064-1073, 1992.
Ohyama et al., *Chem. Commun.*, 467-468, 1998.
Pu et al., *J. Amer. Chem. Soc.*, 56:1280-1283, 1991.
Purohit and Stern, *Nature*, 370:659-662, 1994.
Quader et al., *J. Org. Chem.*, 72:1962-1979, 2007.
Remington's Pharmaceutical Sciences, 18th Ed., 1289-1329, Mack Printing Company, 1990.
Sangster, In: *Octanol-Water Partition Coefficients: Fundamentals and Physical Chemistry*, Wiley Series in Solution Chemistry, Chichester: John Wiley & Sons Ltd., 2:178 pages, 1997.
Schwarz et al., *J. Antimicrob. Chemother.*, 53:379-382, 2004.
Shelburne et al., *Antimicrobial Agents Chemo.*, 48:4016-4019, 2004.
Sitaram and Nagaraj, *Curr. Pharm. Des.*, 8:727-742, 2002.
Smith and March's Advanced Organic Chemistry: Reactions, Mechanisms, and Structure (March's Advanced Organic Chemistry), 2001.
Taber et al., *Microbiol. Rev.*, 429-457, 1987.
Terret et al., *Tetrahedron*, 51:8135-8173, 1995.
Tohma et al., *J. Antibiotics*, 671-674, 1980.
Umezawa and Hooper, In: *Aminoglycoside Antibiotics*, Springer-Verlag, NY, Heidelberg, 1982.
Vieira and Carmona-Ribeiro, *J. Antimicrobial Chemo.*, e-published Aug. 2, 2006, JAC Advance Access, doi: 10.1093/jac/dk1312.
Von Ahsen and Noller, *Science*, 260:1500-1503, 1993.
Walsh, *Nature*, 406:144-145, 2000.
Wang and Tor, *J. Am. Chem. Soc.*, 119:8734-8735, 1997.
Werstuck et al., *Chem. Biol.*, 3:129-137, 1996.
Williams et al., *Mol. Cell. Biol.*, 9:2574, 1989.
Williams et al., *J. Amer. Chem. Soc.*, 113:9276-9286, 1991.

The invention claimed is:
1. An aminoglycoside-hydrophobe conjugate, wherein the aminoglycoside-hydrophobe conjugate is any one or more of the following:

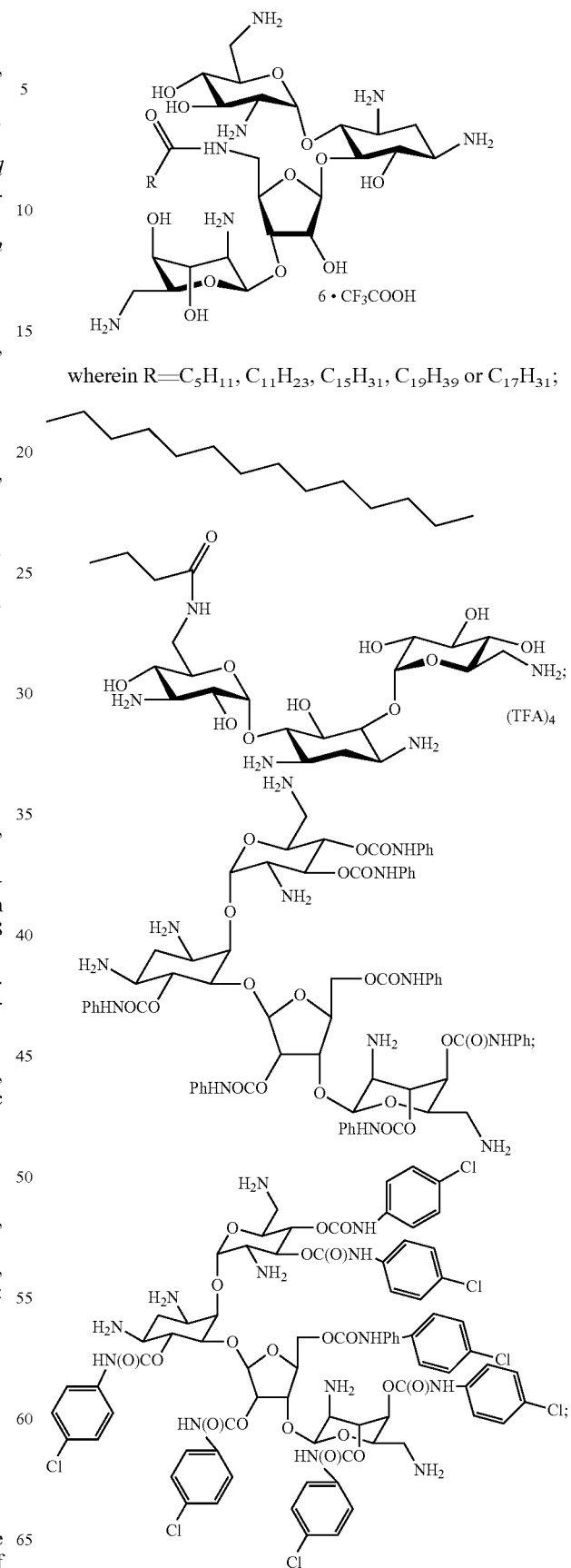

wherein $R=C_5H_{11}, C_{11}H_{23}, C_{15}H_{31}, C_{19}H_{39}$ or $C_{17}H_{31}$;

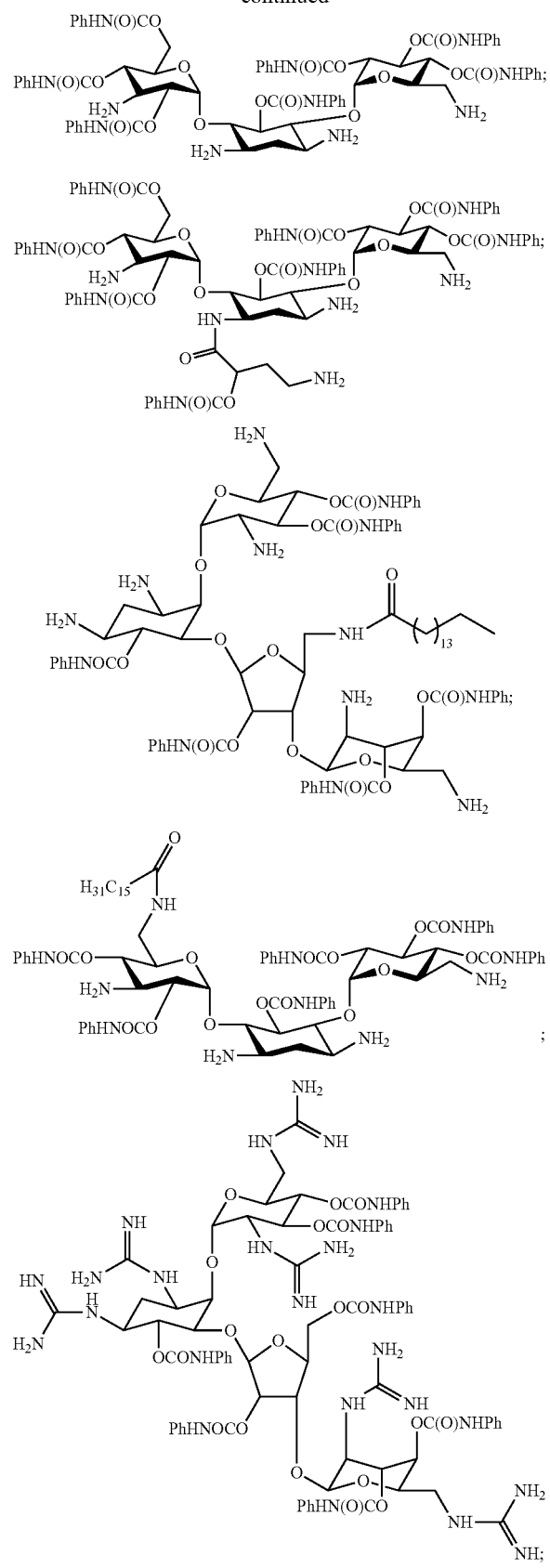

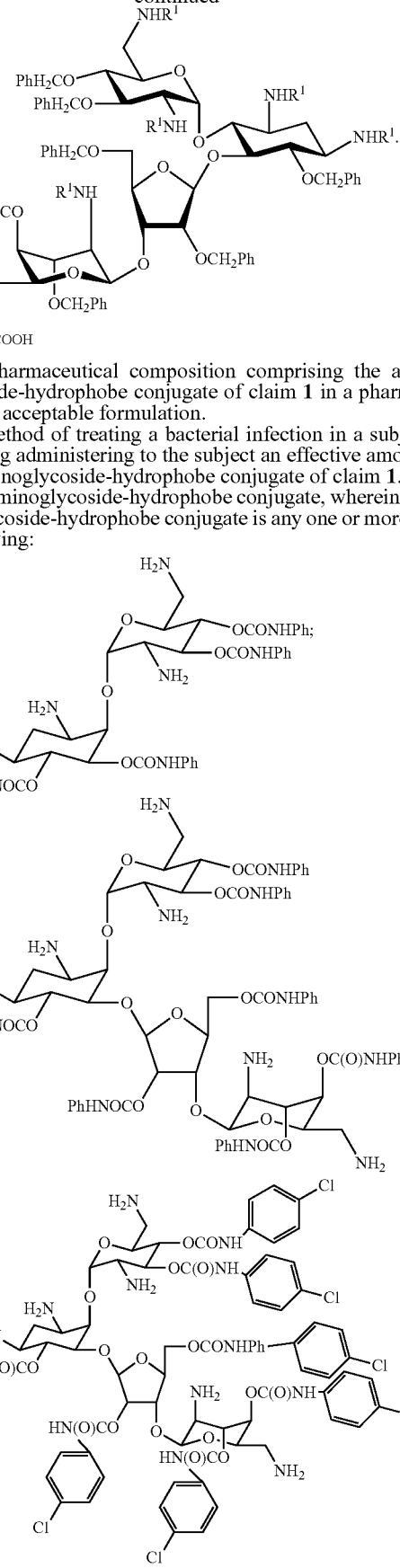

2. A pharmaceutical composition comprising the aminoglycoside-hydrophobe conjugate of claim 1 in a pharmaceutically acceptable formulation.

3. A method of treating a bacterial infection in a subject comprising administering to the subject an effective amount of the aminoglycoside-hydrophobe conjugate of claim 1.

4. An aminoglycoside-hydrophobe conjugate, wherein the aminoglycoside-hydrophobe conjugate is any one or more of the following:

61
-continued

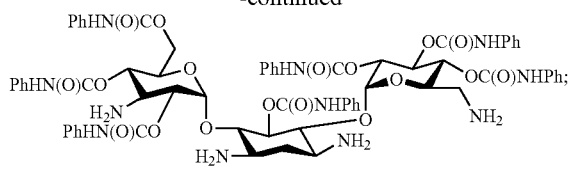
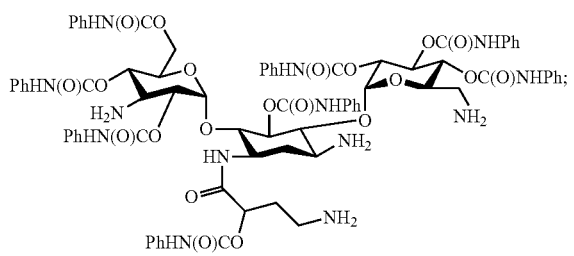
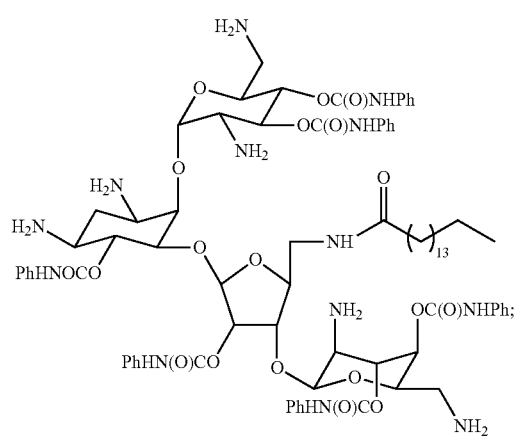
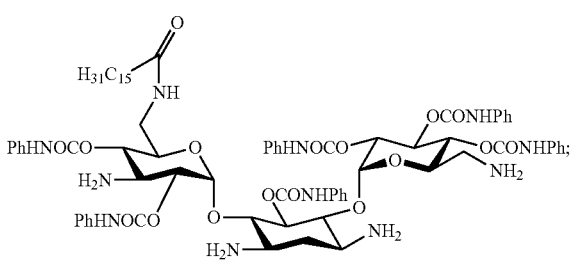

62
-continued

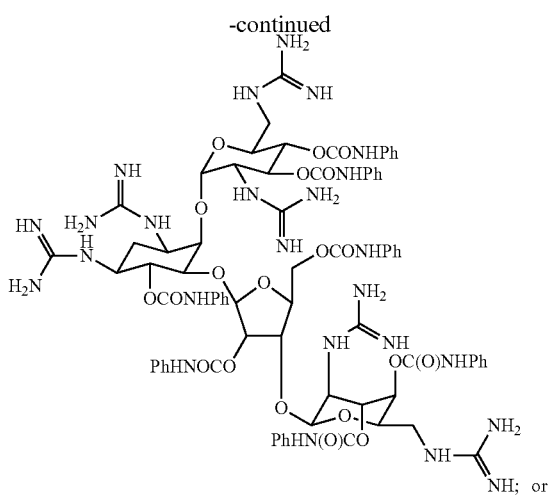
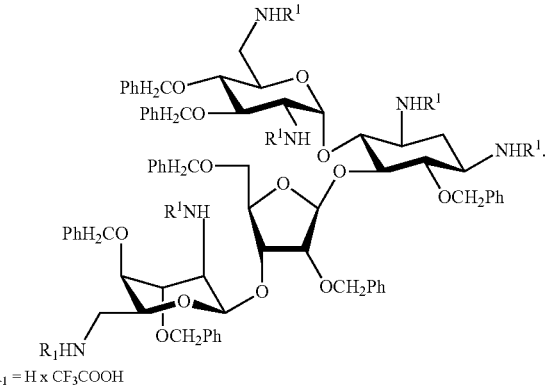

5. The aminoglycoside-hydrophobe conjugate of claim 4, wherein the aminoglycoside-hydrophobe conjugate is present as a trifluoroacetic acid salt.

6. A pharmaceutical composition comprising the aminoglycoside-hydrophobe conjugate of claim 4 in a pharmaceutically acceptable formulation.

7. A method of treating a bacterial infection in a subject comprising administering to the subject an effective amount of the aminoglycoside-hydrophobe conjugate of claim 4.

* * * * *

UNITED STATES PATENT AND TRADEMARK OFFICE
CERTIFICATE OF CORRECTION

PATENT NO. : 8,865,664 B2
APPLICATION NO. : 13/003175
DATED : October 21, 2014
INVENTOR(S) : Bera et al.

Page 1 of 1

It is certified that error appears in the above-identified patent and that said Letters Patent is hereby corrected as shown below:

In the claims,

In Claim 1 on Column 58, line 20,

"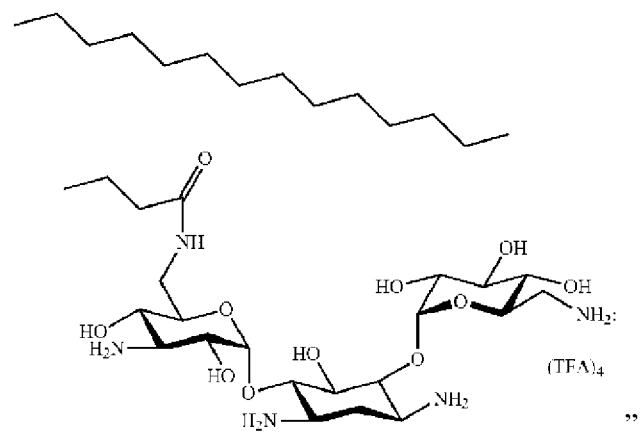"

should read

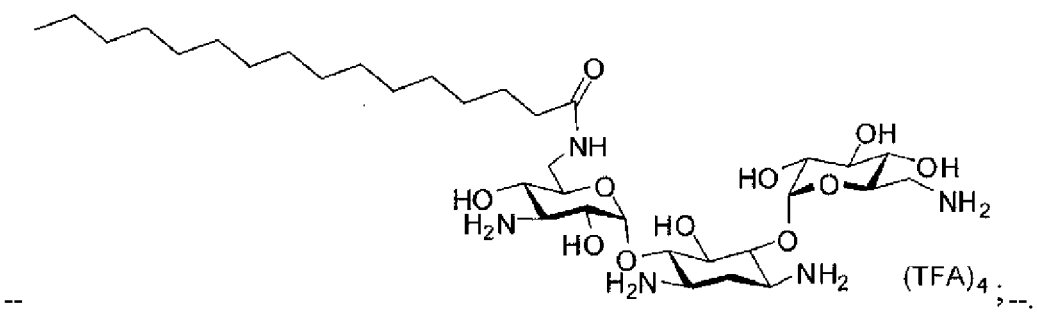

--

In Claim 1 on Column 58, line 56, delete "OCONHPh" and insert --OCONH-- therefor.

In Claim 4 on Column 60, line 58, delete "OCONHPh" and insert --OCONH-- therefor.

Signed and Sealed this
Fifteenth Day of March, 2016

Michelle K. Lee
*Director of the United States Patent and Trademark Office*